US011490835B2

United States Patent
Durlach et al.

(10) Patent No.: US 11,490,835 B2
(45) Date of Patent: Nov. 8, 2022

(54) SYSTEM FOR MANAGING PATIENT SUPPORT APPARATUSES AND PATIENT FALL RISKS

(71) Applicant: Stryker Corporation, Kalamazoo, MI (US)

(72) Inventors: Thomas Joseph Durlach, Kalamazoo, MI (US); Ross Michael Nave, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 321 days.

(21) Appl. No.: 16/832,766

(22) Filed: Mar. 27, 2020

(65) Prior Publication Data

US 2020/0305766 A1    Oct. 1, 2020

Related U.S. Application Data

(60) Provisional application No. 62/868,947, filed on Jun. 30, 2019, provisional application No. 62/868,387,
(Continued)

(51) Int. Cl.
*A61B 5/11* (2006.01)
*A61B 5/00* (2006.01)
(Continued)

(52) U.S. Cl.
CPC .......... *A61B 5/1117* (2013.01); *A61B 5/0022* (2013.01); *A61B 5/1115* (2013.01);
(Continued)

(58) Field of Classification Search
None
See application file for complete search history.

(56) References Cited

U.S. PATENT DOCUMENTS 7,319,386 B2 * 1/2008 Collins, Jr. .......... A61G 7/0527
340/286.07
8,421,606 B2    4/2013 Collins, Jr. et al.
(Continued)

FOREIGN PATENT DOCUMENTS

WO    2018013666 A1    1/2018

OTHER PUBLICATIONS

Stryker Operations Manual InTouch Critical Care Bed Model FL27, Apr. 2012.
(Continued)

*Primary Examiner* — Adolf Dsouza
(74) *Attorney, Agent, or Firm* — Warner Norcross + Judd LLP

(57) ABSTRACT

A caregiver assistance system is disclosed for assisting a caregiver to ensure the beds of high fall risk patients are in desired states for reducing the likelihood of a patient falling. The system may also help the caregiver to perform rounding tasks. The system comprises a server in communication with the patients' beds and one or more mobile electronic devices (e.g. smart phones). The mobile devices receive answers to a plurality of fall risk questions and forward them to the server. The server generates a patient fall risk assessment from the answers, determines a desired state for fall-risk components of the bed if the patient fall risk assessment indicates the patient has a high risk of falling, compares the states of the fall-risk components to corresponding desired states, and issues an alert at the mobile device if any of the fall-risk components are not in their desired state.

20 Claims, 21 Drawing Sheets

Related U.S. Application Data filed on Jun. 28, 2019, provisional application No. 62/868,360, filed on Jun. 28, 2019, provisional application No. 62/826,187, filed on Mar. 29, 2019, provisional application No. 62/826,195, filed on Mar. 29, 2019.

(51) Int. Cl.

| | | |
|---|---|---|
| *A61G 7/05* | (2006.01) | |
| *A61G 7/10* | (2006.01) | |
| *G16H 40/67* | (2018.01) | |
| *G16H 10/60* | (2018.01) | |
| *A61G 7/00* | (2006.01) | |
| *A61G 7/012* | (2006.01) | |
| *A61G 7/018* | (2006.01) | |
| *A61G 7/057* | (2006.01) | |

(52) U.S. Cl.
CPC ............ *A61B 5/447* (2013.01); *A61B 5/742* (2013.01); *A61G 7/001* (2013.01); *A61G 7/012* (2013.01); *A61G 7/018* (2013.01); *A61G 7/0516* (2016.11); *A61G 7/0527* (2016.11); *A61G 7/0528* (2016.11); *A61G 7/05769* (2013.01); *A61G 7/10* (2013.01); *G16H 10/60* (2018.01); *G16H 40/67* (2018.01); *A61B 2562/02* (2013.01); *A61G 2203/12* (2013.01)

(56) References Cited

U.S. PATENT DOCUMENTS

| | | |
|---|---|---|
| 9,177,465 B2 | 11/2015 | Vanderphol, III |
| 9,240,120 B2 | 1/2016 | Girardeau et al. |
| 9,465,916 B2 | 10/2016 | Girardeau et al. |
| 9,659,148 B2 | 5/2017 | Girardeau et al. |
| 9,971,869 B2 | 5/2018 | Girardeau et al. |
| 2002/0014951 A1 | 2/2002 | Kramer et al. |
| 2007/0010719 A1 | 1/2007 | Huster et al. |
| 2007/0163045 A1 | 7/2007 | Becker et al. |
| 2014/0094997 A1 | 4/2014 | Hyde et al. |
| 2014/0297327 A1 | 10/2014 | Heil et al. |
| 2016/0213537 A1 | 7/2016 | Hayes et al. |
| 2016/0338891 A1 | 11/2016 | Agdeppa et al. |
| 2016/0367415 A1 | 12/2016 | Hayes et al. |
| 2016/0367420 A1 | 12/2016 | Zerhusen et al. |

OTHER PUBLICATIONS

Copending U.S. Appl. No. 15/295,722, filed Oct. 17, 2016.
Stryker Corporation "iBed Wireless" Brochure, 2018.

\* cited by examiner

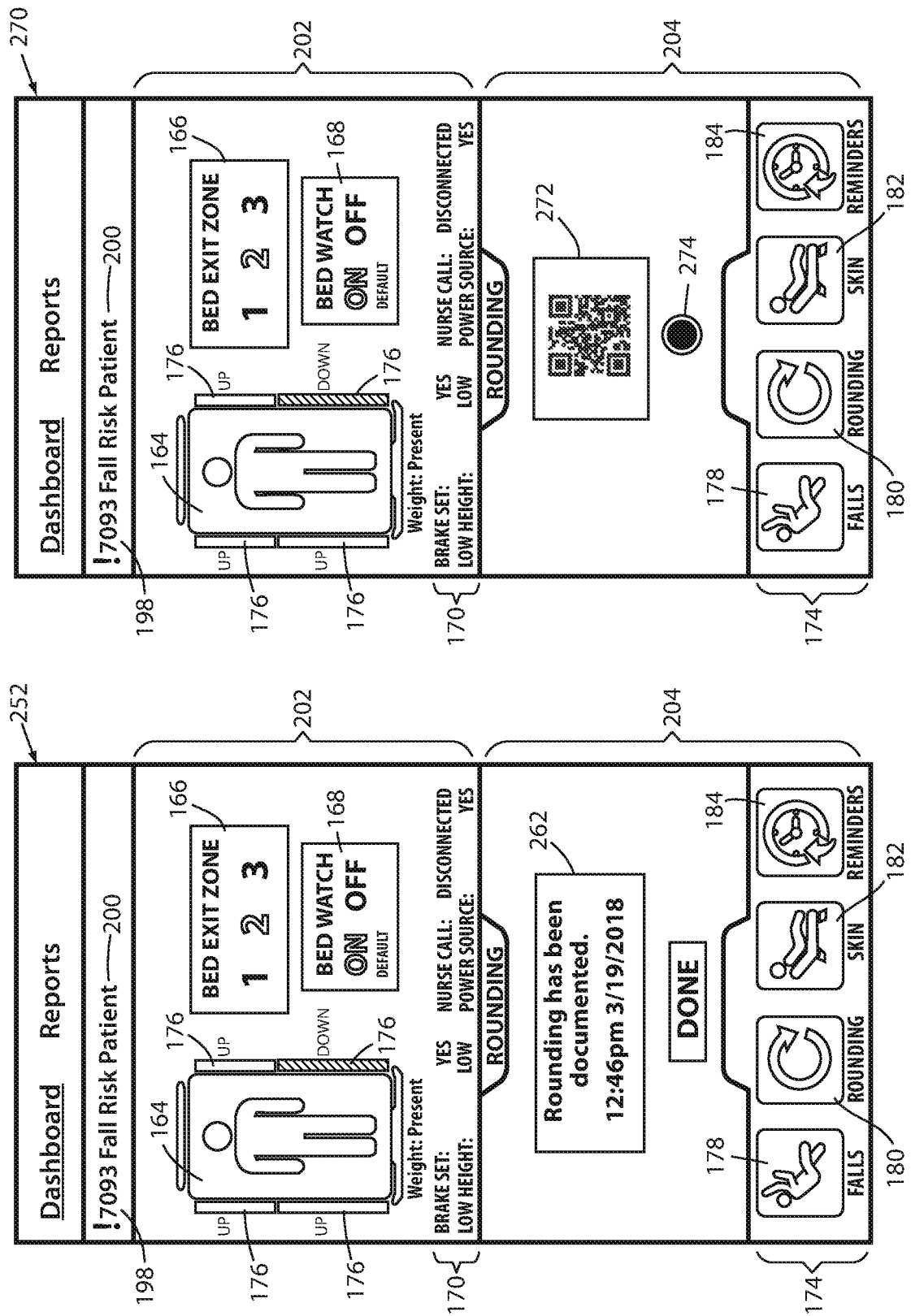

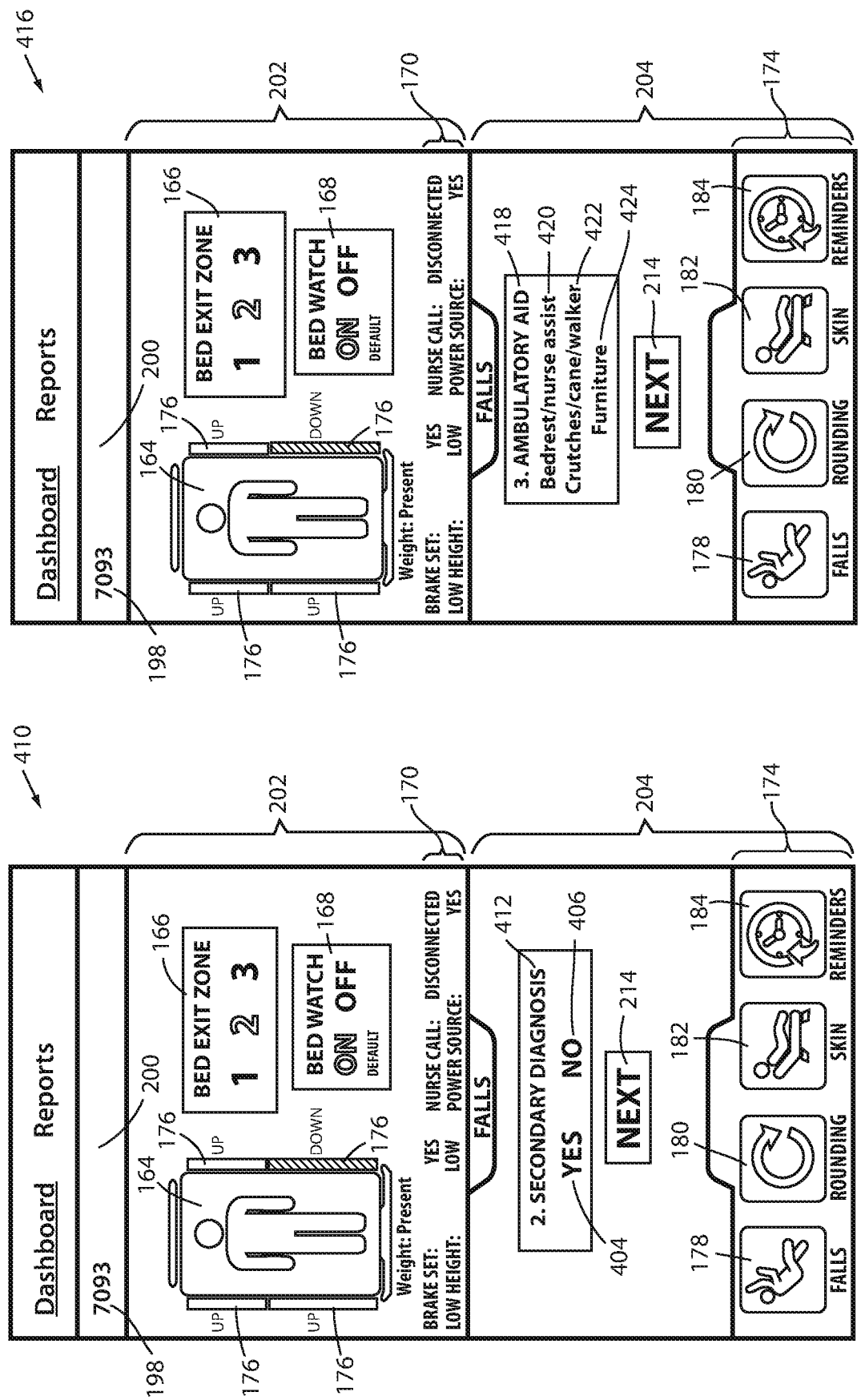

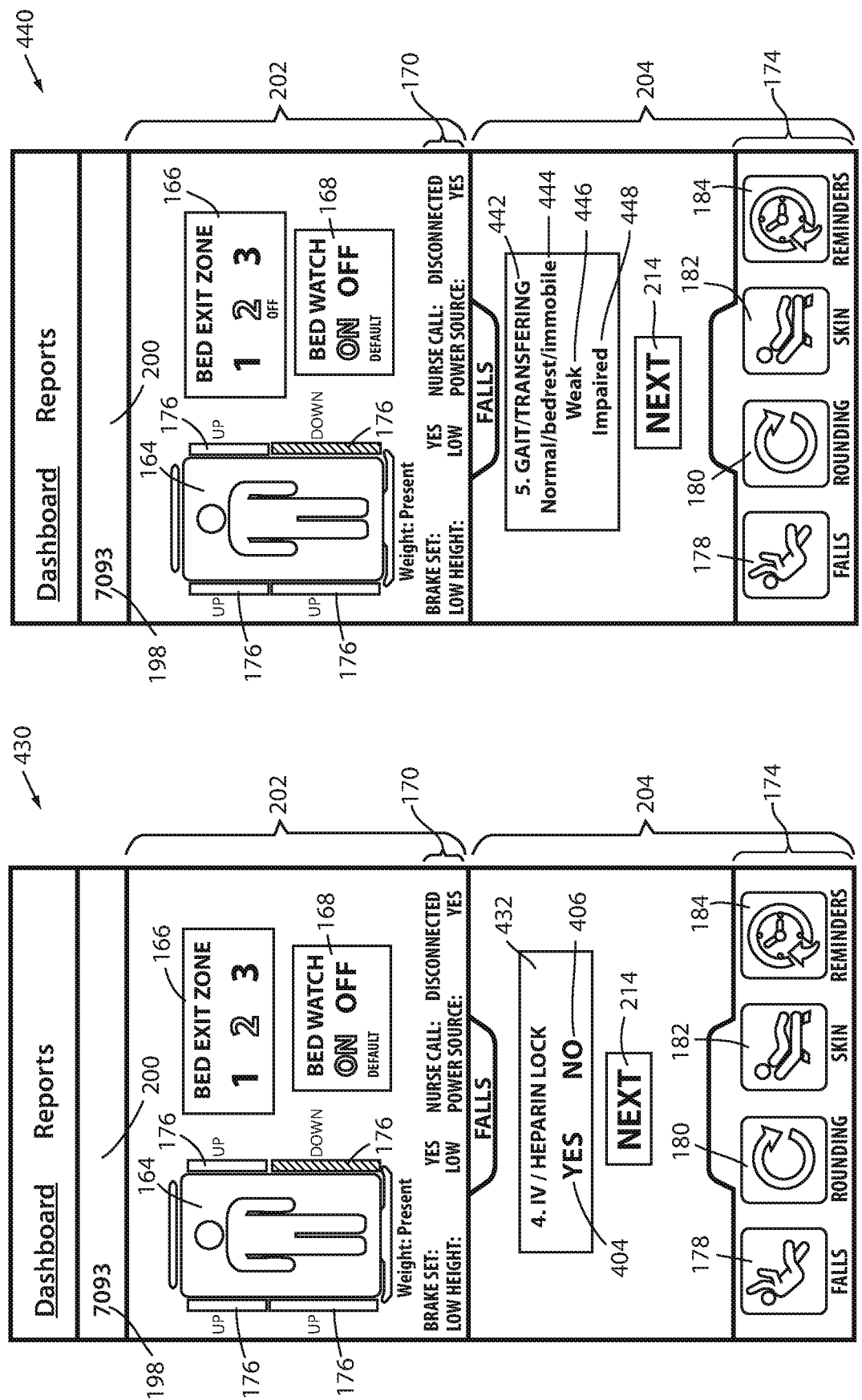

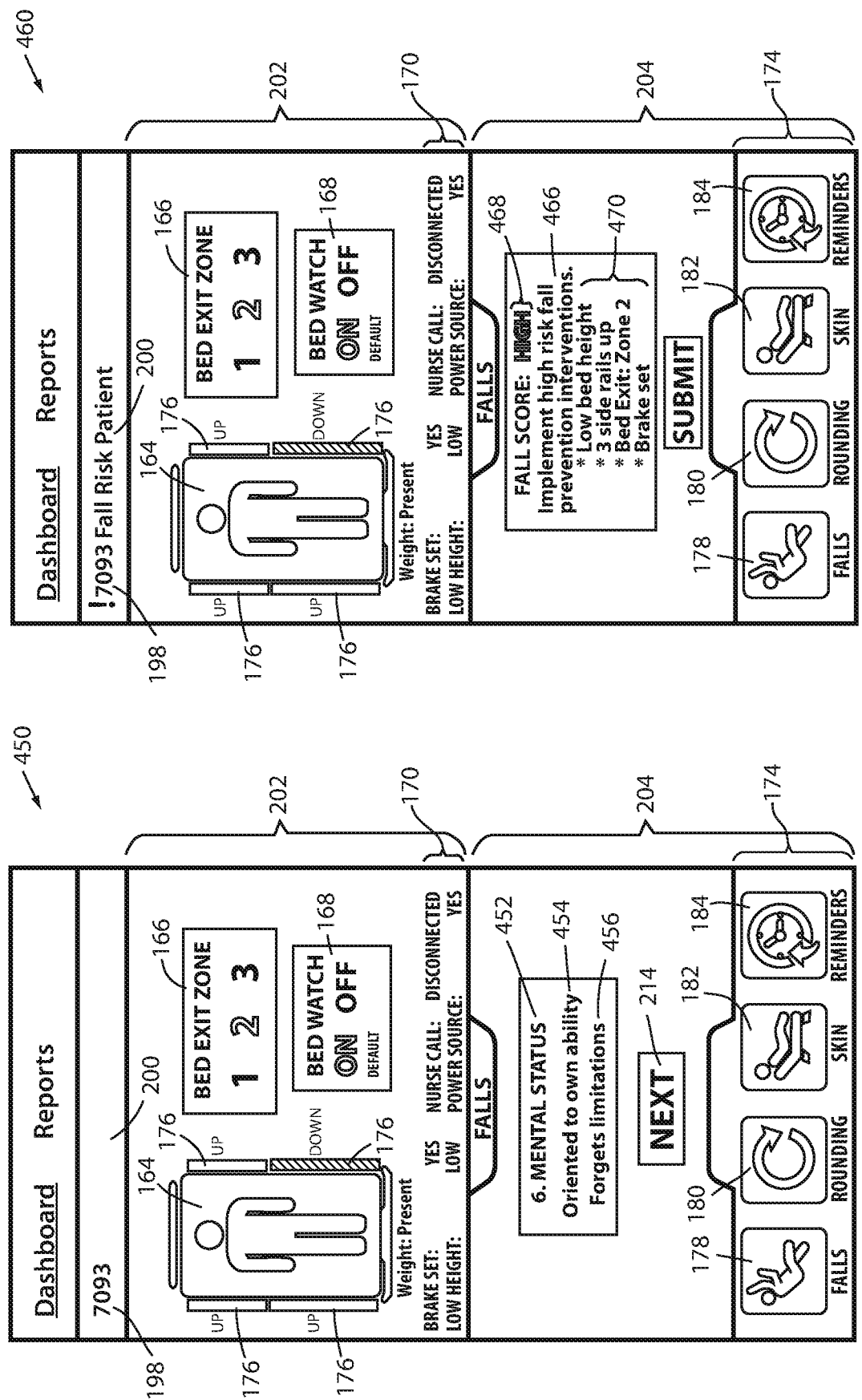

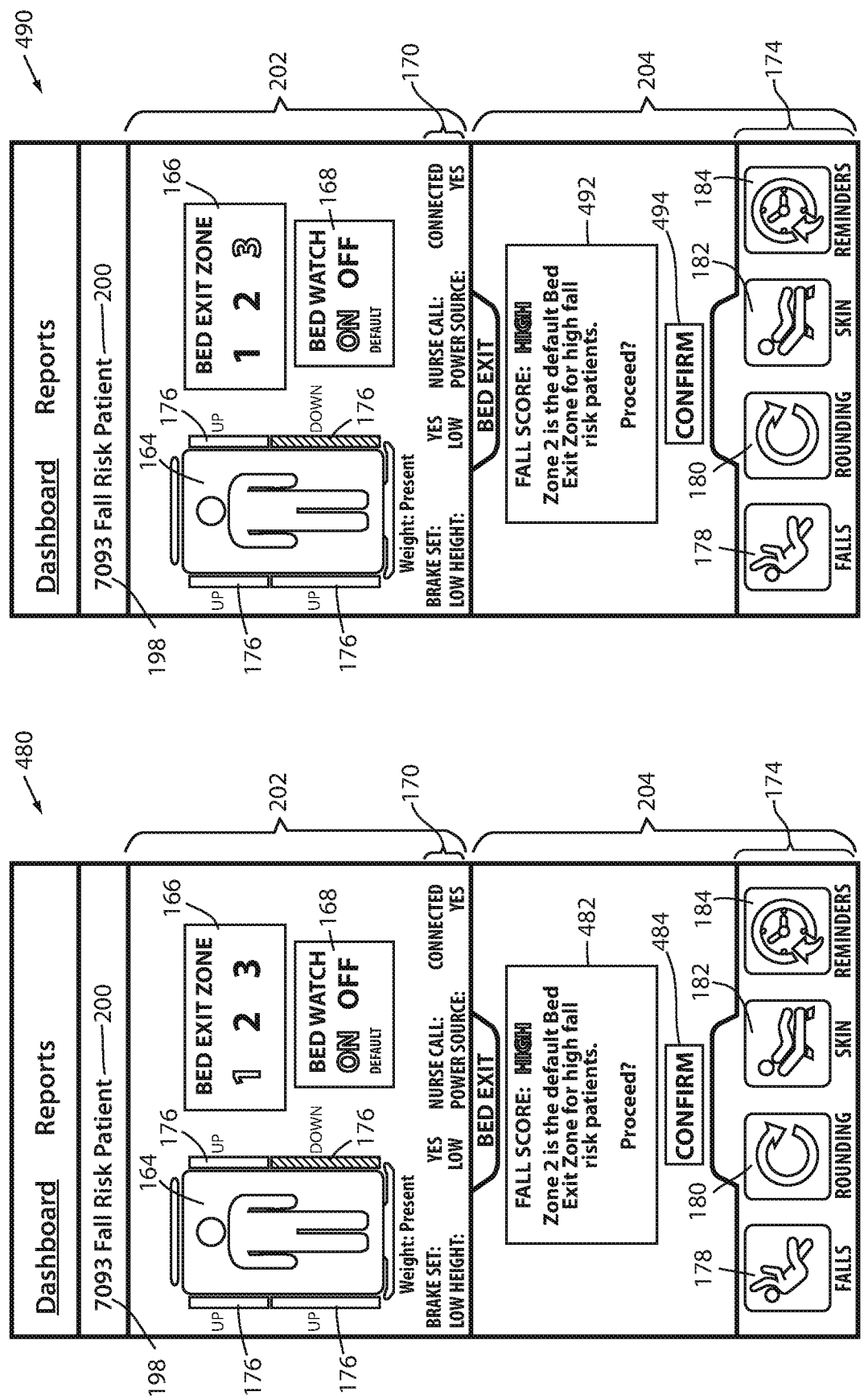

SYSTEM FOR MANAGING PATIENT SUPPORT APPARATUSES AND PATIENT FALL RISKS

CROSS-REFERENCE TO RELATED APPLICATIONS

This application claims priority to the following U.S. patent applications: 62/868,947 filed Jun. 30, 2019, by inventors Thomas Durlach et al. and entitled CAREGIVER ASSISTANCE SYSTEM; 62/868,387 filed Jun. 28, 2019, by inventors Thomas Durlach et al. and entitled CAREGIVER ASSISTANCE SYSTEM; 62/826,187 filed Mar. 29, 2019, by inventors Thomas Durlach et al. and entitled SYSTEM FOR MANAGING PATIENT SUPPORT APPARATUSES AND PATIENT FALL RISKS; 62/868,360 filed Jun. 28, 2019, by inventors Thomas Durlach et al. and entitled CAREGIVER ASSISTANCE SYSTEM; and 62/826,195 filed Mar. 29, 2019, by inventors Thomas Durlach et al. and entitled SYSTEM FOR MANAGING PATIENT SUPPORT APPARATUSES AND BED SORE RISKS, the complete disclosures of all of which are incorporated herein by reference. This patent application also incorporates by reference the complete disclosures of U.S. patent application Ser. No. 16/716,725 filed Dec. 17, 2019, by inventors Thomas Durlach et al. and entitled SYSTEM FOR MANAGING PATIENT SUPPORT APPARATUSES AND CLINICAL ROUNDS, and Ser. No. 16/716,729 filed Dec. 17, 2019, by inventors Thomas Durlach et al. and entitled SYSTEM FOR MANAGING PATIENT SUPPORT APPARATUSES AND CLINICAL ROUNDS.

BACKGROUND

The present disclosure relates to patient support apparatuses, such as beds, cots, stretchers, operating tables, recliners, or the like. More specifically, the present disclosure relates to a system for assisting caregivers with both the management of such patient support apparatuses and the performance of other tasks, such as, but not limited to, their rounding tasks.

Hospitals typically expect nurses and/or other caregivers to perform a variety of different duties when carrying for patients. These duties include administering medications and/or therapies, taking vital sign readings, installing and removing IV drips, taking blood samples, ensuring patient compliance with prescribed activities and/or medications, assisting the patient into and out of bed, regularly visiting the patient, configuring the patient's bed to be in a desired state, documenting one or more of these activities, and generally being responsive to the patient's needs. One of these duties including performing what are customarily known as patient rounds. Such rounding duties involve the caregiver personally checking on the wellbeing of the patient at certain specified intervals. Hospital administrators typically specify a minimum frequency at which the caregivers are to perform these rounding duties, such as, for example, at least once every two hours. In some situations, the rounding frequencies may vary based on the medical condition of the patient, the wing or section of the hospital, and/or other factors.

Hospitals also typically expect nurses and/or other caregivers to help reduce the risk of patients falling. In many hospitals, patients are to be assigned a fall risk and, if the fall risk exceeds a certain threshold, certain steps are to be taken by the caregiver in order to reduce the likelihood of the patient falling while in the hospital. Such fall risk reduction steps often involve placing one or more components of the hospital bed into one or more desired states, such as, for example, arming an exit detection system, activating a brake, etc. In many hospitals, the tasks and responsibility of nurses and other caregivers can be manifold and substantial, and technology that assists these caregivers in meeting their responsibilities and providing quality healthcare to their patients is desirable.

SUMMARY

According to various embodiments, a tool for assisting caregivers in carrying out several of their patient care responsibilities is provided herein. According to some embodiments, a tool is specifically provided for facilitating the caregiver's fall-risk reduction duties, as well as other duties, such as, but not limited to the caregiver's rounding duties. The tool may assist with the caregiver's fall-risk reduction duties by helping the caregiver to ensure that the patient's bed is in a desired configuration and that the patient's fall risk is properly and timely determined. The tool can be particularly helpful in situations where the desired configuration of the bed is deemed to have, or is otherwise treated as having, a lower priority than the other duties assigned to a caregiver. According to other embodiments, the tool may additionally assist the caregiver with performing still other duties, such as reminding the caregiver to perform certain activities, evaluating one or more aspects of the patient's health (e.g. whether the patient is at risk for bed sores, and/or other undesirable conditions); documenting one or more aspects of the patient's care, and/or other duties. In some embodiments, the tool combines bed status data with rounding data so that the caregiver is reminded of undesirable bed states while he or she is carrying out his or her rounding duties. More particularly, the tool may provide an alert to the caregiver of an undesirable bed configuration while the caregiver is using other functions of the tool, thereby allowing the caregiver to perform other tasks while the bed compliance issues are monitored. The tool also eliminates the need for the caregiver to access and/or utilize separate tools for performing disparate patient care tasks. In order to better ensure that the bed is configured to a fall-risk reduced state, the rounding functions—or other functions—of the tool may be rendered partially or wholly inoperative when a bed is not configured to reduce fall risks. These and other aspects of the present disclosure will be apparent to one skilled in the art in light of the following written description.

According to one embodiment of the present disclosure, a caregiver assistance system is provided for assisting a caregiver to reduce patient fall risks. The caregiver assistance system includes a plurality of beds and a server. Each of the beds includes a litter frame, a support deck, a memory, a transceiver, a sensor, and a controller. The support deck is supported on the litter frame and configured to support a patient thereon. The memory contains an identifier uniquely identifying the respective bed. The sensor detects a state of a fall-risk component of the respective bed, and the controller transmits a message via the transceiver that includes the respective identifier. The server is configured to execute a caregiver assistance application that receives the messages from the plurality of bed, as well as a patient fall risk assessment from an external device. The patient fall risk assessment identifies a fall risk of a particular patient, and the caregiver assistance application matches the patient fall risk assessment to a specific one of the beds to which the particular patient has been assigned.

According to other aspects of the present disclosure, the external device is a mobile electronic device carried by a caregiver and adapted to receive fall risk data from the caregiver. The mobile electronic device is configured to generate the patient fall risk assessment from the fall risk data.

In some embodiments, the mobile electronic device is one of a smart phone, a tablet computer, or a laptop computer.

The fall risk data, in some embodiments, includes answers to a set of questions regarding the particular patient.

The server, in some embodiments, includes a memory in which state data is stored defining a desired state of the fall-risk component for patients having a high fall risk. The caregiver assistance application determines if the fall risk of the particular patient qualifies as a high fall risk and, if it does, determines if the fall-risk component of the specific one of the beds is in the desired state based upon data received from the sensor of the specific one of the beds.

In at least one other embodiment, the specific one of the beds includes a plurality of sensors adapted to detect states of a plurality of fall-risk components. In this embodiment, the state data includes desired states for each of the plurality of fall-risk components, and the caregiver assistance application determines if any of the plurality of fall-risk components of the specific one of the beds are not in their respective desired states. The caregiver assistance application is adapted to communicate with a mobile electronic device carried by a caregiver and to provide data to the mobile electronic device indicating whether the plurality of fall-risk components of the specific one of the beds are in their respective desired states or not.

In some embodiments, the caregiver assistance application is further adapted to provide data to the mobile electronic device identifying the fall-risk component. The identification may include a graphical depiction of the specific one of the beds on the display of the mobile electronic device, wherein the graphical depiction includes the fall-risk component.

The plurality of fall-risk components of the beds, in at least one embodiment, includes a brake adapted to selectively brake a wheel; a siderail adapted to move between a raised and lowered position; a lift system adapted to change a height of the litter frame; and an exit detection system adapted to issue an alert when the exit detection system is armed and the particular patient exits from the specific one of the beds.

In some embodiments, the external device is one of an electronic medical records (EMR) server or an Admission, Discharge, and Tracking (ADT) server.

The mobile electronic device, in some embodiments, is a browser enabled device configured to receive the data from the caregiver assistance application by accessing at least one Uniform Resource Locator (URL) associated with the server.

The mobile electronic device may be configured to receive a room identifier from the caregiver and to forward the room identifier to the caregiver assistance application. In response, the caregiver assistance application associates the room identifier with the particular patient.

In some embodiments, the caregiver assistance application causes the mobile electronic device to display an alert if any of the plurality of fall-risk components of the specific one of the beds are not in their respective desired states.

The caregiver assistance application, in some embodiments, is further adapted to cause the mobile electronic device to display rounding data thereon. The rounding data indicates at least one of: an amount of time since a caregiver last completed a rounding task associated with the particular patient, or an amount of time until the caregiver is supposed to complete a future rounding task associated with the particular patient.

According to another embodiment of the present disclosure, a caregiver assistance system for assisting a caregiver to reduce patient fall risks includes a bed and a server. The bed includes a litter frame, a support deck, a memory, a transceiver, a plurality of sensors, and a controller. The support deck is supported on the litter frame and configured to support a patient thereon. The memory contains an identifier uniquely identifying the bed. The plurality of sensors are adapted to detect states of a plurality of fall-risk components of the bed. The controller transmits the identifier and the states of the plurality of fall-risk components via the transceiver to the server. The server is configured to execute a caregiver assistance application that receives the identifier and the states of the plurality of fall-risk components of the bed. The caregiver assistance application also monitors compliance of the plurality of fall-risk components with a fall risk reduction protocol. The caregiver assistance application is further configured to communicate with a mobile electronic device comprising a display, a user input, and a web browser configured to be able to access a particular Uniform Resources Locator (URL) associated with the caregiver assistance application. The caregiver assistance application is still further configured to cause the mobile electronic device to perform the following after accessing the particular URL: (i) display the states of the plurality of fall-risk components of the bed; (ii) receive fall risk data via the user input from a caregiver associated with the mobile electronic device and the bed; (iii) transmit the fall risk data to the server; and (iv) issue an alert if any of the states of the plurality of fall-risk components of the bed do not comply with the fall risk reduction protocol.

According to another aspect of the present disclosure, the caregiver assistance application is further configured to cause the mobile electronic device to perform the following after accessing the particular URL: display a set of questions relating to a fall risk of the patient; receive answers to the set of questions; and transmit the answers to the server.

In some embodiments, the caregiver assistance application is further configured to cause the mobile electronic device to receive data from the user input defining a change to the fall risk reduction protocol.

The beds, in some embodiments, include a user interface adapted to allow a user to input data defining a change to the fall risk reduction protocol.

The caregiver assistance system may further comprise: (a) a brake adapted to selectively brake a wheel; (b) a siderail adapted to move between a raised and lowered position; (c) a lift system adapted to change a height of the litter frame; and (d) an exit detection system adapted to issue an alert when the exit detection system is armed and the patient exits from the bed. In such embodiments, the plurality of sensors of the bed include at least the following: (i) a brake sensor adapted to detect whether the brake is activated or inactivated; (ii) a siderail position sensor adapted to detect whether the siderail is in the raised or lowered position; (iii) a height sensor adapted to detect a height of the litter frame; and (iv) an exit detection armed sensor adapted to detect when the exit detection system is armed. Still further, in such embodiments, the fall risk reduction protocol defines desired states for each of the brake, siderail, lift system, and exit detection system.

The caregiver assistance application, in some embodiments, is further adapted to use the answers to the set of questions received from the mobile electronic device to generate a patient fall risk assessment, and to determine whether the fall risk reduction protocol is to be followed for the bed or not based upon the patient fall risk assessment.

In some embodiments, the caregiver assistance application is further adapted to forward the patient fall risk assessment to an electronic medical records server in communication with the server.

The bed may further comprise a user interface adapted to allow a user to input data defining the fall risk reduction protocol. In such embodiments, the caregiver assistance application is adapted to receive the data defining the fall risk reduction protocol from the bed.

In some embodiments, the caregiver assistance application is further configured to allow the mobile electronic device to receive a command to arm the exit detection system from a user and to forward the command to the bed. The controller on the bed arms the exit detection system in response to receiving the command.

According to another embodiment of the present disclosure, a caregiver assistance system for assisting a caregiver to reduce patient fall risks is provided. The caregiver assistance system includes a bed and a server. The bed includes a litter frame, a support deck, a memory, a transceiver, a plurality of sensors, and a controller. The support deck is supported on the litter frame and configured to support a patient thereon. The memory contains an identifier uniquely identifying the bed. The sensors detect states of a plurality of fall-risk components of the bed. The controller transmits the identifier and the states of the plurality of fall-risk components to the server via the transceiver. The server is configured to execute a caregiver assistance application that performs the following: (i) communicates with a mobile electronic device comprising a display and a user input; (ii) receives from the mobile electronic device answers to a plurality of fall risk questions; (iii) generates a patient fall risk assessment from the answers; (iv) determines a desired state for each of the plurality of fall-risk components of the bed if the patient fall risk assessment indicates the patient has a high risk of falling; (v) compares the states of the plurality of fall-risk components to corresponding ones of the desired states of each of the plurality of fall-risk components; and (vi) issues an alert at the mobile electronic device if at least one of the states of the plurality of fall-risk components does not match the corresponding desired state.

According to other aspects of the present disclosure, the plurality of fall-risk components comprises: a brake adapted to selectively brake a wheel; a siderail adapted to move between a raised and lowered position; a lift system adapted to change a height of the litter frame; and an exit detection system adapted to issue an alert when the exit detection system is armed and the patient exits from the bed. In such embodiments, the plurality of sensors comprises: a brake sensor adapted to detect whether the brake is activated or inactivated; a siderail position sensor adapted to detect whether the siderail is in the raised or lowered position; a height sensor adapted to detect a height of the litter frame; and an exit detection armed sensor adapted to detect when the exit detection system is armed. The desired state for each of these fall-risk components, in such embodiments, includes a desired state for each of the brake, siderail, lift system, and exit detection system.

In some embodiments, the caregiver assistance application determines the desired state for each of the plurality of fall-risk components by consulting a fall risk reduction protocol stored in the memory. The fall risk reduction protocol specifies desired states for each of the plurality of fall-risk components when the patient has a high risk of falling.

In some embodiments, the bed further comprises a user interface adapted to allow a user to input data defining the fall risk reduction protocol and the caregiver assistance application is adapted to receive and store in the memory the data defining the fall risk reduction protocol from the bed.

The caregiver assistance application, in some embodiments, issues the alert by sending at least one of the following to the mobile electronic device: an email or a text message.

The caregiver assistance application may further be adapted to cause the mobile electronic device to receive rounding data from a caregiver indicating a rounding task was completed, as well as to cause the mobile electronic device to capture verification data verifying the caregiver was physically present adjacent the bed at a time the rounding task was completed.

In some embodiments, the mobile electronic device includes a camera and the verification data includes image data taken with the camera of at least a portion of the bed. Alternatively, or additionally, the bed may include a first near field transceiver and the mobile electronic device may include a second near field transceiver, wherein the verification data includes data communicated from the bed to the mobile electronic device via the first and second near field transceivers.

According to yet another embodiment of the present disclosure, a caregiver assistance system for assisting a caregiver to reduce patient fall risks is provided. The caregiver assistance system comprises a bed and a server. The bed comprises a litter frame, a support deck, a memory, a transceiver, a plurality of sensors, and a controller. The support deck is supported on the litter frame and configured to support a patient thereon. The memory contains an identifier uniquely identifying the bed. The plurality of sensors are adapted to detect states of a plurality of fall-risk components of the bed. The controller is adapted to transmit the identifier and the states of the plurality of fall-risk components to the server via the transceiver. The server executes a caregiver assistance application that is configured to determine a desired state for each of the plurality of fall-risk components of the bed if a patient fall risk assessment indicates the patient has a high risk of falling. The caregiver assistance application also compares the states of the plurality of fall-risk components to corresponding ones of the desired states of each of the plurality of fall-risk components. Still further, the caregiver assistance application also performs the following: communicates with a mobile electronic device comprising a display and a user input; receives from the mobile electronic device data indicating a caregiver has completed a rounding task associated with the patient; captures verification data verifying that the caregiver was physically present adjacent the bed when the rounding task was completed; and causes the mobile electronic device to issue an alert if at least one of the states of the plurality of fall-risk components does not match the corresponding desired state.

According to other aspects, the caregiver assistance application may further be adapted to cause the mobile electronic device to display a time at which a future rounding task is to be performed for the patient, and/or a time at which a previous rounding task was performed for the patient.

In some embodiments, the caregiver assistance application is further configured to receive from the mobile electronic device answers to a plurality of fall risk questions and to generate a patient fall risk assessment from the answers.

The caregiver assistance application may further be configured to forward the patient fall risk assessment to an electronic medical records server in communication with the server.

In some embodiments, the caregiver assistance application is further configured to allow the mobile electronic device to receive a command to arm the exit detection system from a user and to forward the command to the bed. The controller arms the exit detection system in response to receiving the command.

In any of the embodiments disclosed herein, multiple beds and/or multiple mobile electronic devices may be included that are in communication with the server. The caregiver assistance application keeps track of which beds are associated with which rooms and/or caregivers. In some embodiments, the caregiver assistance application is configured to only supply bed status information for beds that are positioned in particular rooms assigned to a particular caregiver. That is, not all users of the caregiver assistance application are able to access the bed status data and/or patient fall risk data for all beds and/or all patients within the healthcare facility. Instead, the caregiver assistance application includes a log-in process that identifies a particular user. The caregiver assistance application then automatically limits that particular user's access to patient and/or bed information according to that person's credentials and/or work assignment. In this way, a first caregiver assigned to patients A, B, and C is not typically able to access information about patient D and/or patient D's bed. Similarly, a second caregiver assigned to patients D, E, and F is not typically able to access information about patients A, B, or C. In some embodiments, the caregiver assistance application is configured to allow users to share information and/or swap assignments, thereby permitting different users to view different patient and/or bed data.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

BRIEF DESCRIPTION OF THE DRAWINGS

FIG. 14 is an illustrative screenshot of rounding completion screen that is displayable on an electronic device of the caregiver assistance system;

FIG. 15 is an illustrative screenshot of a first rounding verification screen that is displayable on an electronic device of the caregiver assistance system;

FIG. 20 is an illustrative screenshot of a second fall risk assessment question screen that is displayable on an electronic device of the caregiver assistance system;

FIG. 21 is an illustrative screenshot of a third fall risk assessment question screen that is displayable on an electronic device of the caregiver assistance system;

FIG. 22 is an illustrative screenshot of a fourth fall risk assessment question screen that is displayable on an electronic device of the caregiver assistance system;

FIG. 23 is an illustrative screenshot of a fifth fall risk assessment question screen that is displayable on an electronic device of the caregiver assistance system;

FIG. 24 is an illustrative screenshot of a sixth fall risk assessment question screen that is displayable on an electronic device of the caregiver assistance system;

FIG. 25 is an illustrative screenshot of a fall risk assessment information screen that is displayable on an electronic device of the caregiver assistance system;

FIG. 26 is an illustrative screenshot of a first bed exit advisory screen that is displayable on an electronic device of the caregiver assistance system;

FIG. 27 is an illustrative screenshot of a second bed exit advisory screen that is displayable on an electronic device of the caregiver assistance system;

DETAILED DESCRIPTION OF THE EMBODIMENTS

Figure 1:
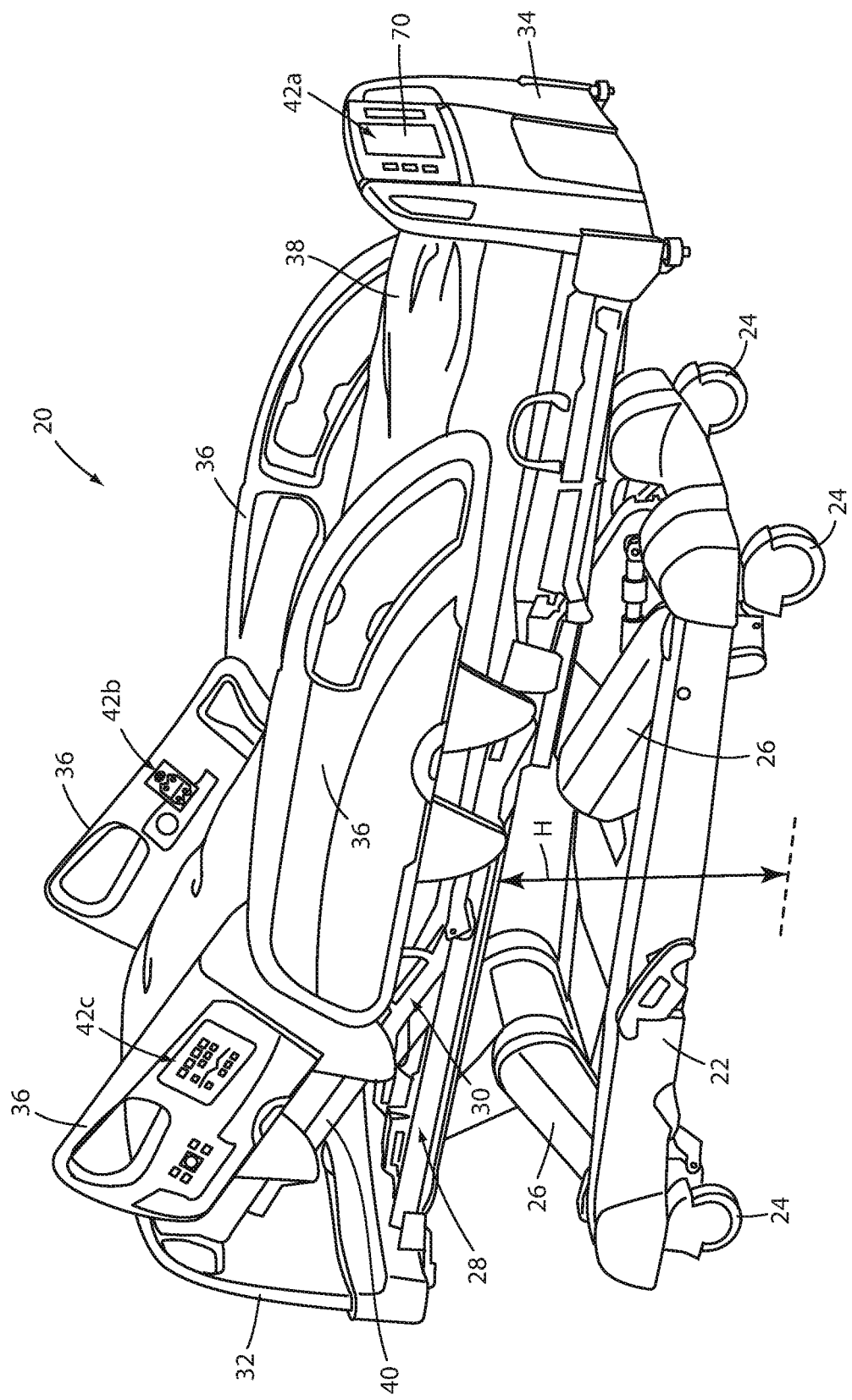
FIG. 1 is a perspective view of a patient support apparatus usable in a caregiver assistance system according to one embodiment of the disclosure.

An illustrative patient support apparatus 20 usable in a caregiver assistance system according to the present disclosure is shown in FIG. 1. Although the particular form of patient support apparatus 20 illustrated in FIG. 1 is a bed adapted for use in a hospital or other medical setting, it will be understood that patient support apparatus 20 could, in different embodiments, be a cot, a stretcher, a recliner, or any other structure capable of supporting a patient while the patient is in a healthcare facility, such as, but not limited to, a hospital. For purposes of the following written description, patient support apparatus 20 will be primarily described as a bed with the understanding that the following written description applies to these other types of patient support apparatuses.

In general, patient support apparatus 20 includes a base 22 having a plurality of wheels 24, a lift subsystem comprising a pair of lifts 26 supported on the base, a litter frame 28 supported on the lifts 26, and a support deck 30 supported on the litter frame 28. Patient support apparatus 20 further includes a headboard 32, a footboard 34, and a plurality of siderails 36. Siderails 36 are all shown in a raised position in FIG. 1 but are each individually movable to a lower position in which ingress into, and egress out of, patient support apparatus 20 is not obstructed by the lowered siderails 36. In some embodiments, siderails 36 may be moved to one or more intermediate positions as well.

Lifts 26 are configured to raise and lower litter frame 28 with respect to base 22. Lifts 26 may be hydraulic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted. That is, litter frame 28 includes a head end and a foot end, each of whose height can be independently adjusted by the nearest lift 26. Patient support apparatus 20 is designed so that when an occupant lies thereon, his or her head will be positioned adjacent the head end and his or her feet will be positioned adjacent the foot end.

Litter frame 28 provides a structure for supporting support deck 30, the headboard 32, footboard 34, and siderails 36. Support deck 30 provides a support surface for a mattress 38, or other soft cushion, so that a person may lie and/or sit thereon. Support deck 30 is made of a plurality of sections, some of which are pivotable about generally horizontal pivot axes. In the embodiment shown in FIG. 1, support deck 30 includes a head section 40, which is also sometimes referred to as a Fowler section or a backrest section. Head section 40 is pivotable about a generally horizontal pivot axis between a generally horizontal orientation (not shown in FIG. 1) and a plurality of raised positions (one of which is shown in FIG. 1). Support deck 30 may include additional sections that are pivotable about one or more horizontal pivot axes, such as an upper leg or thigh section and/or a lower leg or foot section (not labeled).

Patient support apparatus 20 further includes a plurality of control panels 42 that enable a user of patient support apparatus 20, such as a patient and/or an associated caregiver, to control one or more aspects of patient support apparatus 20. In the embodiment shown in FIG. 1, patient support apparatus 20 includes a footboard control panel 42a, a pair of inner siderail control panels 42b (only one of which is visible), and a pair of outer siderail control panels 42c (only one of which is visible). Footboard control panel 42a and outer siderail control panels 42c are intended to be used by caregivers, or other authorized personnel, while inner siderail control panels 42b are intended to be used by the patient associated with patient support apparatus 20. Not all of the control panels 42 include the same controls and/or functionality. In the illustrated embodiment, footboard control panel 42a includes a substantially complete set of controls for controlling patient support apparatus 20 while control panels 42b and 42c include a selected subset of those controls. One or more of any of control panels 42a, b, and/or c may include a height adjustment control that, when activated, changes a height of litter frame 28 relative to base 22.

Control panels 42a and/or 42c may include controls for allowing a user to do one or more of the following: activate and deactivate a brake for wheels 24, arm an exit detection system 46, take a weight reading of the patient, activate and deactivate a propulsion system, and communicate with a healthcare facility computer network installed in the healthcare facility in which patient support apparatus 20 is positioned. Inner siderail control panels 42b may also include a nurse call control that enables a patient to call a nurse. A speaker and microphone are included on, or adjacent to, inner siderail control panel 42b in order to allow the patient to aurally communicate with the remotely positioned nurse.

Footboard control panel 42a is implemented in the embodiment shown in FIG. 1 as a touchscreen display 70 having a plurality of controls 72 positioned alongside the touchscreen display 70. Controls 72 may be implemented as buttons, dials, switches, or other devices. Either or both of control panels 42b or 42c may also include a display for displaying information regarding patient support apparatus 20, and such a display may be a touchscreen in some embodiments. Alternatively, any one or more of control panels 42a-c may omit a touchscreen display and instead include only dedicated controls 72, or some other form of non-display controls.

The mechanical construction of those aspects of patient support apparatus 20 not explicitly described herein may be the same as, or nearly the same as, the mechanical construction of the Model FL27 InTouch Critical Care bed manufactured and sold by Stryker Corporation of Kalamazoo, Mich. This mechanical construction is described in greater detail in the Stryker Maintenance Manual for the Model FL27 InTouch Critical Care Bed (Version 2.4; 2131-409-002 REV B), published by Stryker Corporation of Kalamazoo, Mich., the complete disclosure of which is incorporated herein by reference. It will be understood by those skilled in the art that those aspects of patient support apparatus 20 not explicitly described herein can alternatively be designed with other types of mechanical constructions, such as, but not limited to, those described in commonly assigned, U.S. Pat. No. 7,690,059 issued to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The mechanical construction of those aspects of patient support apparatus 20 not explicitly described herein may also take on forms different from what is disclosed in the aforementioned references.

Figure 2:
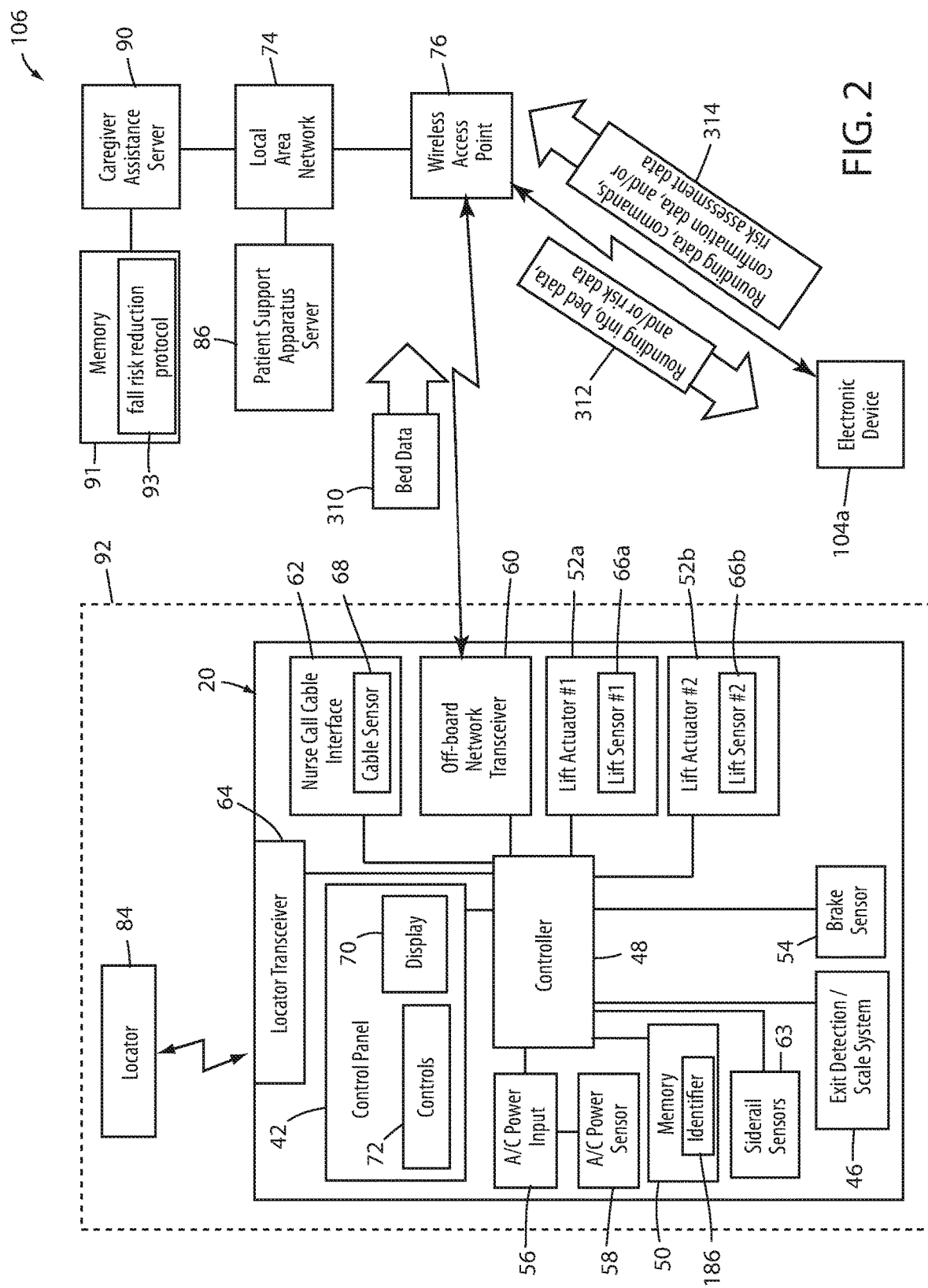
FIG. 2 is a block diagram of a first embodiment of the caregiver assistance system of the present disclosure showing a detailed set of components of the patient support apparatus of FIG. 1, as well as a portion of a local area network in which the patient support apparatus is in communication.

FIG. 2 illustrates a first embodiment of a caregiver assistance system 106 according to the present disclosure. Caregiver assistance system 106 includes patient support apparatus 20 in communication with a caregiver assistance server 90, and one or more electronic devices 104 that are adapted to communicate with caregiver assistance server 90. Caregiver assistance system 106 may also include a conventional patient support apparatus server 86 that is separate from caregiver assistance server 90, or the functionality of caregiver assistance server 90 may be modified to include the functionality of patient support apparatus server 86, thereby allowing patient support apparatus server 86 to be omitted. As will be discussed in greater detail below with respect to FIG. 4, caregiver assistance system 106 communicates with a plurality of conventional servers on a local area network 74 of the healthcare facility and uses those communications to obtain some of the information it needs to perform its caregiver assistance functions.

FIG. 2 illustrates in greater detail some of the internal components of patient support apparatus 20. As shown therein, patient support apparatus 20 includes a controller 48, a memory 50, a first lift actuator 52a, a second lift actuator 52b, a brake sensor 54, an scale/exit detection system 46, an Alternating Current (A/C) power input 56, an NC power sensor 58, one or more control panels 42, an off-board network transceiver 60, a nurse call cable interface 62, a plurality of siderail sensors 63, and a location transceiver 64. Additionally, patient support apparatus 20 includes a first lift sensor 66a, a second lift sensor 66b, a cable sensor 68, display 70, and one or more controls 72 incorporated into one or more of the control panels 42. It will be understood by those skilled in the art that patient support apparatus 20 may be modified to include additional components not shown in FIG. 2, as well modified to include fewer components from what is shown in FIG. 2.

Controller 48 (FIG. 2) is constructed of any electrical component, or group of electrical components, that are capable of carrying out the functions described herein. In many embodiments, controller 48 is a conventional microcontroller, or group of conventional microcontrollers, although not all such embodiments need include a microcontroller. In general, controller 48 includes any one or more microprocessors, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units as part of an embedded network. When implemented to include an embedded network, the embedded network may include multiple nodes that communicate using one or more of the following: a Controller Area Network (CAN); a Local Interconnect Network (LIN); an I-squared-C serial communications bus; a serial peripheral interface (SPI) communications bus; any of RS-232, RS-422, and/or RS-485 communication interfaces; a LonWorks network, and/or an Ethernet. The instructions followed by controller 48 in carrying out the functions described herein, as well as the data necessary for carrying out these functions, are stored in memory 50, and/or in one or more other memories accessible to the one or more microprocessors, microcontrollers, or other programmable components of controller 48. Memory 50 also includes a unique identifier 186 that uniquely identifies the particular patient support apparatus into which it is incorporated, such as, but not limited to, a serial number.

When controller 48 is implemented to communicate using an on-board Ethernet, the on-board Ethernet may be designed in accordance with any of the Ethernet-carrying patient support apparatuses disclosed in commonly assigned U.S. patent application Ser. No. 14/622,221 filed Feb. 13, 2015, by inventors Krishna Bhimavarapu et al. and entitled COMMUNICATION METHODS FOR PATIENT HANDLING DEVICES, the complete disclosure of which is incorporated herein by reference. In some embodiments, controller 48 may be implemented to include multiple nodes that communicate with each other utilizing different communication protocols. In such embodiments, controller 48 may be implemented in accordance with any of the embodiments disclosed in commonly assigned U.S. patent application Ser. No. 15/903,477 filed Feb. 23, 2018, by inventors Krishna Bhimavarapu et al. and entitled PATIENT CARE DEVICES WITH ON-BOARD NETWORK COMMUNICATION, the complete disclosure of which is incorporated herein by reference.

First and second lift actuators 52a and 52b (FIG. 2) are components of lifts 26 and are configured to raise and lower litter frame 28 with respect to base 22. A first one of lift actuators 52a powers a first one of the lifts 26 positioned adjacent a head end of patient support apparatus 20 and a second one of lift actuators 52b powers a second one of the lifts 26 positioned adjacent a foot end of patient support apparatus 20. Lift actuators 52a and 52b may be conventional linear actuators having electric motors therein that, when driven, expand or contract the length of the linear actuator, thereby moving the litter frame upward or downward and changing its height H (FIG. 1) relative to the floor.

Each lift actuator 52a and 52b includes a corresponding lift sensor 66a and 66b, respectively. Each of the sensors 66a, 66b detects a position and/or angle of its associated actuator 52a, 52b and feeds the sensed position/angle to controller 48. Controller 48 uses the outputs from sensors 66 as inputs into a closed-loop feedback system for controlling the motion of the actuators 52a, 52b and the litter deck. Controller 48 also uses the outputs from sensors 66a, 66b to determine the height H of litter frame 28 above the floor. In some embodiments, actuators 52 are constructed in any of the same manners as the actuators 34 disclosed in commonly assigned U.S. patent application Ser. No. 15/449,277 filed Mar. 3, 2017, by inventors Anish Paul et al. and entitled PATIENT SUPPORT APPARATUS WITH ACTUATOR FEEDBACK, the complete disclosure of which is incorporated herein by reference. In such embodiments, sensors 66a and 66b may be constructed to include any of the encoders and/or switch sensors disclosed in the aforementioned '277 application.

Scale/exit detection system 46 is configured to determine a weight of a patient positioned on support deck 30 and/or when the patient is moving and is likely to exit patient support apparatus 20. The particular structural details of the exit detection system can vary widely. In some embodiments, scale/exit detection system 46 includes a plurality of load cells arranged to detect the weight exerted on litter frame 28. By summing the outputs from each of the load cells, the total weight of the patient is determined (after subtracting the tare weight). Further, by using the known position of each of the load cells, controller 48 determines a center of gravity of the patient and monitors the center of gravity for movement beyond one or more thresholds. One method of computing the patient's center of gravity from the output of such load cells is described in more detail in commonly assigned U.S. Pat. No. 5,276,432 issued to Travis and entitled PATIENT EXIT DETECTION MECHANISM FOR HOSPITAL BED, the complete disclosure of which is incorporated herein by reference. Other methods for determining a patient's weight and/or the weight of non-patient objects supported on litter frame 28 are disclosed in commonly assigned U.S. patent application Ser. No. 14/776,842, filed Sep. 15, 2015, by inventors Michael Hayes et al. and entitled PATIENT SUPPORT APPARATUS WITH PATIENT INFORMATION SENSORS, and commonly assigned U.S. patent application Ser. No. 14/873,734 filed Oct. 2, 2015, by inventors Marko Kostic et al. and entitled PATIENT SUPPORT APPARATUSES WITH MOTION MONITORING, the complete disclosures of both of which are incorporated herein by reference. Other systems for determining a patient's weight and/or detecting a patient's exit from patient support apparatus 20 may alternatively be used.

Controller 48 communicates with network transceiver 60 (FIG. 2) which, in at least one embodiment, is a Wi-Fi radio communication module configured to wirelessly communicate with wireless access points 76 of local area network 74. In such embodiments, network transceiver 60 may operate in accordance with any of the various IEEE 802.11 standards (e.g. 802.11b, 802.11n, 802.11g, 802.11ac, 802.11ah, etc.). In other embodiments, network transceiver 60 may include, either additionally or in lieu of the Wi-Fi radio and communication module, a wired port for connecting a network wire to patient support apparatus 20. In some such embodiments, the wired port accepts a category 5e cable (Cat-5e), a category 6 or 6a (Cat-6 or Cat-6a), a category 7 (Cat-7) cable, or some similar network cable, and transceiver 60 is an Ethernet transceiver. In still other embodiments, network transceiver 60 may be constructed to include the functionality of the communication modules 56 disclosed in commonly assigned U.S. patent application Ser. No. 15/831,466 filed Dec. 5, 2017, by inventor Michael Hayes et al. and entitled NETWORK COMMUNICATION FOR PATIENT SUPPORT APPARATUSES, the complete disclosure of which is incorporated herein by reference.

Regardless of the specific structure included with network transceiver 60, controller 48 is able to communicate with the local area network 74 (FIG. 2) of a healthcare facility in which the patient support apparatus is positioned. When network transceiver 60 is a wireless transceiver, it communicates with local area network 74 via one or more wireless access points 76. When network transceiver 60 is a wired transceiver, it communicates directly via a cable coupled between patient support apparatus 20 and a network outlet positioned within the room of the healthcare facility in which patient support apparatus 20 is positioned. As will be discussed in greater detail below with respect to FIG. 4, local area network 74 includes a plurality of servers that are utilized in different manners by the caregiver assistance system disclosed herein, and patient support apparatus 20 communicates with one or more of those servers via transceiver 60 as part of the caregiver assistance system.

Figure 4:
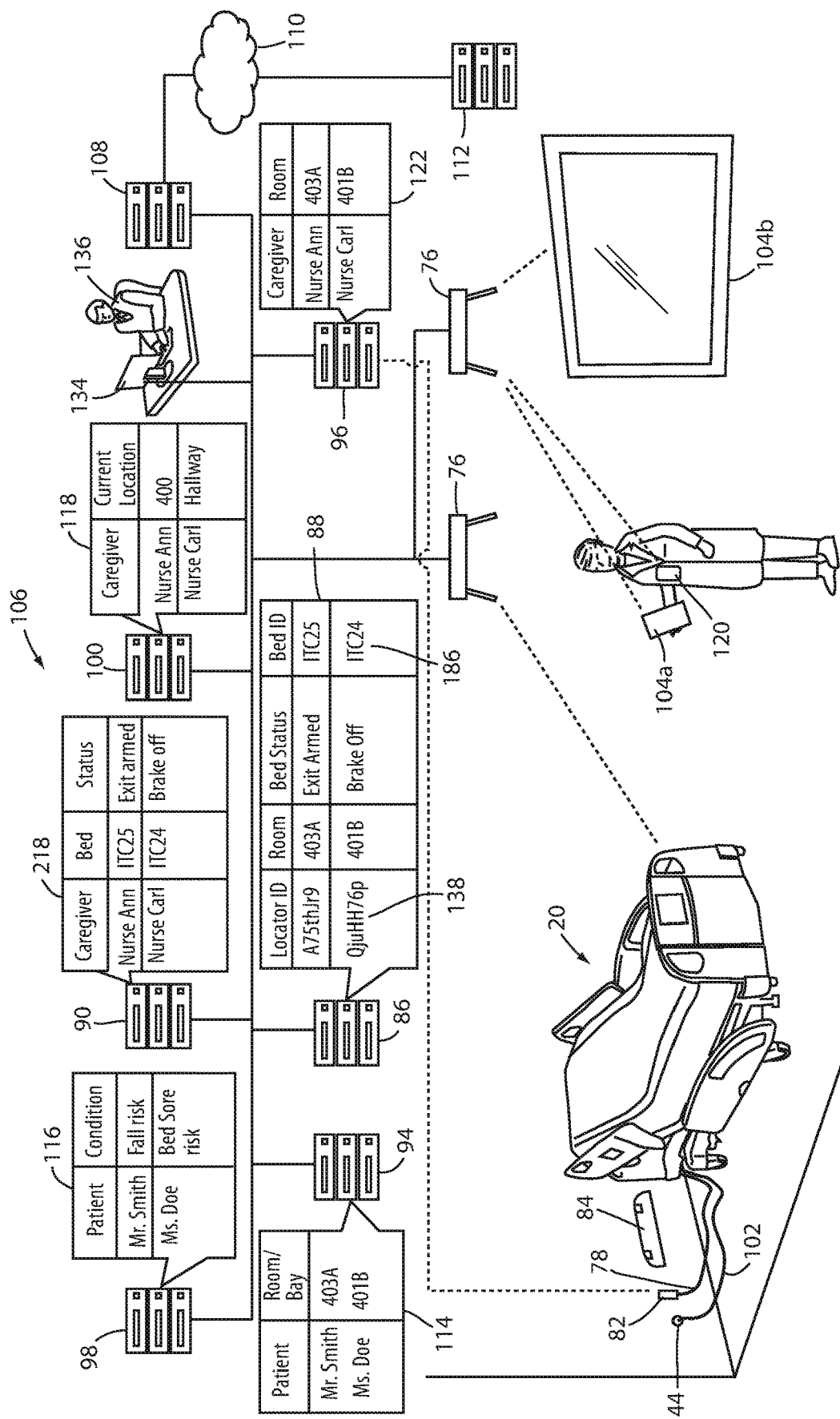
FIG. 4 is a block diagram of the caregiver assistance system shown integrated into a local area network of a healthcare facility.

Nurse call cable interface 62 is an interface adapted to couple to one end of a nurse call cable 78 (FIG. 4). The other end of the nurse call cable 78 couples to a nurse call outlet 82 (FIG. 4) that is typically built into each headwall of each of the patient rooms within a healthcare facility. In many embodiments, nurse call outlet 82 is a 37 pin outlet that cable 78 couples to, thereby enabling patient support apparatus 20 to communicate directly with a conventional nurse call system 80. In some embodiments, nurse call interface 62 is constructed in accordance with any of the cable interfaces 92 disclosed in commonly assigned U.S. patent application Ser. No. 15/945,437 filed Apr. 4, 2018, by inventors Krishna Bhimavarapu et al. and entitled PATIENT SUPPORT APPARATUSES WITH RECONFIGURABLE COMMUNICATION, the complete disclosure of which is incorporated herein by reference. In other embodiments, nurse call cable interface 62 may be replaced with a wireless nurse call communication system that wirelessly communicates with nurse call outlet 82. For example, in some embodiments, nurse call cable interface 62 is replaced with a radio module, such as the radio module 60 disclosed in commonly assigned U.S. patent application Ser. No. 14/819,844 filed Aug. 6, 2015, by inventors Krishna Bhimavarapu et al. and entitled PATIENT SUPPORT APPARATUSES WITH WIRELESS HEADWALL COMMUNICATION, the complete disclosure of which is incorporated herein by reference. In such wireless headwall embodiments, a headwall module, such as headwall module 38 disclosed in the aforementioned '844 application, is included and coupled to nurse call outlet 82. Still other types of wireless communication between the patient support apparatus and nurse call outlet 82 may be implemented.

Siderail sensors 63, which may be conventional siderail sensors, are configured to detect when the siderails 36 are in a raised or lowered position. In most embodiments, a single siderail sensor 63 is included for each of the siderails 36. Therefore, in the embodiment of FIG. 1, patient support apparatus 20 includes four siderail sensors 63, one for detecting the position of each of the four siderails 36. In alternative embodiments, more than one siderail sensor 63 may be included for each siderail 36, such as a first siderail sensor 63 that detects when the siderail is raised and/or locked in its raised position, and a second siderail sensor 63 that detects when the siderail 36 is in its lower position, and/or locked in its lowered position. In general, any switch or other type of sensor that is able to detect when the respective siderail 36 is in its raised and/or locked orientation can be used with patient support apparatus 20. The outputs of siderail sensors 63 are fed to controller 48 and are periodically sent to caregiver assistance server 90 as part of the patient support apparatus status updates that are discussed in greater detail below. Further, as will also be discussed in greater detail below, the position of one or more siderails 36 is monitored for compliance with a desired state, such as, but not limited to, a desired state defined by a fall risk reduction protocol 93 discussed in more detail below.

Location transceiver 64 (FIG. 2) is adapted to detect a wireless signal emitted from a nearby location beacon 84 (FIG. 4) that is positioned at a fixed and known location within the healthcare facility. Although FIG. 4 only illustrates a single one of these location beacons 84, it will be understood that a particular healthcare facility includes many of these location beacons 84 mounted throughout the healthcare facility. Each location beacon 84 broadcasts a wireless, short range signal that contains a unique identifier. The short range signal, in some embodiments, is broadcast via an infrared transmitter and is only detectable by receivers (e.g. location transceivers 64) that are positioned within several feet of the location beacon 84. Consequently, location transceivers 64, which are adapted to detect the signals transmitted from location beacons 84, are only able to detect these signals when patient support apparatuses 20 are positioned adjacent (e.g. within several feet) of one of these location beacons 84. If/when location transceiver 64 is able to detect the unique signal from a particular location beacon 84, the corresponding patient support apparatus 20 can therefore be concluded to be currently positioned adjacent that particular location beacon 84. This allows the current location of the patient support apparatus 20 to be identified. In some healthcare facilities, one or more of the patient rooms may not be completely private rooms, but instead may be shared with one or more other patients. In such situations, it is typical to mount two or more location beacons 84 within such a room—one on the headwall at the bay where the first patient support apparatus 20 normally resides and the other on the headwall at the bay where the second patient support apparatus 20 normally resides (and still more if the room is shared by more than two patients).

When location transceiver 64 receives a signal from an adjacent location beacon 84, controller 48 forwards the received signal, including the unique ID of the beacon 84, to a patient support apparatus server 86 (FIG. 2) which is sometimes alternately referred to herein as a bed server 86. Patient support apparatus server 86 includes a location table 88 (FIG. 4), or has access to such a table 88, that correlates beacon IDs to locations within the healthcare facility. Patient support apparatus server 86 is thereby able to determine the location of each patient support apparatus 20 within the healthcare facility (at least all of those that are positioned adjacent a location beacon 84).

In some embodiments, location beacons 84 (FIG. 2) function both as locators and as wireless links to the nurse call outlet 82 integrated into the adjacent headwall. When equipped with this dual function, patient support apparatuses 20 may omit the nurse call cable interface 62, yet still be able to communicate with the nurse call system server 62b. In the illustrated embodiment of FIG. 4, however, patient support apparatus 20 includes a nurse call cable 78 that communicatively couples the patient support apparatus 20 to nurse call outlet 82, thereby enabling the patient support apparatus 20 to communicate directly with the nurse call system 80. Further details about the function of location beacons 84, whether operating solely as locators or both as locators and wireless portals to the nurse call system outlets 82, may be found in any of the following commonly assigned U.S. patent references: U.S. Pat. No. 8,102,254 issued Jan. 24, 2012 to Becker et al. and entitled LOCATION DETECTION SYSTEM FOR A PATIENT HANDLING DEVICE; patent application Ser. No. 14/819,844 filed Aug. 6, 2015, by inventors Krishna Bhimavarapu et al. and entitled PATIENT SUPPORT APPARATUSES WITH WIRELESS HEADWALL COMMUNICATION; patent application Ser. No. 62/600,000 filed Dec. 18, 2017, by inventor Alex Bodurka, and entitled SMART HOSPITAL HEADWALL SYSTEM; and patent application Ser. No. 62/598,787 filed Dec. 14, 2017, by inventors Alex Bodurka et al. and entitled HOSPITAL HEADWALL COMMUNICATION SYSTEM, the complete disclosures of all of which are incorporated herein by reference.

Controller 48 of patient support apparatus 20 (FIG. 2) communicates with NC power sensor 58, which informs controller 48 whether or not an NC power cable 102 (FIG. 4) is coupled between patient support apparatus 20 and a conventional NC power outlet 44. In other words, NC power sensor 58 lets controller 48 know whether patient support apparatus 20 is receiving electrical power from an off-board power supply (e.g. power outlet 44). In some cases, patient support apparatus 20 includes one or more batteries that are able to power patient support apparatus 20, including controller 48, when patient support apparatus 20 is not coupled to a source of electrical power. As will be discussed more below, the status of the NC power cord 102 (e.g. whether patient support apparatus 20 is operating on battery power or on power from an NC outlet) is communicated from A/C power sensor 58 to controller 48, which then forwards that status via network transceiver 60 to patient support apparatus server 86 and/or to caregiver assistance server 90.

Controller 48 also communicates with brake sensor 54 (FIG. 2). Brake sensor 54 informs controller 48 whether or not a brake has been applied on patient support apparatus 20. When the brake is applied, one or more of wheels 24 are braked to resist rotation. When the brake is not applied, wheels 24 are free to rotate. As with the data from the NC power cord 58, the data from the brake sensor 54 is forwarded by controller 48 to patient support apparatus server 86 and/or to caregiver assistance server 90, via network transceiver 60. Caregiver assistance server 90 shares this information with caregivers via one or more electronic devices that are in communication with server 90, as will be discussed in greater detail below.

Each of the control panels 42 includes one or more controls 72 that are used to control various functions of the patient support apparatus 20 (FIG. 2). For example, one or more of the control panels 42 includes a motion control 72 for controlling movement of the lift actuators 52a and 52b. Additional controls 72 may be provided for activating and deactivating the brake for wheels 24, arming and disarming exit detection function of scale/exit detection system 46, taking a weight reading of the patient using the scale function of scale/exit detection system 46, activating and deactivating a propulsion system (if included), and communicating with one or more servers on local area network 74. It will be understood that in some embodiments, one or more of controls 72 may be integrated into a touchscreen display, such as display 70. In such embodiments, one or more of the controls may only appear when the user navigates to specific screens displayed on the touchscreen.

Patient support apparatus 20 communicates with the caregiver assistance server 90 of local area network 74 (FIG. 2). Caregiver assistance server 90 is adapted to assist the caregivers in performing a plurality of tasks. In general, caregiver assistance server 90 includes software that, when executed, assists the caregivers in ensuring that the patient support apparatuses 20 are maintained in a desirable state, assists the caregiver in performing their rounding tasks, assists the caregivers in performing fall and/or skin assessments, assists the caregivers with setting reminders and receiving notifications of the reminders, as well as assists the caregivers with receiving alerts and/or status information about the patients under their care while the caregivers go about their duties.

Caregiver assistance server 90 includes a memory 91 storing various data used by server 90, such as, but not limited to, a caregiver assistance application 124 and a fall risk reduction protocol 93. Memory 91 may be physically included within server 90 and/or it may be distributed across one or more other physical locations that are accessible to server 90. Caregiver assistance application 124 uses the fall risk reduction protocol 93 when application 124 executes the patient fall risk reduction algorithm 143, as will be discussed in greater detail below. In general, patient fall risk reduction algorithm 143 enables a caregiver to utilize one or more of the electronic devices 104 to assess the fall risk of a patient and to subsequently ensure that the patient support apparatus 20 is in a state specified by the healthcare facility for that patient's particular fall risk. Fall risk reduction protocol 93 specifies the desired state of patient support apparatus 20 for one or more fall risk levels.

Figure 3:
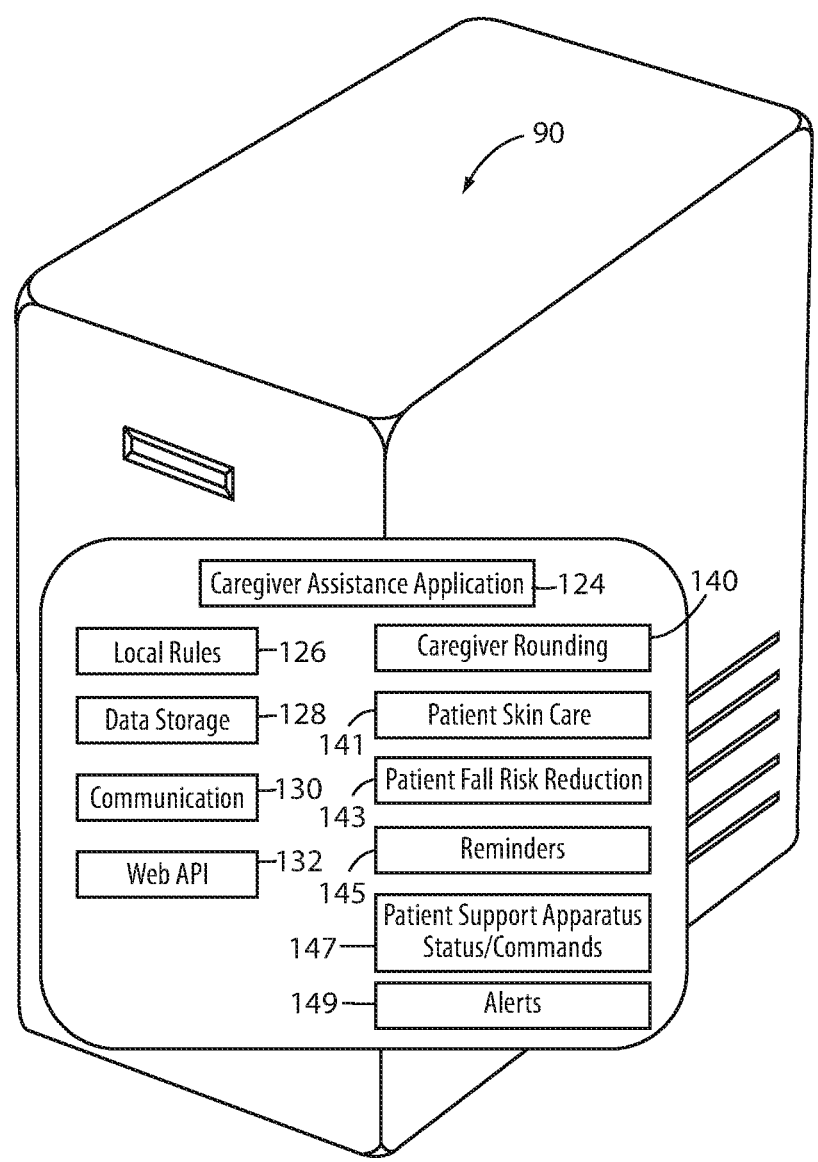
FIG. 3 is a block diagram of a set of components of a caregiver assistance application executed on a server of the caregiver assistance system of FIG. 2.

FIG. 3 illustrates in greater detail some of the specific functionality and components of caregiver assistance server 90. Caregiver assistance server 90 is adapted to execute a caregiver assistance application 124 that performs a plurality of algorithms and that utilizes a plurality of components. The algorithms includes a caregiver rounding algorithm 140, a patient skin care algorithm 141, a patient fall risk reduction algorithm 143, a reminder algorithm 145, a status/command algorithm 147, and an alerting algorithm 149.

Caregiver rounding algorithm 140 assists a caregiver in performing his or her rounding duties, as well as assisting the caregiver to ensure that patient support apparatuses 20 are properly configured in accordance with the policies of the particular healthcare facility that employs the caregivers and operates the patient support apparatuses 20. In general, caregiver rounding algorithm 140 allows a caregiver to document his or her individual rounding actions while simultaneously reminding the caregiver of any actions that need to be taken to configure the patient support apparatus 20 properly. Such patient support apparatus configurations include, but are not limited to, setting a brake, moving the litter frame to its lowest height (or within a specified range of its lowest height), positioning the siderails in a correct position, arming the exit detection system, plugging in the nurse call cable, plugging in the NC power cable, and/or arming a patient support apparatus monitoring system.

Patient skin care algorithm 141 assists the caregiver in assessing a particular patient's risk of developing bed sores and/or in managing the care of a patient's existing bed sores. Fall risk reduction algorithm 143 assists the caregiver in assessing the fall risk of a particular patient and/or in ensuring that patient support apparatus 20 is placed in a desired state for reducing the risk of a patient falling. Reminder algorithm 145 assists the caregiver by keeping track of any or all tasks that the caregiver is to complete that have time deadlines, including issuing reminders to the caregiver of when those tasks are due and/or are approaching their deadlines. Status/command algorithm 147 functions to provide the caregivers with up-to-date information of the status of each of the patient support apparatuses 20 having a patient to which that caregiver is assigned, as well as to allow the caregiver to remotely control one or more aspects of those patient support apparatuses 20. Alerting algorithm 149 provides alerts to caregivers when a status of a patient support apparatus 20 is changed to an out-of-compliance state, when a reminder deadline approaches or is reach, and/or whenever any information from any of the other algorithms 140, 141, 143, 145, and/or 147 yields information to which the caregivers should be alerted.

Further details of one embodiment of a patient skin care algorithm 141 (FIG. 3) that may be utilized with the system 106 of the present disclosure are found in commonly assigned U.S. provisional patent application Ser. No. 62/826,195, filed Mar. 29, 2019, by inventors Thomas Durlach et al. and entitled SYSTEM FOR MANAGING PATIENT SUPPORT APPARATUSES AND BED SORE RISKS, the complete disclosure of which is incorporated herein by reference. Other skin care algorithms may be executed by caregiver assistance application 124 without departing from the spirit of the present disclosure. Further details of various embodiments of patient fall risk reduction algorithm 143 are discussed below with respect to FIGS. 18-27. Further details regarding a suitable reminder algorithm 145, status/command algorithm 147, and an alerting algorithm 149 are also provided below.

The different components of caregiver assistance application 124 include a set of local rules 126, a data repository 128, a communication interface 130, and a web Application Programming Interface 132 (FIG. 3). The set of local rules 126 is initially defined prior to the installation of caregiver assistance application 124 within a particular healthcare facility, in at least some embodiments. In other embodiments, the set of local rules 126 is defined during or after installation of caregiver assistance application 124. In all embodiments discussed herein, however, local rules 126 are modifiable by authorized personnel from the healthcare facility. Such modifications are made by way of one or more computers 134 that are in communication with local area network 74 (FIG. 4). An authorized individual 136 (FIG. 4) utilizes computer 134 to communicate with caregiver assistance application 124 and add, delete, or modify one or more of the local rules 126.

Local rules 126 (FIG. 3) include, but are not limited to, the following: rules indicating how frequently caregivers are to perform their rounding duties (e.g. once every two hours, once every three hours, etc.); rules indicating what state patient support apparatuses 20 are to be placed in (e.g. one or more fall risk reduction protocols and/or skin care protocols, etc.); rules specifying who is to be notified, and when, if a rounding duty is not performed within the desired time period; rules specifying who is to be notified, and when, if a patient support apparatuses is not placed in the desired state and/or is moved out of the desired state; rules specifying how such notifications are to be communicated (e.g. email, phone call, texts, etc.); rules specifying what personnel within the healthcare facility are authorized to view what data using caregiver assistance application 124; and rules specifying if and/or how rounding duties are to be verified and/or documented in the EMR server 98. Both the rules for caregiver assistance frequency and the desired states of the patient support apparatuses 20 may be configured by authorized individuals 136 to vary based upon one or more factors. For example, both the caregiver assistance frequency and desired states of patient support apparatuses may vary for different wings of the healthcare facility, different units of the healthcare facility, different times of day and/or different shifts, different models of patient support apparatuses, different patient health conditions, different patient treatments, different data stored in the EMR server 98, etc.

Local rules 126 (FIG. 3) also include additional administrative data that is stored on caregiver assistance server 90, or stored in a memory otherwise accessible to caregiver assistance application 124. Such administrative data includes, but is not limited to, the IP address, or other network address, of each of the servers with which caregiver assistance application 124 is to communicate (e.g. EMR server 98, ADT server 94, patient support apparatus server 86, RTLS server 100, and nurse call server 96), and/or the IP addresses or other configuration data necessary for caregiver assistance application 124 to communicate with one or more middleware software applications that act as gateways to one or more of these servers. The administrative data also may also include the email addresses, passwords, phone numbers, user names, access levels, and other information about those hospital personnel who have been authorized to use caregiver assistance application 124. The email address and/or phone numbers are used in some embodiments of the alerting algorithm 149 in order for caregiver assistance application 124 to make contact with mobile electronic devices 104*a* (FIG. 4) carried by the caregivers when there is an alert, or other information to which the caregiver's attention is desirably directed.

Data repository 128 (FIG. 3) stores data that is received by caregiver assistance application 124 during the course of its operation. This data includes patient support apparatus status data sent from patient support apparatuses 20 (via patient support apparatus server 86 in some embodiments, and directly in other embodiments), alert data (e.g. when alerts occurred, causes, remedies, notifications, etc.), rounding completion/incompletion data, verification data verifying caregiver assistance (discussed more below), patient data from skin care and fall risk reduction algorithms 141 and 143, and other data.

Communication interface 130 (FIG. 3) controls the communications between caregiver assistance application 124 and the electronic devices 104 with which it is in communication. Communication interface 130 also controls the communications between caregiver assistance application 124 and the servers with which it is in communication. All of these communications, in at least one embodiment, are carried out using conventional Internet packet routing. That is, patient support apparatuses 20 send data in packets that have an IP addresses corresponding to patient support apparatus server 86 and/or caregiver assistance server 90, and servers 86 and/or 90 send message packets back to patient support apparatuses 20 that include an IP address corresponding to the particular patient support apparatus(es) 20 to which the messages are intended. In some embodiments, each patient support apparatus 20 includes a static IP address that is stored on the patient support apparatus 20, while in other embodiments, the patient support apparatuses 20 consult a local Dynamic Host Configuration Protocol (DHCP) server (not shown) on local area network 74 and the DHCP server assigns a network address to the patient support apparatus.

Web API 132 (FIG. 3) provides a portal for authorized software applications and/or servers to access the data of caregiver assistance application 124. In some embodiments, electronic devices 104 communicate with caregiver assistance application 124 via the web API 132. In other embodiments, electronic devices 104 utilize a web browser built therein that access one or more Uniform Resource Locators (URLs) that direct the web browser to caregiver assistance application 124. In still other embodiments, web API 132 may be utilized for carrying out additional communications with any of the servers on network 74 and/or for communicating with other software applications that are unrelated to caregiver assistance application 124.

In general, caregiver rounding algorithm 140, status/command algorithm 147, and alerting algorithm 149 of caregiver assistance application 124 performs the following functions: gather data from patient support apparatuses 20 about their current states; communicate the patient support apparatus data to electronic devices 104 that are remote from caregiver assistance server 90; cause the electronic devices 104 to display the patient support apparatus status data thereon; cause the electronic devices 104 to display reminders and/or other information on their displays to assist caregivers in performing their rounding duties; receive rounding data that is input into electronic devices 104 by caregivers during or after the performance of their rounding duties; communicate alerts to the caregivers if the patient support apparatus status data indicates the patient support apparatus 20 is not in a desired state; forward patient support apparatus commands received from caregivers (via electronic devices 104) to patient support apparatuses 20; receive verification data from electronic devices 104 and/or patient support apparatuses 20 verifying the caregivers' presence adjacent the patient support apparatus 20 when performing the rounding tasks; and document to an Electronic Medical Record server 98 (FIG. 4) the successful completion of the rounding tasks, as well as the current state of the patient support apparatus status data at the time of completion of the rounding task. It will be understood that, in some embodiments, caregiver assistance application 124 may be modified such that one or more of these functions are modified, supplemented, and/or omitted.

Patient support apparatus 20 is shown in FIG. 2 positioned in a room 92 of a representative example of a healthcare facility. FIG. 2 also depicts patient support apparatus 20 in communication with local area network 74 of the healthcare facility. It will be understood that the precise structure and contents of the local area network 74 will vary from healthcare facility to healthcare facility. FIG. 4 illustrates in greater detail the contents of a common hospital's local area network 74, along with caregiver assistance server 90 and other components of caregiver assistance system 106.

As shown in FIG. 4, local area network 74 includes a plurality of servers, including a conventional Admission, Discharge, and Tracking (ADT) server 94, a conventional nurse call system server 96, a conventional Electronic Medical Records server 98, a conventional real time location system (RTLS) server 100, and a plurality of conventional wireless access points 76. Local area network 74 also includes caregiver assistance server 90 that, together with one or more patient support apparatuses 20 and one or more electronic devices (e.g. mobile electronic devices 104*a* or stationary electronic devices 104*b*) implement one embodiment of the caregiver assistance system 106 according to the present disclosure. Still further, network 74 includes a conventional Internet gateway 108 that couples local area network 74 to the Internet 110, thereby enabling the servers and/or patient support apparatuses 20 to communicate with computers outside of the healthcare facility, such as, but not limited to, a geographically remote server 112. In some embodiments, all or some of the functions of caregiver assistance server 90 are carried out by geographically remote server 112, while in other embodiments caregiver assistance server 90 is configured to implement all of its functions without accessing geographically remote server 112.

ADT server 94 stores patient information, including the identity of patients and the corresponding rooms 92 and/or bays within rooms to which the patients are assigned. That is, ADT server 94 includes a patient-room assignment table 114, or functional equivalent to such a table. The patient-room assignment table correlates rooms, as well as bays within multi-patient rooms, to the names of individual patients within the healthcare facility. The patient's names are entered into the ADT server 94 by one or more healthcare facility staff whenever a patient checks into the healthcare facility and the patient is assigned to a particular room within the healthcare facility. If and/or when a patient is transferred to a different room and/or discharged from the healthcare facility, the staff of the healthcare facility update ADT server 94. ADT server therefore maintains an up-to-date table 114 that correlates patient names with their assigned rooms.

EMR server 98 (FIG. 4) stores individual patient records. Such patient records identify a patient by name and the medical information associated with that patient. Such medical information may include all of the medical information generated from the patient's current stay in the healthcare facility as well as medical information from previous visits. EMR table 116 shows an abbreviated example of two types of medical information entries that are commonly found within a patient's medical records: a fall risk entry indicating whether the patient is a fall risk, and a bed sore risk entry indicating whether the patient is at risk for developing bed sores. Although FIG. 4 shows the data for these entries to be expressed as text, it will be understood that this data may be stored within a medical record in numeric format. For example, the fall risk data may be stored as a numeric value generated from a conventional fall risk assessment tool, such as, but not limited to, the Morse fall risk scale or the Hester-Davis fall risk scale. Similarly, the bed sore data may be stored as a numeric value generated from a conventional bed sore risk assessment tool, such as, but not limited to, the Braden scale. As noted, EMR server 98 includes far more additional information in the medical records of each patient than what is shown in table 116 of FIG. 4, and some of that additional data, such as rounding data, is discussed in more detail below. It will be understood that the term "EMR server," as used herein, also includes Electronic Health Records servers, or EHR servers for short, and that the present disclosure does not distinguish between electronic medical records and electronic health records.

RTLS server 100 (FIG. 4) is a conventional server that may be present within a given healthcare facility. When present, RTLS server 100 keeps track of the current location of people and equipment within the healthcare facility. In many instances, the RTLS server keeps track of the current location of one or more tags 120 (FIG. 4) that are worn by personnel and/or that are attached to equipment. Such tags 120 may be RF ID tags, or other types of tags. RTLS table 118 provides an example of the type of location data that RTLS server 100 may contain with respect to caregivers. As shown therein, table 118 shows the current location of two caregivers, one by room number (e.g. room 400) and another by general location (e.g. "hallway"). Other types of location data may be included. Further, as noted, some healthcare facilities may not include such an RTLS server 100 and caregiver assistance system 106 is able to fully function without such a server.

Nurse call server 96 is shown in FIG. 4 to include a caregiver assignment table 122 that matches caregivers to specific rooms and/or bays within the healthcare facility. Although table 122 only shows caregivers assigned to a single room, it will be understood that each caregiver is typically assigned to multiple rooms. In some nurse call systems 80, caregivers are assigned to specific patients, rather than to specific rooms. Caregiver assistance system 106 is configured to work with both types of nurse call systems 80. Caregiver assistance system 106 is also adapted to work with healthcare facilities that utilize a separate caregiver assignment server (not shown), rather than nurse call server 96, to assign caregivers to rooms and/or patients.

Regardless of whether caregiver assignment table 122 is stored within nurse call server 96 or some other server on network 74, nurse call system server 96 is configured to communicate with caregivers and patients. That is, whenever a patient on a patient support apparatus 20 presses, or otherwise activates, a nurse call, the nurse call signals pass through nurse call cable 78 to nurse call outlet 82. Nurse call outlet 82 is coupled via wire to nurse call server 96 and/or to another structure of nurse call system 80 that then routes the call to the appropriate nurse. The nurse is thereby able to communicate with the patient from a remote location. In some nurse call systems 80, nurse call server 96 is also able to forward alerts and/or other communications to portable wireless devices carried by caregivers and/or to audio stations positioned within patient rooms 92. Such portable wireless devices are the same as mobile electronic devices 104a discussed herein, in at least one embodiment.

Local area network 74 may include additional structures not shown in FIG. 4, such as, but not limited to, one or more conventional work flow servers and/or charting servers that monitor and/or schedule patient-related tasks for particular caregivers, and/or one or more conventional communication servers that forward communications to particular individuals within the healthcare facility, such as via one or more portable devices (smart phones, pagers, beepers, laptops, etc.). The forwarded communications may include data and/or alerts that originate from patient support apparatuses 20 as well as data and/or alerts that originate from caregiver assistance server 90.

Wireless access points 76 are configured, in at least some embodiments, to operate in accordance with any one or more of the IEEE 802.11 standards (e.g. 802.11g, 802.11n, 802.11ah, etc.). As such, patient support apparatuses 20 and electronic devices 104a, 104b that are equipped with Wi-Fi capabilities, and that have the proper authorization credentials (e.g. password, SSID, etc.), can access local area network 74 and the servers hosted thereon. This allows patient support apparatus 20 to send messages to, and receive messages from, patient support apparatus server 86 and/or caregiver assistance server 90. This also allows electronic devices 104 to send messages to, and receive messages from, patient support apparatus server 86 and/or caregiver assistance server 90. As noted previously, alternatively, or additionally, patient support apparatuses 20 may include a wired port for coupling a wired cable (e.g. a Category 5, Category 5e, etc.) between the patient support apparatus 20 and one or more routers/gateways/switches, etc. of network 74, thereby allowing patient support apparatuses 20 to communicate via wired communications with servers 86 and/or 90.

In still other embodiments, one or more of the patient support apparatuses 20 are equipped with alternative wireless transceivers enabling them to communicate directly with patient support apparatus server 86 and/or caregiver assistance server 90 via an antenna and transceiver that is directly coupled to servers 86 and/or 90 and that is separate from LAN 74, thereby allowing patient support apparatuses 20 to bypass LAN 74 in their communications with servers 86 and/or 90. One example of patient support apparatuses equipped to communicate directly with a server on a healthcare facility's local area network without utilizing the LAN is disclosed in commonly assigned U.S. patent application Ser. No. 15/831,466 filed Dec. 5, 2017, by inventors Michael Hayes and entitled NETWORK COMMUNICATION FOR PATIENT SUPPORT APPARATUSES, the complete disclosure of which is incorporated herein by reference. In some embodiments, patient support apparatuses 20 include communication modules, such as the communication modules 66 disclosed in the aforementioned '466 application, and servers 86 and/or 90 are coupled directly to a receiver, such as the enterprise receiver 90 disclosed in the aforementioned '466 application. In such embodiments, patient support apparatuses 20 are able to both send and receive messages directly to and from servers 86 and/or 90 without utilizing access points 76 or any of the hardware of network 74 (other than servers 86 and/or 90).

Caregiver assistance server 90 constructs a table 218 (FIG. 4) that correlates specific caregivers with the patient support apparatuses 20 assigned to them. As shown in FIG. 4, table 218 correlates individual patient support apparatuses 20 and their current statuses to the specific caregivers who are assigned to those patient support apparatuses 20. Although not shown in FIG. 4, table 218 also may correlate caregivers and their patient support apparatuses 20 to specific rooms within the healthcare facility. In order to construct table 218, caregiver assistance application 124 receives the unique patient support apparatus identifiers 186, along with the current status of the patient support apparatuses 20 from patient support apparatus server 86. Caregiver assistance application 124 determines which caregivers are associated with each of these patient support apparatuses 20 based on the caregiver-to-room assignment data it receives from nurse call server 96 (i.e. the data of table 122) and the room-to-patient support apparatus data it receives from patient support apparatus server 86 (i.e. the data from table 88). Caregiver assistance server 90 is therefore supplied with sufficient data to know the current status of each patient support apparatus 20, the room in which each patient support apparatus 20 is assigned, the caregiver assigned to that room and/or patient support apparatus 20, the patient assigned to each patient support apparatus 20, and the fall risk and/or bed sore risk (if known) of each patient. Still further, in those embodiments where an RTLS server 100 is included, caregiver assistance server 90 is also supplied with sufficient data to know the current location of each caregiver.

Figure 5:
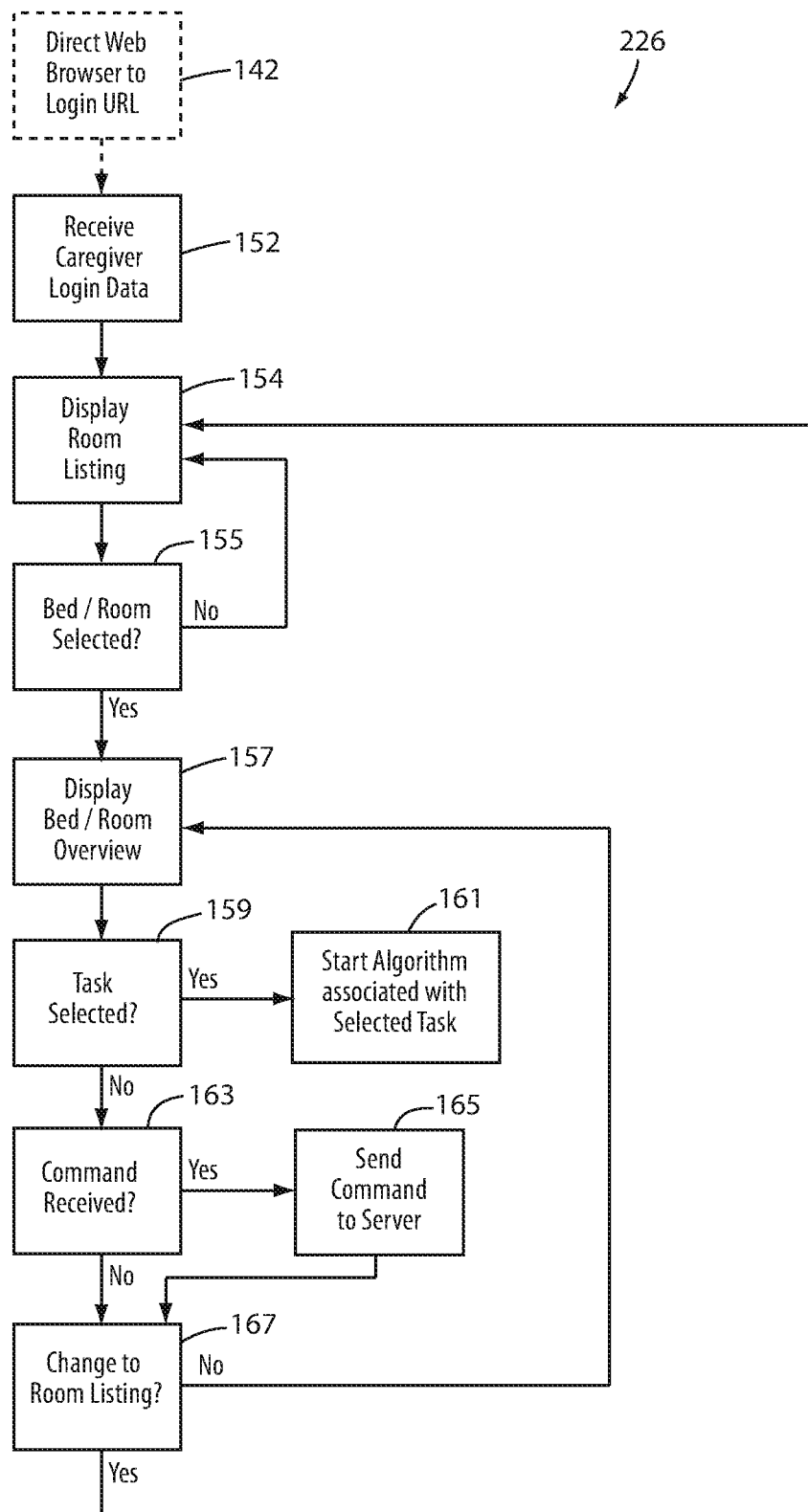
FIG. 5 is a flow diagram of a general algorithm executed by the caregiver assistance application of FIG. 3.

FIG. 5 illustrates a general algorithm 226 executed by caregiver assistance application 124 in at least one embodiment of the present disclosure. General algorithm 226 is carried out by the one or more processors of caregiver assistance server 90 when caregiver assistance server 90 is executing caregiver assistance application 124. General algorithm 226 begins at an initial access step 142 where a user accesses caregiver assistance application 124. Initial step 142 is illustrated in FIG. 5 as a window having dashed lines. The dashed lines are presented in order to indicate that step 142 is performed by a user, rather than caregiver assistance application 124 itself. The remaining steps of algorithm 226 are carried out by caregiver assistance application 124.

Initial step 142 is carried out by a user by manipulating one of the electronic devices 104 that are used in conjunction with caregiver assistance application 124. Caregiver assistance system 106 includes one or more electronic devices 104 that communicate with caregiver assistance server 90 and its caregiver assistance application 124. These electronic devices 104 utilize caregiver assistance application 124 to receive status data from patient support apparatuses 20 and to send and receive caregiver assistance data. In other words, caregiver assistance application 124 functions as an intermediary between the electronic devices 104 and the patient support apparatuses 20, as well as an intermediary between the electronic devices 104 and other servers, such as EMR server 98 and/or the nurse call server 96. Caregiver assistance application 124 also performs other functions, as described below.

Electronic devices 104 come in a variety of different forms. As shown in FIG. 4, some electronic devices 104a are mobile electronic devices intended to be carried by a user (e.g. caregiver) while other electronic devices 104b are stationary electronic devices that generally remain in one location. Mobile electronic devices 104a may take on different forms, such as, but not limited to, smart phones, tables, laptop computers, Computers on Wheels (COWs), and others. Stationary electronic devices 104b may also take on different forms, such as, but not limited to, televisions, displays, Personal Computers (PCs), and others. For purposes of the following written description, caregiver assistance system 106 will be described with reference to electronic devices 104 that access caregiver assistance system 106 via a conventional web browser. It will be understood, however, that in other embodiments, electronic devices 104 may be modified to execute a specialized software application that is downloaded to the electronic device 104 and that is tailored to be executed by the particular operating system of the electronic device (e.g. Android, iOS, Windows, etc.). The specialized software application is executed by the microcontroller(s) of the electronic device 104 and carries out the functions of caregiver assistance system 106.

In order for a caregiver associated with an electronic device 104 to access caregiver assistance system 106, the caregiver utilizes the web-browsing application contained within the electronic device 104 to go to a particular web page, or other URL, associated with caregiver assistance application 124. Any conventional web-browsing software may be used for this purpose, including, but not limited to, Microsoft's Bing or Internet Explorer web browsers, Google's Chrome web browser, Apple's Safari web browser, Mozilla's Firefox web browser, etc. The particular URL accessed with the web browser may vary for different healthcare facilities and can be customized by authorized IT personnel at the healthcare facility. In some embodiments, a domain name may be associated with caregiver assistance application 124 that is resolved by a local DNS server to the IP address of caregiver assistance server 90 (e.g. www.caregiver-assistance-app.com). In other embodiments, access to caregiver assistance system 106 may be achieved in other manners.

Figure 7:
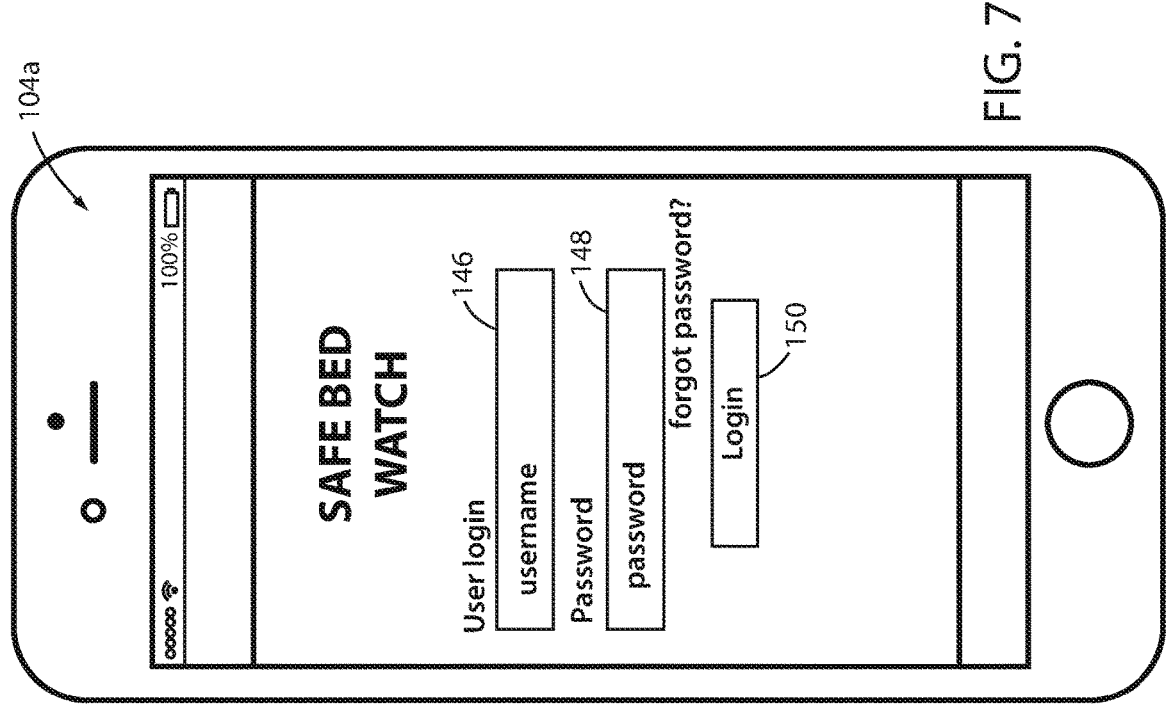
FIG. 7 is a plan view of a portable electronic device usable with the caregiver assistance system of FIG. 2 wherein the portable electronic device is shown displaying a login screen for the caregiver assistance application.

Once at the initial web page corresponding to caregiver assistance application 124, caregiver assistance application 124 instructs the web browser of the electronic device 104 to display a login screen on the display of the electronic device 104. FIG. 7 illustrates an example of such a login screen 144. Login screen 144 is shown in FIG. 7 as being displayed on a mobile electronic device (smart phone) 104a. This is done merely for purposes of illustrating one specific type of electronic device 104 with which caregiver assistance system 106 may be utilized. Other types of devices 104 may be used and FIGS. 8-17 depict illustrative screens of caregiver assistance system 106 that do not show the specific type of electronic device 104 on which they are displayed, which is intended to re-emphasize the device agnostic nature of caregiver assistance system 106.

Login screen 144 includes a username field 146 in which a user is asked to input his or her username, as well as a password field 148 in which the user is asked to input his or her password. In order for the user to input this information, he or she utilizes the conventional input features of the electronic device 104. Thus, for example, when the electronic device 104 includes a touch screen display and the user touches or otherwise selects either of the fields 146, 148, the electronic device 104 shows on its display, in some embodiments, an image of an alphanumeric keyboard that can be used by the user to input his or her username and password. After this information is typed into fields 146, 148, the user either presses the "enter" or "return" button, or touches the login icon 150 shown on login screen 144. If electronic device 104 does not include a touch screen display, the user may enter the username and login information using a conventional keyboard, a mouse or other pointer, or other methods.

Caregiver assistance application 124 receives the user's username and password at step 152 of general algorithm 226 (FIG. 5). That is, the entry of the user's username and password into electronic device 104 is communicated by the electronic device 104 to caregiver assistance server 90. As was noted, this may be done in a conventional manner utilizing the WiFi, or other network communication, abilities of the electronic device 104. Once caregiver assistance application 124 receives the username and password, it consults rules repository 126 to see if the username and password match an approved user. As mentioned previously, local rules repository contains information input into application 124 by an authorized representative of the healthcare facility in which caregiver assistance application 124 is installed. This information includes a list of those individuals who are authorized to use caregiver assistance application 124, including their usernames and passwords (and other data, such as their authorization level, email address, phone number, etc.).

Figure 8:
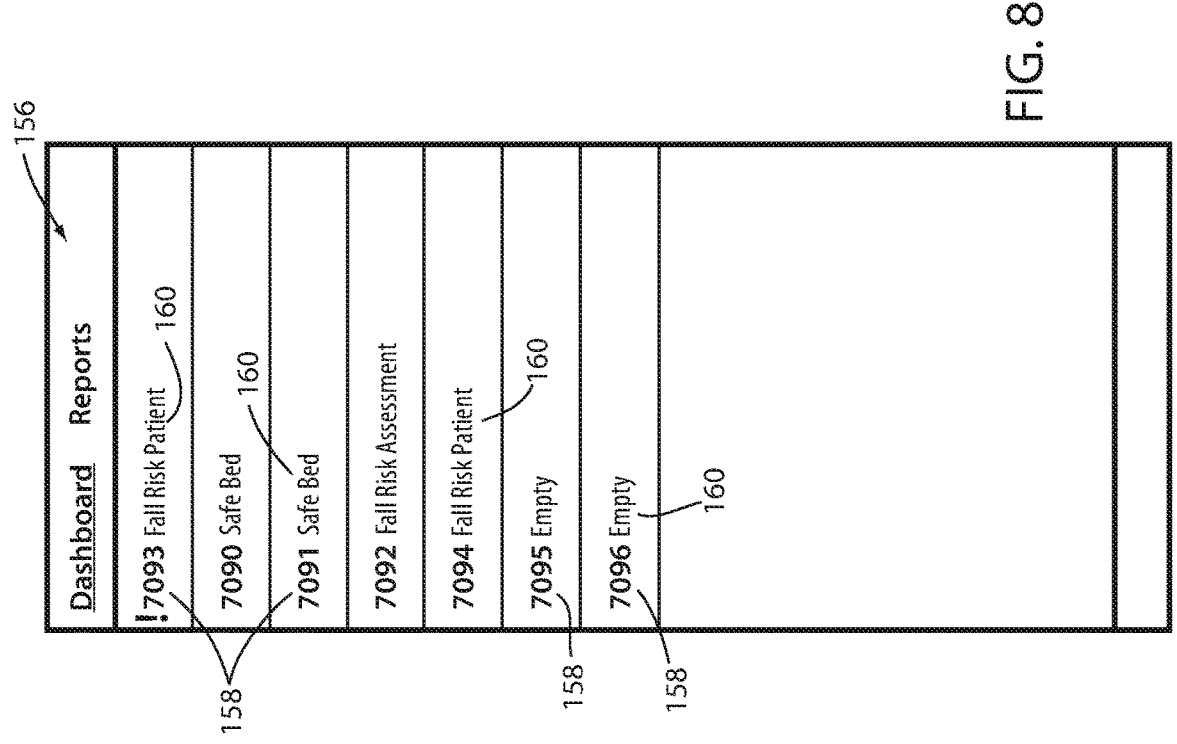
FIG. 8 is an illustrative screenshot of a room listing screen that is displayable on an electronic device of the caregiver assistance system.

If the user's username and password match an authorized entry within local rules repository 126, caregiver assistance application 124 proceeds to step 154 of algorithm 226 (FIG. 5). At step 154 of algorithm 140, caregiver assistance application 124 displays a main screen that allows a user to access the functionality of caregiver assistance application 124. The content of the main screen may vary widely. FIG. 8 illustrates one example of such a main screen in the form of a room listing screen 156. Room listing screen 156 includes a plurality of rows. Each row includes a room identifier 158 that identifies a particular room 92 within the healthcare facility in which caregiver assistance system 106 is installed. The particular selection of which rooms to list in room listing screen 156 corresponds, in the illustrated embodiment, to the particular person who has just logged into caregiver assistance application 124. That is, each caregiver is assigned a level of administrative access to the data contained within caregiver assistance application 124. This assignment is carried out by one or more of the authorized individuals 136 who initially set up caregiver assistance application 124. In at least one embodiment, caregivers are assigned an access level that only permits them to view rooms that they themselves have been assigned. Caregiver managers may be granted a higher access level that permits them to view all of the rooms of all of the caregivers which they oversee. Administrators may be granted an even higher access that allows them to see all of the rooms in the entire healthcare facility. Still other types of access levels may be used and/or created, and the rules defining the access level architecture are stored within local rules repository 126.

Caregiver assistance application 124 automatically determines which rooms a particular caregiver has been assigned by communicating with a server on local area network 74 that maintains room assignments for caregivers. In the example illustrated in FIG. 4, nurse call server 96 is shown to include a caregiver-room assignment table 122 that stores the room assignments for the caregivers within the healthcare facility. As noted previously, caregiver-room assignment table 122 may be stored on a different server. During installation of caregiver assistance application 124, an authorized administrator inputs the IP address of the server containing caregiver room assignment table 122 (and/or other data necessary to gain access to caregiver-room assignment table 122). Similar data is also input for all of the other servers and tables discussed herein. After a user successfully logins at step 152 of algorithm 140, caregiver assistance application 124 sends a message to the server having caregiver room assignment table 122. The message requests an up-to-date listing of the rooms that are assigned to the caregiver who has just logged in. After receiving this information, caregiver assistance application 124 displays those rooms on the display of the electronic device 104 (or, more precisely, causes the web browser to display those rooms on the display of the electronic device 104). Thus, in the example of FIG. 8, caregiver assistance application 124 displays rooms 7090 through 7096, which correspond to the rooms assigned to the particular caregiver who is using caregiver assistance application 124.

In some healthcare facilities, caregivers may be assigned to specific patients instead of specific rooms. In such instances, caregiver assistance application 124 may be configured in at least two alternative manners. In a first manner, caregiver assistance application 124 continues to display a room listing, such as the room listing screen 156 of FIG. 8. In a second manner, caregiver assistance application 124 displays a patient listing screen that, instead of rows of the rooms the caregiver has been assigned, displays rows of each of the patients the caregiver has been assigned to. When configured in either manner, caregiver assistance application 124 determines the data to display by sending a request to the particular server(s) within the healthcare facility that maintain data sufficient to correlate specific caregivers to specific patients. In the particular embodiment illustrated in FIG. 4, there is no server that correlates patients to caregivers. However, by utilizing patient-room assignment table 114 in conjunction with another server that stores caregiver to room assignments (e.g. table 122), caregiver assistance application 124 is able to determine which particular patients are assigned to a particular caregivers, and which rooms 92 those particular patients are located in within the healthcare facility.

For example, if caregiver assistance application 124 is configured to display room listing screen 156 (FIG. 8) in a healthcare facility that assigns caregivers to specific patients, rather than to specific rooms, caregiver assistance application 124 sends a first request message and a second request message. The first request message is sent to whatever server maintains a table correlating caregivers and the particular patient they have been assigned to care for. The second request is sent to ADT server 94 and requests a listing of the specific rooms in which the caregiver's assigned patients are located. By using the data retrieved from these two requests, caregiver assistance application 124 is able to determine which particular patients the caregivers has been assigned, along with the rooms those patients have been assigned. Caregiver assistance application 124 is thereby able to display room listing screen 156 in a manner that is tailored to the particular caregiver who is using caregiver assistance application 124.

In those embodiments where caregiver assistance application 124 is configured to display rows of the patients assigned to a particular caregiver, rather than the patient room listing screen 156, caregiver assistance application 124 need not send the first request message mentioned above. Instead, it can send a single request message to the particular server that stores the table (or other data structure) that correlates caregivers to particular patients. Caregiver assistance application 124 then displays on the display screen of the electronic device used by that particular caregiver the listing of those patients who are assigned to that particular caregiver.

Still further, in some embodiments, a particular healthcare facility may assign rooms to particular caregivers but may desire to have room listing screen 156 replaced by a patient listing screen that identifies the particular patients assigned to a particular caregiver. Caregiver assistance application 124 may be configured to accommodate this desire. In order to do so, caregiver assistance application 124 sends a message to nurse call server 96 requesting the room assignments for a particular caregiver and also sends a message to ADT server 94 requesting the patient assignments to particular rooms. By using the data from both of these requests, caregiver assistance application 124 is able to determine which patients have been assigned to which caregivers, and is therefore able to display a patient listing screen instead of, or in addition to, room listing screen 156. This is configurable by an authorized individual 136 and is stored in rule repository 126.

It should be noted that, although most electronic devices 104 are associated with a particular caregiver, this is not always the case, particularly for stationary electronic devices 104b. Stationary electronic devices 104b, which may include large screen smart televisions, may be associated with a particular unit of a healthcare facility, a particular nurse's station, wing, floor, and/or other section of the healthcare facility. For these devices, the login credentials may be tailored to the particular location and/or intended function of that particular electronic device 104b. For example, a stationary electronic device 104b may be associated with an oncology unit, an east wing, nurse's station XYZ, the second floor, or rooms A through G, or something else. In such instances, caregiver assistance application 124 may be configured to assign a username and password to each such electronic device 104 that is custom tailored to that specific device. Thus, for example, if a particular electronic device 104 is positioned at a nurse's station within a pediatric oncology unit, the device 104 may be assigned a username of "pediatric oncology display" and have its own specific password. Once an authorized user has logged into caregiver assistance application 124 via that device, caregiver assistance application displays the rooms and/or patient data corresponding to the pediatric oncology unit on that particular device. The room and/or patient data may include rooms and/or patients that are assigned to multiple caregivers, thereby allowing the electronic device 104 to display information beyond that associated with a single caregiver.

Regardless of whether caregiver assistance application 124 displays room listing screen 156 at step 154 or a patient listing screen, caregiver assistance application 124 is also configured to display a status summary 160 (FIG. 8). Status summaries 160 provide additional information about the status of the patient in the room and/or the patient support apparatus 20 assigned to that room. Thus, for example, the status summary 160 may indicate that a patient is a fall risk or a bed sore risk, that the patient support apparatus 20 is currently empty, that the patient support apparatus 20 is in a compliant or non-compliant state, and/or that one or more tasks (e.g. a fall risk assessment) are waiting to be performed for that particular patient and/or room.

Caregiver assistance application 124 receives the data necessary for displaying status summaries 160 by communicating with one or more of the servers on local area network 74. In some embodiments, caregiver assistance application 124 receives all of the patient support apparatus data from patient support apparatus server 86, which may be a commercially available bed status server, such as, but not limited to, the iBed server available from Stryker Corporation of Kalamazoo, Michigan. Further details of the iBed server are found in the Stryker Installation/Configuration Manual for the iBed Server 2.0 (document 5212-209-001 REV A), published in May of 2016 by Stryker Corporation of Kalamazoo, Michigan, the complete disclosure of which is incorporated herein by reference. In other embodiments, caregiver assistance application 124 is configured to receive the patient support apparatus status data directly from the patient support apparatuses 20 themselves, rather than through an intermediary server, such as the above-noted iBed server.

Caregiver assistance application 124 receives the patient data and protocol data from EMR server 98 and/or ADT server 94. ADT server 94 may contain, in addition to patient room assignments, requirements data identifying one or more protocols that the healthcare facility requires its caregivers to follow when caring for one or more patients. Such requirements data, for example, may specify what assessments are to be performed on a patient, such as an assessment of the patient's fall risk and/or bed sore risk. Alternatively, such requirements data may be stored elsewhere, such as, but not limited to, local rules repository 126. In some embodiments, the requirements data that specifies which assessments (fall, skin, etc.) are to be performed for a given patient may depend upon the location of the patient within the healthcare facility. For example, some healthcare facilities may configure local rules repository 126 such that all patients within a particular wing, floor, or other section, receive both a fall risk assessment and a skin assessment, while patients within a different location are to receive only one or none of these assessments. Caregiver assistance application 124 automatically checks these local rules when a new patient is admitted to the healthcare facility (as determined from communication with ADT server 94) and, if no assessment is recorded in EMR server 98 (which may be sent there either by caregiver assistance application 124 itself or another device), it displays a reminder on various screens associated with that patient that such an assessment needs to be performed.

Thus, when a new patient enters the healthcare facility, caregiver assistance application 124 automatically determines from server 94 and/or rules repository 126 (or another location) if a particular patient is supposed to have a fall assessment, bed sore assessment, or other assessment performed. If so, caregiver assistance application 124 further sends an inquiry to EMR server 98 to determine if such an assessment has been completed for that particular patient. If it has not, caregiver assistance application 124 displays this lack of completion in the status summary 160 (FIG. 8). In the example shown in FIG. 8, the patient in room 7092 has not yet had a fall risk assessment performed, and this information is shown in the status summary 160 corresponding to room 7092.

Turning more particularly to the examples shown in FIG. 8, caregiver assistance application 124 receives the data necessary to indicate that the patient in room 7093 is a fall risk from EMR server 98. Caregiver assistance application 124 requests and receives the data indicating "safe bed" for rooms 7090 and 7091 from patient support apparatus server 86. The term "safe bed" displayed in the status summary 160 for rooms 7090 and 7091 of FIG. 8 means that the patient support apparatuses 20 in those rooms are currently configured in their desired state (i.e. in their compliant states). As was noted previously, this "desired state" may be a preprogrammed part of caregiver assistance system 106, or it may be modified and/or customized by an authorized individual 136. In either case, the definition of the desired state, or "safe bed," is stored in local rules repository 126. In some embodiments, a particular patient support apparatus 20 is considered to be in the "safe bed" state if all of the following are true: the exit detection system 46 is armed, the brake is activated, the litter frame 28 is at its lowest height (or within a specified range of its lowest height), and at least three of the siderails 36 are in their raised position. As noted, this "safe bed" state may be modified to include, among other things, one or more of the following: a requirement that the NC cable 102 is plugged into an NC power outlet; a requirement that the nurse call cable 78 is plugged into the nurse call outlet 82; a requirement that a monitoring function for the patient support apparatus 20 is armed; and/or other requirements. Still further, the "safe bed" state may be modified to remove one or more of the aforementioned criteria.

As was noted previously, caregiver assistance application 124 determines if a patient in a particular room needs to have an assessment performed by checking EMR server 98 and/or one or more other servers on the local area network that define what assessments are to be performed (and when), and that record when such assessments have been completed. As will be discussed in more detail below, such assessments may be completed, in at least some embodiments, using electronic devices 104 and/or patient support apparatuses 20, and sent to EMR server 98 from either or both of these devices. Alternatively, such assessments may be performed by other devices who forward their results to EMR server 98. In the particular example shown in FIG. 8, caregiver assistance application 124 has determined that the patient in room 7092 has not yet had a fall risk assessment performed, and therefore displays "fall risk assessment" in the status summary 160 associated with room 7092.

Similarly, caregiver assistance application 124 is configured to display in the status summary 160 the results of any patient assessments that a caregiver should be aware of. Thus, in the example of FIG. 8, caregiver assistance application 124 displays "fall risk patient" for the status summary 160 associated with room 7094. This indicates that a fall risk assessment has been performed for the patient in room 7094 and that assessment has indicated that that particular patient is at a higher risk for falling. The results of this fall risk assessment are typically stored in EMR server 98, and caregiver assistance application 124 is configured to request these results from EMR server 98 and display them in status summary 160, if a fall risk (or bed sore risk, or other risk) has been detected.

Caregiver assistance application 124 is also configured to display in the status summary 160 whether or not a patient support apparatus 20 is currently occupied by a patient or not. This information is obtained from the weight sensors, such as load cells, that are included within the scale/exit detection system 46 of each patient support apparatus 20. Each patient support apparatus 20 periodically transmits its weight readings to patient support apparatus server 86. Those weight readings are forwarded to caregiver assistance server 90. If the weight readings are less than a threshold (e.g. 50 pounds), caregiver assistance application 124 concludes that the patient support apparatus 20 is unoccupied and may display this information in status summary 160 (or it may display other information that is configured to have a higher priority, such as, but not limited to, any assessments that need to be performed for that particular patient). Such information may be displayed in status summary 160 with the words "weight not detected," or "patient out of bed," or some other text that indicates that the patient support apparatus 20 is not detecting the patient.

In the example shown in FIG. 8, caregiver assistance application 124 is displaying the word "empty" for rooms 7095 and 7096. This indicates that those rooms currently do not have any patients assigned to them. Caregiver assistance application 124 determines this information by sending a request to ADT server 94 server asking it for patient information for those rooms 92 that are assigned to the particular caregivers who are using caregiver assistance system 106. In this example, ADT server 94 instructed caregiver assistance application 124 that rooms 7095 and 7096 were not assigned to any patients. Accordingly, caregiver assistance application 124 displays "empty" in the status summary 160 for these rooms.

It will be understood that the examples of information displayed in the status summaries 160 shown in FIG. 8 are merely several examples of the types of information that may be displayed on room listing screen 156. Caregiver assistance application 124 may be modified to show less, more, and/or different information in status summaries 160 and/or to eliminate them entirely. Still further, caregiver assistance application 124 may be configured to display the status summaries 160 in different colors, depending upon the informational content of the status summary 160. Thus, for example, tasks that need to be completed may be highlighted in a different color (e.g. orange); information indicating a task has not been complete within a designated time period and/or a patient support apparatus 20 that is out of compliance with a desired state may be highlighted in yet another color (e.g. red); and information indicating that no tasks or no out-of-compliance states exist may be indicated in yet another color (e.g. green). Indications of alerts may be displayed in status summary through flashing text, or still other manners.

Figure 9:
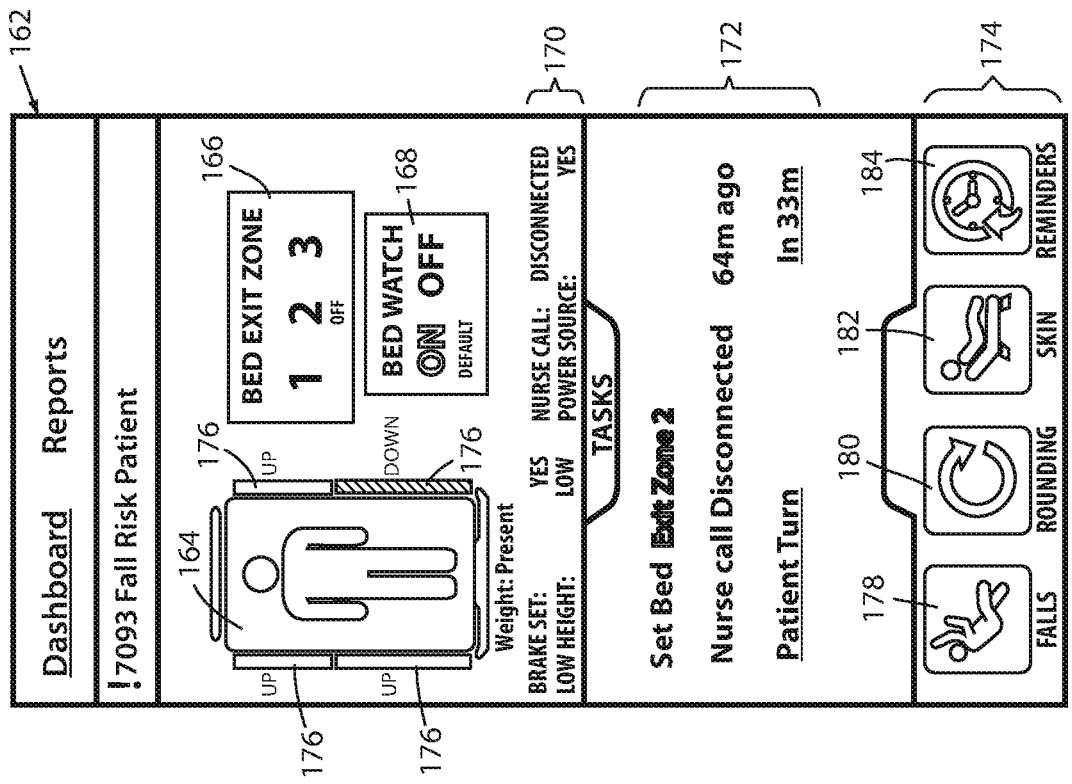
FIG. 9 is an illustrative screenshot of a room overview screen that is displayable on an electronic device of the caregiver assistance system.

Returning to general algorithm 226 of caregiver assistance system 106 (FIG. 5), general algorithm 226 proceeds from step 154 to step 155. At step 155 of general algorithm 226, caregiver assistance application 124 determines whether or not a caregiver has selected a particular room from amongst the rooms listed in room listing screen 156. If the caregiver has not selected a particular room, algorithm 226 returns to step 154 and continues to display the room listing screen 156. If the caregiver has selected a particular room, application 124 proceeds to step 157 where it displays on the screen of electronic device 104 a room overview screen 162, such as the room overview screen 162 of FIG. 9. Thus, if a user navigates to the room listing screen 156 at any point while using caregiver assistance application 124, he or she can press on (or otherwise select) a particular room listed on room listing screen 156. Caregiver assistance application 124 responds to this selection by displaying a room overview screen 162 that corresponds to the particular room 92 selected by the user. The particular room overview screen 162 shown in FIG. 9 is therefore displayed by caregiver assistance application 124 when a user specifically selects room 7093 from room listing screen 156. Caregiver assistance application 124 may also include other tools for allowing a user to navigate to room overview screen 162, such as, but not limited to, a search function in which room numbers may be entered/searched.

Room overview screen 162 (FIG. 9) displays information about a particular room 92 within the healthcare facility and the patient associated with that room 92. It will be understood that room overview screen 162 may be changed to a bay overview screen, or other type of overview screen, if the particular room that the caregiver has selected is a semi-private room containing more than one patient support apparatus 20 or patient. In such embodiments, caregiver assistance application 124 displays a bay overview screen (not shown) similar to room overview screen 162 that is specific to the particular bay that the caregiver has selected the within semi-private room.

Room overview screen 162 (or a similar bay overview screen) includes a bed icon 164, an exit detection system status indicator 166, a bed watch status indicator 168, a bed status bar 170, a summary area 172, and a task menu 174 (FIG. 9). Bed icon 164 includes a plurality of siderail icons 176 positioned along the sides of bed icon 164. Within each siderail icon 176 is an indicator (not labeled) that includes the word "up" or "down." Caregiver assistance application 124 selectively displays the "up" or "down" down indication within the siderail icons 176 based upon the current status of the siderails 36 of the patient support apparatus 20 within room 7093. Caregiver assistance application 124 receives the up/down status of each siderail 36 from patient support apparatus server 86 and displays "up" or "down" to match the current siderail status of patient support apparatus 20. Caregiver assistance application 124 is also configured, in at least some embodiments, to display the siderail icons 176 in a different color if they are in the down state, such as, but not limited to, amber. This distinguishes the siderail icons 176 from those corresponding to siderails 36 that are in an up position, which may be displayed in a green color, or some other color.

Exit detection system status indicator 166 (FIG. 9) indicates the current status of the scale/exit detection system 46 of the corresponding patient support apparatus 20 (e.g. the patient support apparatus 20 positioned in room 7093). That is, status indicator 166 indicates if the exit detection system 46 is currently armed or not. It also indicates what zone of the exit detection system the user has selected, if the exit detection system is armed and includes multiple zones. Many exit detection systems are configured to allow a user to select different zones of permitted movement. The different zones allow a patient to move different amounts before the exit detection system issues an alert. In the example of FIG. 9, the patient support apparatus 20 includes an exit detection system 46 having three zones, the second of which is highlighted. The exit detection system 46 is indicated in FIG. 9 as being disarmed (off). Caregiver assistance application 124 displays an "armed" or "on" indicator when the exit detection system 46 is armed, and also highlights the selected zone (1, 2, or 3). Further information about the zones and/or operation of an exit detection system that may be incorporated into patient support apparatus 20 and utilized in caregiver assistance system 106 are found in commonly assigned U.S. patent application Ser. No. 14/918,003 filed Oct. 20, 2015, by inventors Marko Kostic et al. and entitled EXIT DETECTION SYSTEM WITH COMPENSATION, the complete disclosure of which is incorporated herein by reference.

Bed watch status indicator 168 (FIG. 9) indicates whether the bed watch feature of the patient support apparatus 20 is turned on or off. The bed watch feature is a monitoring feature that is included in some embodiments of patient support apparatuses 20, but may be omitted in other embodiments. In general, the bed watch feature, when activated, causes controller 48 to monitor the status of a plurality of components of the patient support apparatus 20 to issue an alert when any of those components are changed from a desired state to an undesired state. In several embodiments, the particular features that are monitored by the bed watch feature are defined by the patient fall risk reduction protocol 93 (FIG. 2). The patient fall risk reduction protocol 93 also defines what the desired states are for each of the particular components that are being monitored by the bed watch feature.

For example, if the bed watch function is activated and includes the monitoring of the siderails 36 of the patient support apparatus 20, controller 48 of patient support apparatus 20 will issue an alert if one or more of the siderails are lowered, or otherwise moved to an undesired state. Generally speaking, when the bed watch feature is incorporated into a particular patient support apparatus 20, the patient support apparatus 20 can be configured to issue an alert if any one or more of the following changes on the patient support apparatus 20: the exit detection system 46 is disarmed, a siderail 36 is lowered, the patient exits the patient support apparatus 20, the brake is deactivated, the height of the bed is raised beyond a specified level, the NC power cord 102 is unplugged, and/or the nurse call cable 78 is unplugged. The particular features of patient support apparatus 20 that, when changed, trigger an alert can be selected by an authorized user, such as authorized individual 136. This selection may take place via one of the control panels 42 of the patient support apparatus 20, one of electronic devices 104, and/or via a computer in communication with caregiver assistance server 90. The alert issued by patient support apparatus 20 in response to the bed watch function detecting an undesired state may be a local alert (at patient support apparatus 20), a remote alert (e.g. sent to patient support apparatus server 86 and/or to caregiver assistance application 124), or a combination of both a local and a remote alert. The user may select from these different types of alerts via patient support apparatus 20, electronic devices 104, and/or a computer in communication with server 90.

Bed status bar 170 provides additional information about the current status of patient support apparatus 20 (FIG. 9). This includes an indication of whether or not the brake on the patient support apparatus 20 is activated or not; information indicating whether litter frame 28 is at its lowest height or not; information indicating whether the nurse call cable 78 is plugged into nurse call outlet 82 or not; and information indicating whether the NC power cable 102 is plugged into an NC outlet or not. All of the information shown in status bar 170 (as well as all of the patient support apparatus 20 data displayed by caregiver assistance application 124) is sent by the patient support apparatuses 20 (via transceiver 60) to patient support apparatus server 86, which then forwards it to caregiver assistance server 90 and caregiver assistance application 124. Although, in some modified embodiments, caregiver assistance application 124 and caregiver assistance server 90 are configured to receive this information directly from patient support apparatuses 20, thereby avoiding the need for a separate patient support apparatus server 86.

The data displayed in bed status bar 170 (FIG. 9) is updated in real time, or near real time. In most embodiments of patient support apparatuses 20, the patient support apparatuses 20 are configured to automatically (and nearly immediately) communicate their status to patient support apparatus server 86 whenever a change occurs in their status. Thus, for example, if the nurse call cable 78 gets unplugged from the nurse call outlet 82, the patient support apparatus 20 sends a message automatically and almost immediately thereafter to patient support apparatus server 86. The patient support apparatus server 86 automatically, and immediately or nearly immediately, forwards this status update to caregiver assistance application 124. Caregiver assistance application 124, in turn, updates the information displayed in bed status bar 170 to indicate that the nurse call cable has been unplugged. A caregiver, who may be remote from a particular room 92 and/or a particular patient support apparatus 20, thereby gets a real time, or near real time, update of the status of patient support apparatus 20 when utilizing caregiver assistance application 124.

Summary area 172 of room overview screen 162 (FIG. 9) lists one or more items of information about the patient, the patient's patient support apparatus 20, the room assigned to that particular patient, and/or any data generated from the reminder algorithm 145. In the example shown in FIG. 9, the summary area 172 includes a reminder to set, or arm, exit detection system 46, and more specifically to select zone 2 when arming it. This data comes from reminder algorithm 145, which allows a caregiver to select one or more tasks associated with a patient and/or patient support apparatus 20, schedule those tasks, have reminders issued via caregiver assistance application 124, and display data about those reminders in summary area 172.

Summary area 172 also includes an entry re-iterating the fact that the nurse call cable 78 has been disconnected. Still further, summary area 172 includes an entry reminding the caregiver of any upcoming tasks that are scheduled for this particular patient, room, and/or patient support apparatus 20. In the specific example of FIG. 7, the summary area 172 of room overview screen 162 includes a reminder to turn the patient in room 7093 in thirty-three minutes. This task data is input into caregiver assistance application 124 by a caregiver and/or authorized individual 136 using the reminder algorithm 145. Additional or alternative reminders may be included using the reminder algorithm 145, such as reminders to perform a fall risk assessment, to perform a bed sore risk assessment, to perform a rounding duty, to carry out one or more therapies, etc. Such reminders include, in some embodiments, an indication of the amount of time until the task is supposed to be completed (e.g. a time until the next patient turn or next rounding task) and/or an amount of time that has elapsed since the time the task was last completed (e.g. the amount of time since the patient was last turned or the amount of time since the rounding duties were last performed).

Task menu 174 of room overview screen 162 (FIG. 9) identifies a plurality of different tasks that may be undertaken by a caregiver utilizing caregiver assistance application 124. In the example shown in FIG. 9 and elsewhere (e.g. FIGS. 10-17), task menu 174 includes four separate task icons: a falls task icon 178, a rounding task icon 180, a skin task icon 182, and a reminders task icon 184. If a caregiver selects one of these task icons 174-182 at step 159, caregiver assistance application 124 begins execution of a corresponding algorithm 140, 141, 143, and 145 at step 161 (FIG. 5). More specifically, if a caregiver selects fall task icon 178 at step 159, caregiver assistance application 124 begins execution of fall risk reduction algorithm 143 at step 161. If a caregiver selects rounding task icon 180 at step 159, caregiver assistance application 124 begins execution of rounding algorithm 140 (FIG. 6) at step 161. If a caregiver selects skin task icon 182 at step 159, caregiver assistance application 124 begins execution of skin care algorithm 141 at step 161. Finally, if a caregiver selects reminder icon 184 at step 157, caregiver assistance application 124 begins executing reminder algorithm 145 at step 161.

The selection of these various icons and their associated algorithms cause caregiver assistance application 124 to bring up different screens corresponding to the selected task. The different screens enable a user to perform one or more tasks with respect to that particular patient. For example, if the user selects the falls task icon 178, caregiver assistance application 124 begins execution of fall risk reduction algorithm 143 and causes the display of electronic device 104 to display one or more screens allowing a caregiver to perform one or more tasks associated with reducing the likelihood of a patient falling, such as, but not limited to, the screens shown in FIGS. 19-27. These tasks include, but are not limited to, performing a fall risk assessment and configuring the patient support apparatus 20 according to a fall risk reduction protocol (e.g. in a manner that helps to reduce or minimize a patient's fall risk). The particular screen that is displayed by caregiver assistance application 124 in response to a user selecting the falls task icon 178 (or any of the other task icons of task menu 174) may be an initial screen that is part of a larger set of screens that are displayable by caregiver assistance application 124 in order to assist the caregiver with the selected task. In some embodiments, this initial screen is of the type shown in FIG. 19, although other screens may be initially shown.

If a caregiver selects skin task 182 (FIG. 9) at step 159 (FIG. 5), caregiver assistance application 124 executes skin care algorithm 141, which causes it to display an initial skin care screen (not shown) that assists the caregiver in performing a bed sore risk assessment, documenting one or more existing skin states or conditions, and/or setting one or more reminders or configurations on the patient support apparatus 20 to assist in preventing the development and/or worsening of a patient's bed sores. As with fall task icon 180, the selection of skin task icon 182 causes caregiver assistance application 124 to display an initial screen associated with caring for a patient's skin that is part of a larger set of screens adapted to assist the caregiver in caring for the patient's skin. The additional screens within that larger set are accessible through the initial screen, or through one or more of the other screens that are accessible from the initial screen.

If a caregiver selects reminder task icon 184 step 159 (FIG. 5), caregiver assistance application 124 executes reminder algorithm 145 and displays an initial reminder screen (not shown) that allows the caregiver to set, edit, and/or cancel reminders associated with caring for that patient. Such reminders include, but are not limited to, reminders to turn the patient, reminders to perform one or more therapies on the patient (e.g. a lateral rotation therapy using mattress 38), reminders to perform caregiver rounds, and other reminders. Whatever the specific reminder, caregiver assistance application 124 is configured to display the reminder in summary area 172 of room overview screen 162, in the status summary 160 of room listing screen 156, and/or on other screens of caregiver assistance application 124. The display may include not only an indication of the reminder, but also a time remaining until the reminder deadline is met (or, if the reminder deadline has passed, an amount of time that has passed since the reminder deadline expired). Still further, in some embodiments of caregiver assistance system 106, caregiver assistance application 124 is configured to send a notification to the caregiver when a reminder deadline is reached (or at one or more configurable times ahead of the reminder deadline). The notifications include, in some embodiments, an email, a text, a phone call, or some other type of notification, as will be discussed more below.

During the performance of any of the tasks identified in task menu 174, caregiver assistance application 124 is configured to continue to display task menu 174 on the screens that are specifically associated with those tasks. If the user selects a task icon corresponding to a task different from the one currently being executed, caregiver assistance application 124 switches to performing the algorithm associated with that particular task. In the specific case of the rounding algorithm 140, if the caregiver selects rounding task icon 180 from one of the screens associated with tasks icons 178, 182, or 184, caregiver assistance application switches to step 192 of rounding algorithm 140 (FIG. 6), as will be discussed in more detail below.

If the caregiver does not select any of the tasks from task menu 174, general algorithm 226 (FIG. 5) of caregiver assistance application 124 proceeds to step 163 where it determines if a caregiver has input a command to control one or more aspects of the patient support apparatus 20. If the caregiver has input such a command, algorithm 226 proceeds to step 165 where it sends the command to the patient support apparatus 20. The routing of this command is through caregiver assistance server 90, in at least one embodiment. That is, the command to control one or more aspects of the patient support apparatus 20 is sent from the electronic device 104 to caregiver assistance application 124 (via one or wireless access points 76). After being received, caregiver assistance application 124 forwards the command either directly to the corresponding patient support apparatus 20 using wireless access points 76, or it forwards the command to patient support apparatus server 86, which then forwards the command to the patient support apparatus 20 using one or more wireless access points 76. When the command is received at the patient support apparatus 20, controller 48 checks to see if the command is an authorized command and, if so, implements the command.

After both steps 163 and 165 of general algorithm 226 (FIG. 5), caregiver assistance application 124 proceeds to step 167 where it checks to see if the caregiver has input a command to change the currently displayed room overview screen 162 back to the room listing screen 156 of FIG. 8. If the caregiver has, algorithm 226 returns back to step 154 and proceeds in the manner previously described. If the caregiver has not, algorithm returns back to step 157 and proceeds in the manner previously described.

It should be noted that the display of different screens within caregiver assistance application 124 is not only controlled by the area that a user presses/selects on a particular screen, but also by the caregiver's use of the conventional "back" and "forward" functions of the web browser that the caregiver is using to access caregiver assistance application 124. Thus, for example, if a user is viewing room overview screen 162 of FIG. 9 and wishes to return to viewing room listing screen 156 of FIG. 8, he or she can simply press, or otherwise activate, the "back" function of the web browser the caregiver is using.

Figure 6:
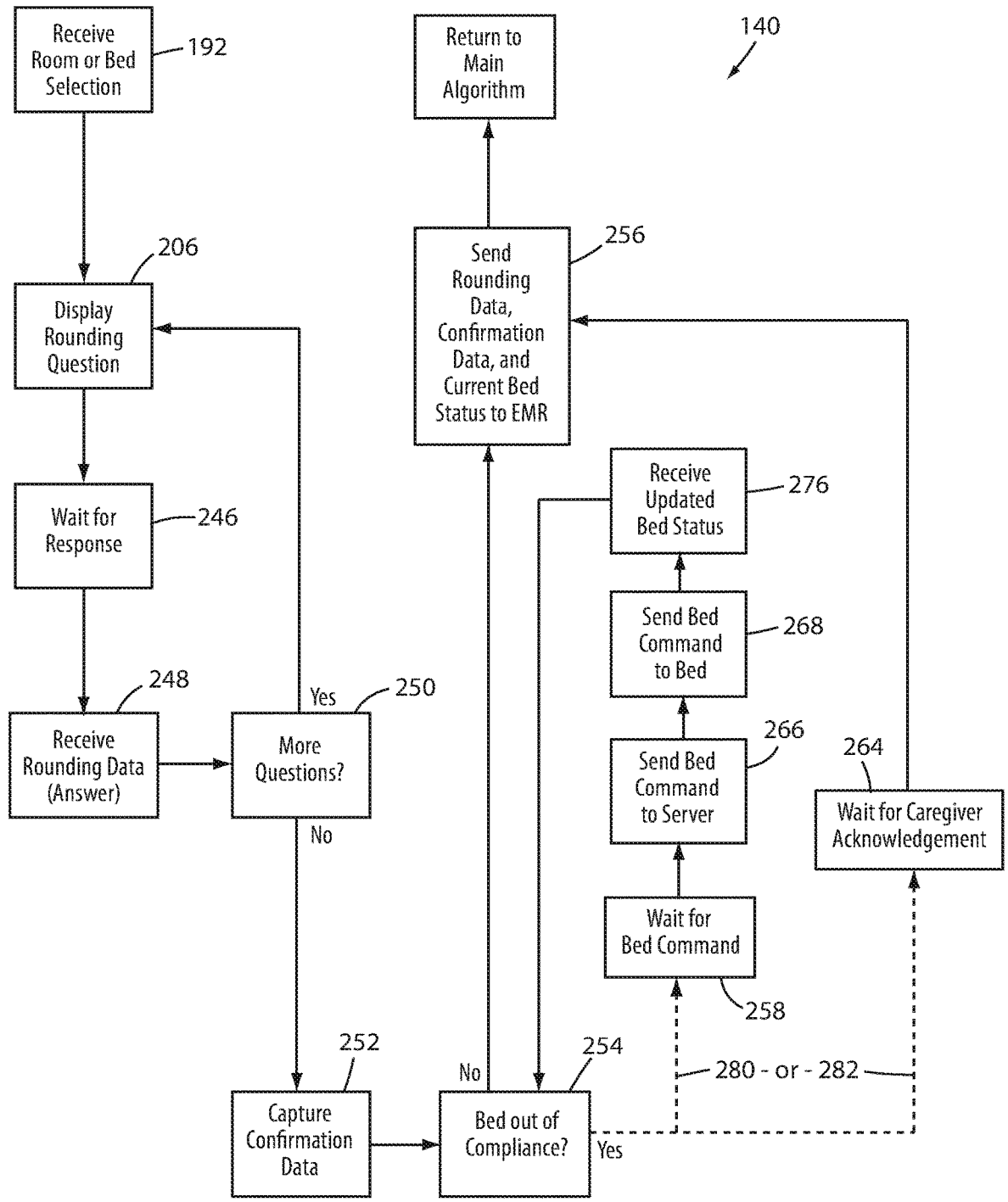
FIG. 6 is a flow diagram of a caregiver assistance algorithm executed by the caregiver assistance application of FIG. 3.

If a caregiver selects rounding task icon 180 (FIG. 9) at step 159 of general algorithm 226 (FIG. 5), caregiver assistance application 124 begins executing rounding algorithm 140 of FIG. 6. Rounding algorithm 140 begins at a step 192 where caregiver assistance application 124 receives and/or verifies a room selection or bed selection. In response to such a room selection or bed selection, caregiver assistance application 124 proceeds to displaying a first rounding screen 190, such as the first rounding screen 190 shown in FIG. 10. The caregiver's selection of a specific room or patient support apparatus is used by caregiver assistance application 124 in order for caregiver assistance application 124 to know what patient and/or room rounding information to display on screen 190 (and its subsequent rounding screens). If a caregiver navigates to screen 190 from a screen, such as screen 162 of FIG. 9, caregiver assistance application displays information on screen 190 that corresponds to the same bed and/or room as was selected in screen 162. Thus, because screen 162 was displaying information for room 7093 in FIG. 9, if a user navigates to screen 190 of FIG. 10 by pressing on the rounding task icon 180 of FIG. 9, caregiver assistance application will automatically display the rounding information on screen 190 that also corresponds to room 7093.

However, there may be situations where the first rounding screen 190 is called up by the caregiver without having previously selected a particular room and/or patient, or there may be situations where the caregiver wants to utilize first rounding screen 190 for a different room or patient than what was selected on a previously displayed screen. In those situations, first rounding screen 190 may be modified and/or supplemented by a screen, or input field, in which the caregiver can select a particular room and/or patient for carrying out the rounding tasks associated with first rounding screen 190. In some embodiments, the particular patient support apparatus 20 may be selected at step 192 by having the user manually enter the room number of the patient whose rounding information he or she is intending to collect. In other embodiments, patient support apparatus 20 may have a short range wireless transmitter (e.g. one or more near field transmitters and/or a Bluetooth transmitter) that communicates automatically with the mobile electronic device 104a and tells the device 104a which patient support apparatus 20 it is. In response, caregiver assistance application 124 automatically associates the first rounding screen 190 with the patient support apparatus 20 identified in the wireless communication it received from the patient support apparatus 20. In still other embodiments, caregiver assistance application 124 may be configured to automatically associate first rounding screen 190 with a particular room or patient based on the current location of the mobile electronic device 104a at the time the first rounding screen 190 was first accessed. Such current location information may be received from RTLS server 100.

Figures 10, 11:
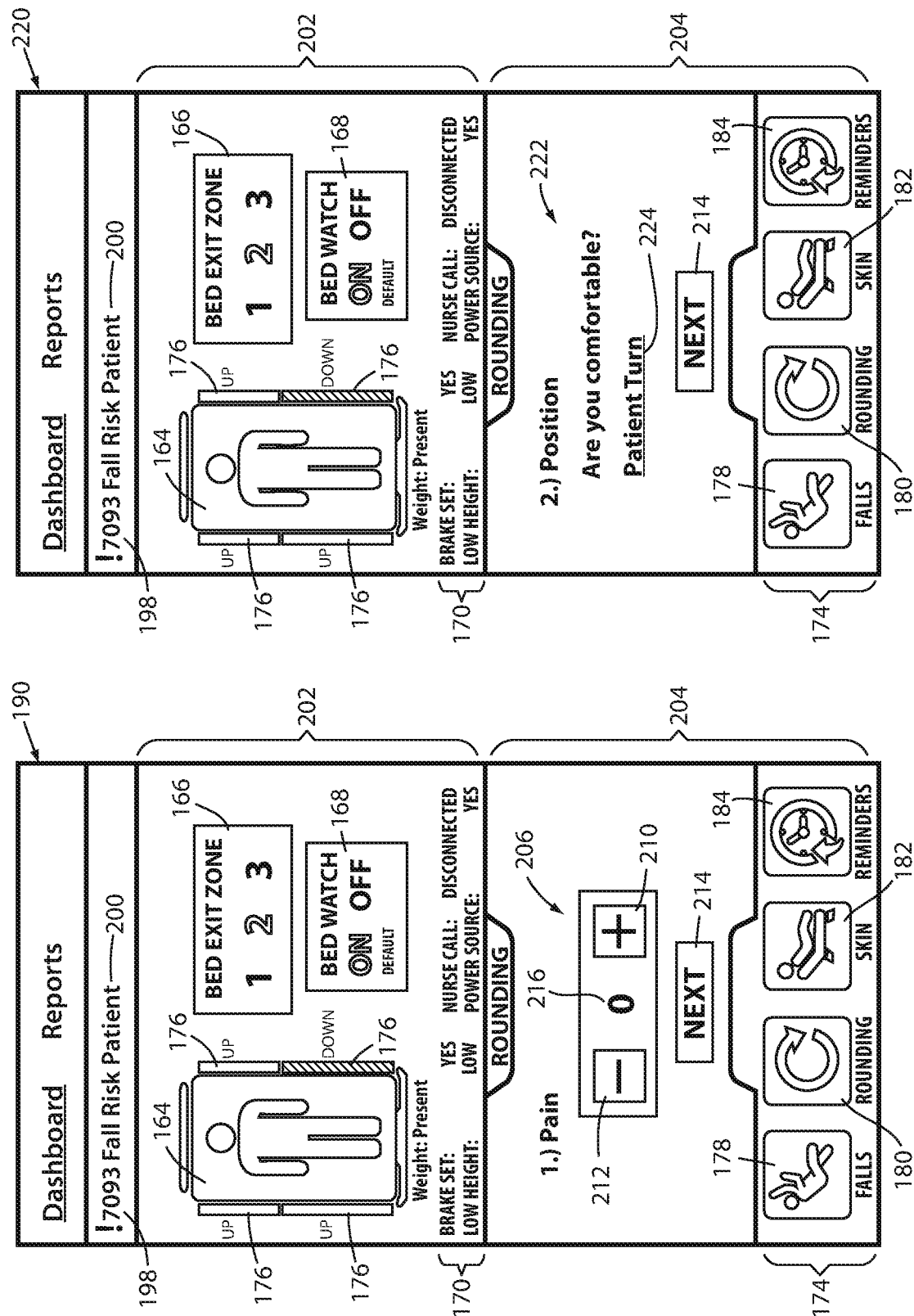
FIG. 10 is an illustrative screenshot of a first rounding question screen that is displayable on an electronic device of the caregiver assistance system.
FIG. 11 is an illustrative screenshot of a second rounding question screen that is displayable on an electronic device of the caregiver assistance system.

Regardless of the specific manner in which the room for first rounding screen 190 is selected, caregiver assistance application 124 displays the selected room in a room identifier location 198 (FIG. 10). Caregiver assistance application 124 may also display the same content of status summary 160 (of room listing screen 156) in a status location 200 adjacent the room identifier location 198. First rounding screen 190 also includes a top portion 202 and a bottom portion 204. Top portion 202 includes the same information displayed in the top half of room overview screen 162 (FIG. 9). Specifically, it includes the bed icon 164, exit detection system status indicator 166, bed watch status indicator 168, and bed status bar 170. Bottom portion 204, however, does not include summary area 172 of room overview screen 162, but instead includes a first rounding question 206. The first rounding question identifies a question intended to be asked by the caregiver of the patient while the caregiver is performing his or her rounding duties. Caregiver assistance application 124 displays this first question 206 at step 208 of algorithm 140 (FIG. 6).

The specific first rounding question 206 displayed at step 208 of algorithm 140 (illustrated in FIG. 10) is a question regarding the patient's pain level. Specifically, it is a question of the patient's current pain level on a scale of zero through ten with zero being the lowest pain level and ten being the highest. It will be understood that, although first question 206 is described herein as being the "first" question shown after rounding task icon 180 is selected, the particular order of questions displayed by caregiver assistance application 124 may be varied, and the term "first" in the phrase "first rounding question" is merely used to distinguish the question from other rounding question, not to indicate any particular significance to its sequential order.

First rounding question screen 190 (FIG. 10) includes a plus sign icon 210, a minus sign icon 212, a next icon 214, and a current pain level indicator 216. The plus sign icon 210 and minus sign icon 212 are pressed by the caregiver to increase or decrease the patient's pain level, as indicated by the current pain level indicator 216, until the corresponding pain level shown by indicator 216 matches the pain level expressed by the patient. For example, if the user indicates their pain level is a six, the caregiver presses the plus sign icon 212 six times until the current pain level indicator reads a six. The caregiver then presses next icon 214 and caregiver assistance application 124 saves the pain level data and proceeds to display a second rounding question screen, such as second rounding question screen 220 shown in FIG. 11.

In other embodiments, first rounding question screen 190 (FIG. 10) is modified to allow the user to input the patient's current pain level in one or more alternative and/or additional manners. For example, in another embodiment, plus and minus signs 210 and 212 are replaced by a numeric keypad icon and the user simply presses on the numbers of the keypad to directly input the patient's pain level. In yet another embodiment, a slider bar icon is displayed on screen 190 and the user touches the slider bar while moving the sliding portion of the bar to a position corresponding to the number of the patient's pain level. Still other manners of allowing the user to input the patient's pain level are possible.

Second rounding question screen 220 includes all of the same elements of first rounding question screen 190 with the exception of the specific rounding question displayed in bottom portion 204. That is, second rounding question screen 220 displays the room identifier in the room identifier location 298, the status of the room in the room status location 200, and all of the same icons in top portion 202 that are found in the top portion 202 of first rounding screen 190. Bottom portion 204, however, differs from bottom portion 204 of screen 190 in that it is directed to a different rounding question. Specifically, bottom portion 204 of second rounding question screen 220 includes a rounding question 222 inquiring whether the patient is currently in a comfortable position or not. If the patient is not, the caregiver assists the patient to a more comfortable position and documents this movement or turning of the patient by pressing a "patient turn" icon 224 displayed on screen 220. In response to pressing the turn icon 224, caregiver assistance application 124 records the fact that the patient has been turned, along with the identity of the particular caregiver associated with the mobile electronic device 104a from which the turn indication was received. Caregiver assistance application 124 further time stamps this recording and, as will be discussed further below, includes it with other rounding information that is transmitted to the EMR server 98.

Figures 12, 13:
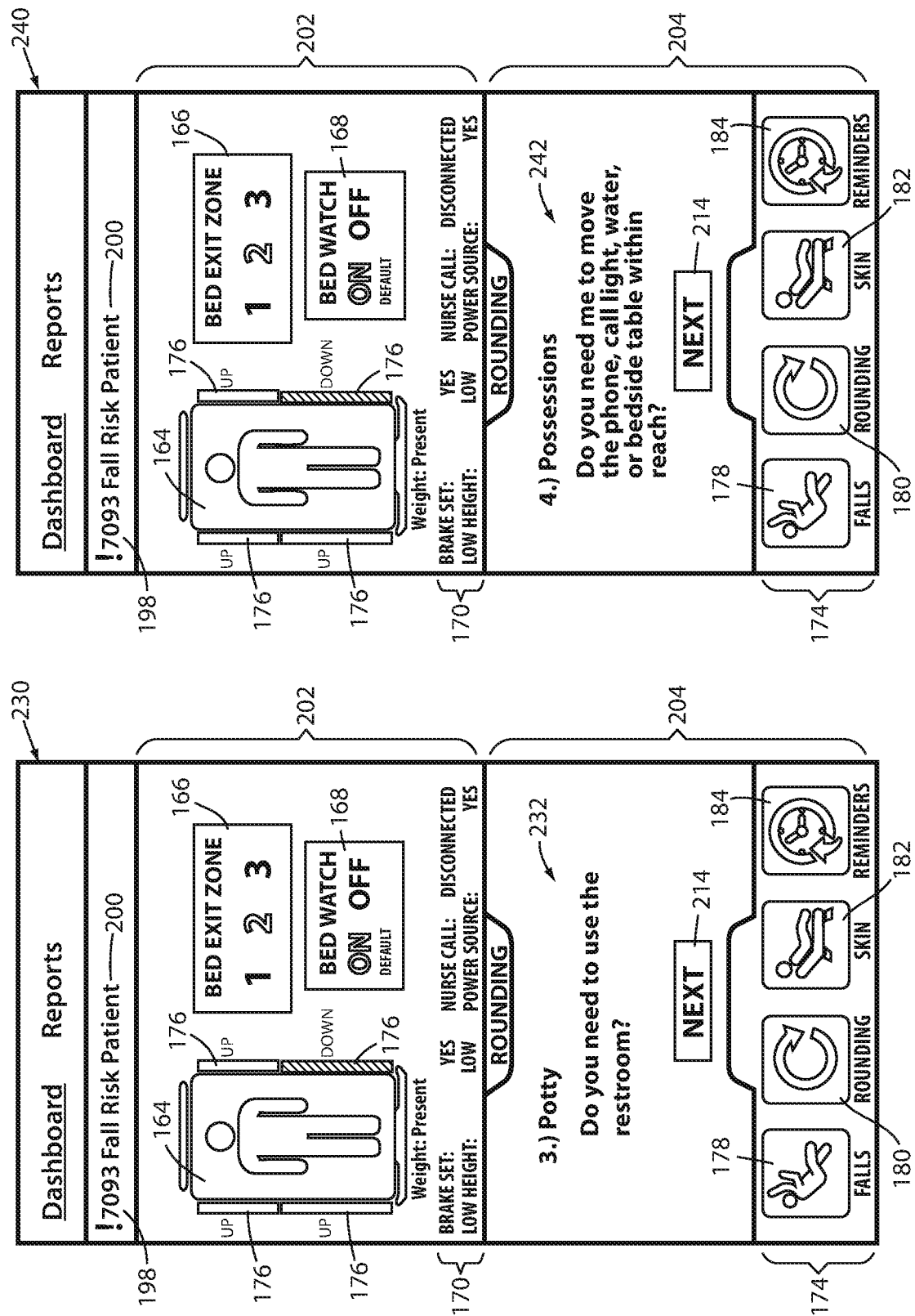
FIG. 12 is an illustrative screenshot of third rounding question screen that is displayable on an electronic device of the caregiver assistance system.
FIG. 13 is an illustrative screenshot of a fourth rounding question screen that is displayable on an electronic device of the caregiver assistance system.

If the patient does not need to be turned or otherwise repositioned, the caregiver presses the next icon 214 on screen 220 (FIG. 11). The pressing of the next icon 214 on screen 220 causes caregiver assistance application 124 to display a third rounding question screen 230, an example of which is shown in FIG. 12. Third rounding question screen 230 includes a top portion 202 and a bottom portion 204. Top portion 202 include all of the same information as the top portions 202 of first and second rounding question screens 190 and 220. Bottom portion 204 differs from these screens in that it includes a third rounding question 232, which, in this case, is an inquiry into whether the patient needs to use the restroom or not. If the patient needs to use the restroom, the caregiver assists, or otherwise allows, the patient to use the restroom. In some embodiments, third rounding question screen 230 may include an input that, when pressed by the caregiver, sends a message to caregiver assistance application 124 indicating that the patient has used the restroom, and caregiver assistance application 124 saves this information for entry into that particular patient's electronic medical record. If the patient does not need to use the restroom, or has finished using the restroom, the caregiver presses the next icon 214.

In response to pressing the next icon 214 on third rounding question screen 230, caregiver assistance application 124 displays a fourth rounding question screen 240, one example of which is shown in FIG. 13. Fourth rounding question screen 240 includes a top portion 202 and a bottom portion 204. Top portion 202 include all of the same information as the top portions 202 of first, second, and third rounding question screens 190, 220, and 230. Bottom portion 204 differs from these screens in that it includes a fourth rounding question 242, which, in this case, is an inquiry into whether the patient needs any possession or not. If the patient needs a possession, the caregiver retrieves it for the patient, or otherwise moves it into a position within the room 92 that is accessible to the patient without requiring the patient to leave patient support apparatus 20. After ensuring that the patient has access to any of his or her possessions, the caregiver again presses the next icon 214.

It can be seen from FIG. 6 that the input of rounding information utilizing the rounding screens 190, 220, 230, and 240 corresponds to steps 246, 248, and 250 of algorithm 140. That is, at step 208 (FIG. 4), caregiver assistance application 124 displays a first rounding question. This step is accomplished by displaying first rounding question screen 190 and its associated first rounding question 206. After displaying this information, caregiver assistance application 124 waits for a response from the caregiver at step 248. After waiting for the response, algorithm 140 receives data from the caregiver at step 248. This data input corresponds to, for example, the caregiver entering the patient's pain level via screen 190, or repositioning the patient and documenting the repositioning step using patient turn icon 224 of screen 220. For some screens, such as screens 230 and 240, the data entry includes the pressing of the next icon 214, which indicates that the corresponding question was asked by the caregiver.

After receiving the caregiver assistance data at step 248 (FIG. 6), caregiver assistance application 124 moves onto step 250 where it determines whether or not there are more caregiver assistance questions to ask. Thus, after displaying first, second, and third rounding question screens 190, 220, and 230, respectively, caregiver assistance application 124 returns back to step 208 and displays the another rounding question screen. However, after displaying the fourth rounding question screen 240 (FIG. 13), caregiver assistance application 124 moves from step 250 to step 252 where it waits for verification data verifying the completion of the rounding task to be input by the caregiver, as will be discussed in greater detail below.

Before proceeding to describe step 252, it is worth noting that the particular number and content of the caregiver assistance questions displayed by caregiver assistance application 124 on electronic devices 104 may be varied from the four shown in FIGS. 10-13. Caregiver assistance application 124 includes an administrative portal that can be accessed by an authorized individual 136 to change the number of questions asked, the content of the questions, the order of the questions, and the content of the data that is to be input into the application 124 in response to receiving the patient's answers.

At step 252 (FIG. 6) of rounding algorithm 140, caregiver assistance application 124 displays a rounding completion screen 260 (FIG. 14). The rounding completion screen 260 includes a rounding documentation window 262 that indicates the time (and date) at which the caregiver completed his or her rounding task associated with the particular room shown in room identifier location 198 (or more particularly, the patient in that room), as well as a verification that the information entered by the caregiver (e.g. pain level) has been sent to caregiver assistance server 90 and recorded by caregiver assistance application 124. In some embodiments, as will be discussed more below, caregiver assistance application 124 proceeds to automatically forward this rounding information to EMR server 98 for storage in the patient's electronic medical record. In the embodiments which follow algorithm 140, as shown in FIG. 6, caregiver assistance application 124 does not send this rounding data to EMR server 98 until it receives verification data verifying that the caregiver was actually present at the patient's bedside while he or she accessed and used rounding screens 190, 220, 230, and 240.

Figure 17:
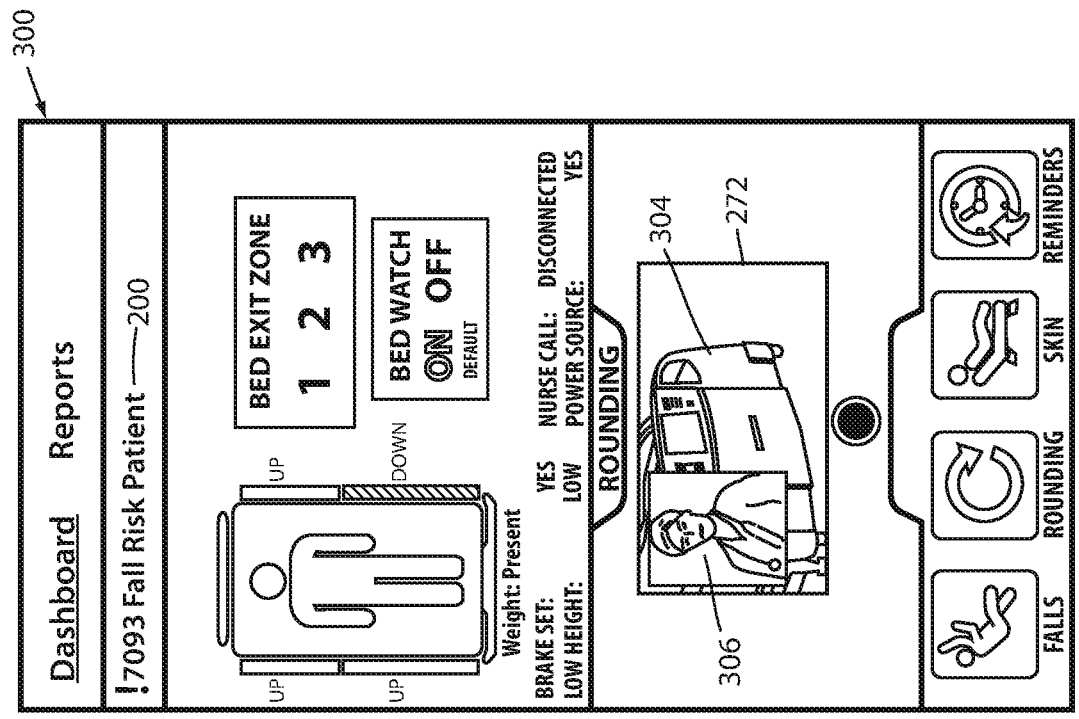
FIG. 17 is an illustrative screenshot of a third rounding verification screen that is displayable on an electronic device of the caregiver assistance system.
Figure 16:
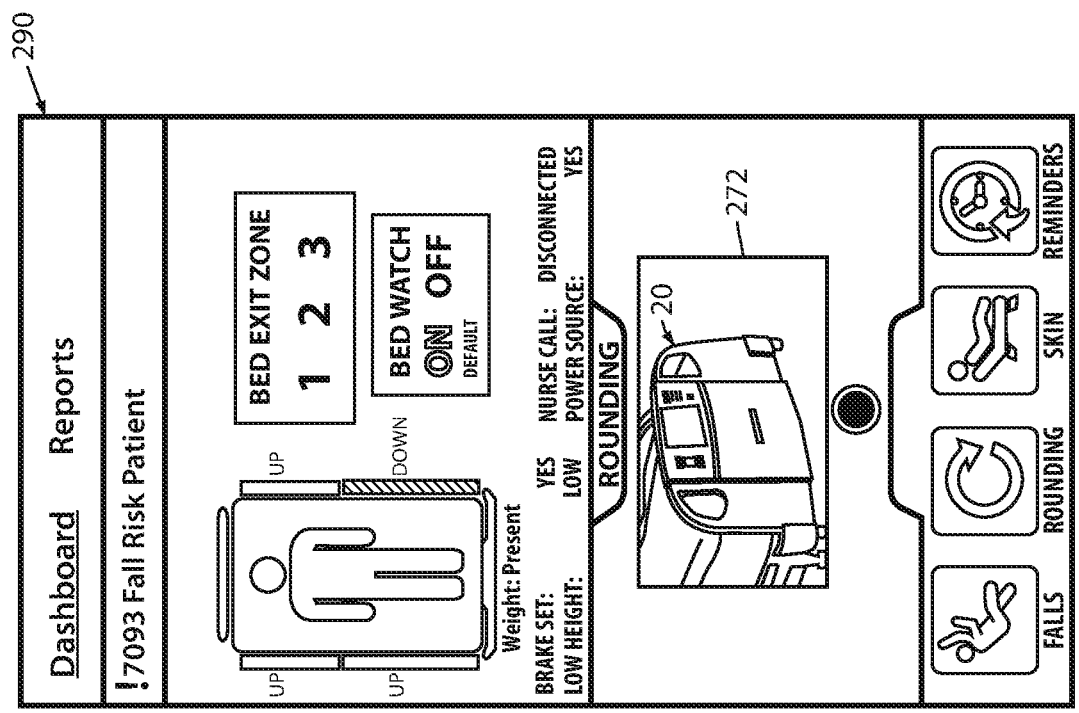
FIG. 16 is an illustrative screenshot of a second rounding verification screen that is displayable on an electronic device of the caregiver assistance system.

More specifically, in the embodiment of algorithm 140 shown in FIG. 6, caregiver assistance application 124 proceeds from step 250 (if there are no more rounding questions) to step 252 where it seeks to capture verification data. As noted, the verification data refers to data that is used to verify that the caregiver actually entered the room and performed his or her rounding duties in the patient's room. The particular verification data that is captured at step 252 may vary widely from embodiment to embodiment. FIGS. 15, 16, and 17 illustrate three different verification screens that may be utilized by caregiver assistance application 124 for gathering this verification data. Each of the three screens is intended to gather different verification data. In practice, caregiver assistance application 124 will typically utilize only a single one of the screens shown in FIGS. 15-17. The inclusion of multiple screens in FIGS. 15-17 is intended to show a variety of different types of verification data that may be gathered by caregiver assistance application 124. It will further be understood, of course, that still other types of verification data may be gathered by caregiver assistance application 124 besides the three examples shown in FIGS. 15-17.

Verification screen 270 (FIG. 15) includes a bottom portion 204 having an image window 272 and a capture icon 274. Image window 272 displays an image currently being sensed by the camera built into mobile electronic device 104a. Capture icon 274 is touched by the caregiver when the caregiver is ready to take a picture. The image window 272 in FIG. 15 specifically shows a Quick Response (QR) code because, in the embodiment illustrated therein, each patient support apparatus 20 is configured to display a QR code on its display 70 in response to the caregiver pressing a specific control, or series of controls. Controller 48 of the patient support apparatus 20 generates the QR code in a manner that embeds at least two pieces of information in the QR code: a unique identifier corresponding to that particular patient support apparatus 20 (e.g. identifier 186) and a current time (and day).

Caregiver assistance application 124 is adapted to analyze the QR code to determine the specific patient support apparatus 20 identified in the code and the time at which the photograph was captured by the mobile electronic device 104a. Caregiver assistance application 124 compares the specific patient support apparatus 20 identified in the QR code with the identity of the patient support apparatus 20 positioned in the room identified in the room identifier location 198 to ensure that they match. If they do not match, then the image that the caregiver captured using capture icon 274 is not an image of the patient support apparatus 20 associated with the patient to whom the caregiver just asked the rounding questions. In this case, caregiver assistance application 124 displays an error message and does not proceed to step 254 of algorithm 140 (FIG. 6). If the patient support apparatus 20 identifiers match, then caregiver assistance application 124 proceeds to step 254.

Caregiver assistance application 124 receives patient support apparatus identifiers 186 (FIG. 4) that uniquely identify each patient support apparatus 20 from patient support apparatus server 86. When each patient support apparatus 20 sends these identifiers 186 to patient support apparatus server 86, the patient support apparatus 20 also sends a locator identifier 138 (FIG. 4) that uniquely identifies the location beacon 84 within that room. This information is shared with caregiver assistance application 124. Caregiver assistance application 124 therefore receives not only the unique IDs corresponding to each patient support apparatus 20, but also the location of those patient support apparatuses 20. Alternatively, it receives the unique IDs of the patient support apparatuses 20 and bed location table 88. In either situation, caregiver assistance application 124 receives sufficient information to know the specific patient support apparatus ID of each patient support apparatus 20 and the specific room in which each patient support apparatus is located in. This is the information caregiver assistance application 124 uses to compare against the patient support apparatus identifier contained within the QR code.

For example, if a caregiver takes a picture of a QR code using verification screen 270 and capture icon 274, and the picture is taken in room 7093 (FIG. 15), caregiver assistance application 124 compares the patient support apparatus 20 ID contained within the QR code to the location record it maintains for that particular patient support apparatus 20. If that record also indicates that that particular patient support apparatus 20 is located in room 7093, then caregiver assistance application 124 accepts the QR code as verification that the caregiver was actually present in that room when he or she performed his or her rounding tasks. If the record does not match, caregiver assistance application 124 displays an error message and does not accept the picture of the QR codes as verification of the caregiver's physical presence during the rounding task.

Patient support apparatuses 20 suitable for use with the verification method utilized by verification screen 270 of FIG. 15 include a clock that keeps track of the current time, and a controller 48 configured to embed both the current time and the unique ID of the patient support apparatus 20 into the QR code. Some examples of patient support apparatuses 20 that include internal clocks and that may be utilized with algorithm 140 and the verification process of FIG. 13 are disclosed in commonly assigned U.S. patent application Ser. No. 15/642,621 filed Jul. 6, 2017, by inventors Anuj Sidhu et al. and entitled PATIENT SUPPORT APPARATUSES WITH CLOCKS, the complete disclosure of which is incorporated herein by reference. Other types of patient support apparatuses 20 can, of course, alternatively be used.

The patient support apparatuses 20 utilized with the verification process of FIG. 15 are configured to display the QR code somewhere on their display screen 70. The display of the QR code may be constant with repetitive updates to include the current time (e.g. every minute or so), or the display may be intermittent in response to the caregiver pressing, or otherwise activating, one or more controls on the patient support apparatus 20. With respect to the latter option, one of controls 72 may be specifically dedicated to causing patient support apparatus 20 to display the QR code, or the code may be displayed in response to the caregiver navigating to a specific screen on which the QR code is displayed. Still other manners of getting the patient support apparatus 20 to display the QR code may be utilized.

It will also be noted that there is no requirement that the patient support apparatus 20 specifically utilizes a QR code. That is, other codes may be utilized, such as, but not limited to, a bar code. Still further, in some embodiments, patient support apparatus 20 is configured to not encode the information at all. In such embodiments, patient support apparatus 20 displays, or can be manipulated by the caregiver to display (e.g. using controls 72), a screen on which both the current time and the unique identifier of the patient support apparatus 20 are shown. The caregiver captures an image of that display using the camera function of the mobile electronic device (e.g. smart phone, tablet, etc.) and forwards the image to caregiver assistance application 124. Caregiver assistance application 124 processes the image to extract the ID of the patient support apparatus and the time from the captured image. The extracted patient support apparatus ID is then matched against the record data for that particular room, as discussed above. If the captured patient support apparatus ID data matches the data contained in the records (data repository 128) of caregiver assistance application 124, caregiver assistance application 124 proceeds to step 254, which will now be described.

At step 254 of rounding algorithm 140 (FIG. 6), caregiver assistance application 124 determines whether or not patient support apparatus 20 is in a compliant or non-compliant state. The definition of a compliant state may be determined during the installation of caregiver assistance application 124 (or modified thereafter) in accordance with the particular requirements of the healthcare facility into caregiver assistance application 124 is being installed, or it may be pre-defined by the vendor of caregiver assistance application 124. Alternatively, or additionally, the compliant state may be defined based upon whether or not a fall risk reduction protocol is currently being implemented for the patient assigned to that particular patient support apparatus 20, as will be discussed in greater detail below with respect to FIGS. 21-30. In any of the embodiments, the definition of the compliant state may also or alternatively be modified and/or defined by an authorized individual 136 after installation of system 106. In many embodiments, the compliant state includes the same criteria that are monitored by the bed watch feature discussed above. That is, in many instances, healthcare facilities will define a compliant state of a patient support apparatus as one in which all of the following are true: the brake is activated, the litter frame 28 is at its lowest height, the exit detection system 46 is armed, a monitoring feature is armed, at least three of the siderails 36 are up (and/or specific ones of the siderails are up), the NC power cable 102 is plugged into a wall outlet, and the nurse call cable 78 is plugged into a nurse call outlet 82. Other definitions of a compliant state may, of course, be utilized.

Caregiver assistance application 124 checks to see if the patient support apparatus 20 is in the compliant state or not at step 254. Caregiver assistance application 124 performs this step by asking patient support apparatus server 86 for the current status data of the patient support apparatus 20 when the user reaches step 254. The current status data of each patient support apparatus 20 is maintained by patient support apparatus server 86 in table 88 (FIG. 4). As was noted, patient support apparatuses 20 send their status data to patient support apparatus server 86 whenever they sense a change in their state (or upon a specific request from patient support apparatus server 86). After caregiver assistance application 124 receives the current status data of the patient support apparatus 20 from patient support apparatus server 86, it checks to see if the current status data matches the compliant state criteria discussed above. If caregiver assistance application 124 determines that the patient support apparatus 20 is currently in a compliant state, it moves to step 256 of rounding algorithm 140 (FIG. 6). If caregiver assistance application 124 determines that the patient support apparatus 20 is not currently in a compliant state, it moves to following a first control path 280 (in one embodiment) or to following a second control path 282 (in another embodiment).

At step 256 (FIG. 6), caregiver assistance application 124 sends various data to the EMR server 98 to be documented in the electronic medical record of the patient for whom the caregiver just completed his or her rounding tasks. This transmission occurs without the caregiver having to perform any additional step beyond the ones previously described. The particular data that is sent to EMR server 98 includes the following: (a) the rounding data entered by the caregiver into the mobile electronic device 104*a* during the rounding task (e.g. pain level, whether the patient used the restroom, etc.); (b) the verification data captured during step 252 (or data indicating that the rounding tasks was verified); (c) whether or not the patient support apparatus 20 is in a compliant state or not (or alternatively, the current status of patient support apparatus 20 with respect to its brake, siderails, litter frame height, exit detection system, nurse call cable, and/or power cable); (d) a time and date stamp; and (e) data sufficient to identify the caregiver who is currently logged into the particular mobile electronic device 104*a* from which caregiver assistance application 124 receives the rounding data.

The time and date stamp may include both the time and date at which the data is received by caregiver assistance application 124 from the corresponding mobile electronic device 104, and the time and data that is encoded in the verification data presented on the display 70 of the patient support apparatus 20 and captured by the caregiver in image window 272. Alternatively, or additionally, the time and data stamp may refer to the time at which this data is sent to EMR server 98 by caregiver assistance application 124. EMR server 98, upon receipt of this data, updates the patient's electronic medical record with the new data, and caregiver assistance application 124 returns back to step 154, thereby enabling the caregiver to complete another rounding task and/or another one of the tasks associated with task menu 174.

After completing step 256 (FIG. 6), caregiver assistance application 124 is configured, in at least some embodiments, to update any timer that is associated with the rounding task that was just completed. In other words, caregiver assistance application 124 may be configured to implement a reminder algorithm 145 that reminds the caregivers of tasks that they are to perform. Such tasks may include the rounding tasks. Thus, for example, if a caregiver is to perform a rounding tasks for his or her rooms, the reminder algorithm 145 will issue periodic reminders and/or display on the associated screens of electronic devices 104 the amount of time remaining until the rounding task should be performed. In these embodiments, caregiver assistance application 124 is configured to reset such timers after a caregiver completes a rounding task at step 254. Thus, for example, if a caregiver is supposed to perform a rounding task every two hours, and the caregiver has just completed a round for room 1703, caregiver assistance application 124 automatically resets the timer for room 1703 to two hours after step 256 is completed. The corresponding time information displayed on the screens of mobile electronic devices 104a is therefore also automatically reset, thereby providing the caregivers with up-to-date indications of how much time is left until the next rounding task is to be performed. Caregiver assistance application 124 maintains and updates timers for rounding tasks associated with each room and/or patient as well as, in some embodiments, timers for other tasks.

Returning to step 254 of algorithm 140 (FIG. 6), if the patient support apparatus 20 is determined by caregiver assistance application 124 to not be compliant at that step, it proceeds to either 1st control path 280 or second control path 282, depending upon the particular embodiment of caregiver assistance application 124. Turning first to the embodiment in which caregiver assistance application 124 proceeds to first control path 280, caregiver assistance application 124 implements the status/command algorithm 147. That is, caregiver assistance application 124 proceeds to step 258 and waits there to receive a command from the caregiver that will remotely change the patient support apparatus 20 to a compliant state. As noted previously, the status/command algorithm 147 allows caregiver assistance application 124 to receive patient support apparatus commands from a caregiver and relay those commands to the corresponding patient support apparatus 20. This enables the caregiver to remotely change the state of the patient support apparatus 20 to be in a compliant state.

For example, if caregiver assistance application 124 determines at step 254 that the patient support apparatus 20 is not in a compliant state because the exit detection system 46 is not currently armed, caregiver assistance application 124 will display an indication informing the caregiver that this is the cause of the non-compliant state. It will also display a control that enables the caregiver to use the mobile electronic device 104a to arm the exit detection system. In some embodiments, this control is simply a display of exit detection system status indicator 166 and tapping on this indicator 166 toggles between arming and disarming exit detection system 46. Other types of controls may also or alternatively be displayed. In response to the user tapping on the control to arm the exit detection system 46, the mobile electronic device 104a sends a message to caregiver assistance server 90 instructing caregiver assistance application 124 to send a command to the patient support apparatus 20 to arm its exit detection system 46. This message is sent at part of step 266 of algorithm 140.

In response to this message, caregiver assistance application 124 proceeds to step 268 (FIG. 6) where it either sends a command directly to the corresponding patient support apparatus 20 to arm its exit detection system 46, or it sends the command to patient support apparatus server 86, which in turn relays the command to the appropriate patient support apparatus 20. In either scenario, the command is received by the patient support apparatus 20 and controller 48 responds by arming the exit detection system.

The arming of the exit detection system 46 by controller 48 also prompts controller 48 to send a new status message to patient support apparatus server 86 that updates the current status of the patient support apparatus 20. This updated status includes the fact that the exit detection system 46 is now armed. Patient support apparatus server 86 forwards this updated status to caregiver assistance application 124, which receives it at step 276 (FIG. 6). Using this updated status data, caregiver assistance application 124 returns to step 254 where it again checks to see if the patient support apparatus 20 is in a compliant state or not. If it is, it proceeds to step 256 and takes the actions associated with step 256 that were previously described. If the patient support apparatus 20 is still out of compliance, caregiver assistance application 124 returns to first control path 280 and step 258 where it waits to receive another command from the caregiver for changing the state of the patient support apparatus 20.

In some embodiments, caregiver assistance application 124 is configured to only allow the caregiver to remotely change those states of the patient support apparatus 20 that do not involve any motion. That is, the caregiver is only allowed to use his or her mobile electronic device 104a at step 266 to send non-movement commands to the patient support apparatus 20. This is done in order to avoid the situation where movement occurs on patient support apparatus 20 when the caregiver may not be present in the room, and such movement may startle the patient and/or be impeded by an obstacle, such as, but not limited to, the patient himself or herself. Such unattended movement may therefore lead to injuries. Therefore, in some embodiments, caregiver assistance application 124 only forwards non-moving commands, such as, but not limited to, commands to arm/disarm the exit detection system 46, arm/disarm the bed watch function, and turn on/off the brake.

In those embodiments of caregiver assistance application 124 where it follows second control path 282 (FIG. 6), caregiver assistance application proceeds to step 264 after it determines at step 254 that the patient support apparatus 20 in not in a compliant state. At step 264, caregiver assistance application 124 displays a screen (not shown) on the mobile electronic device 104a that includes an acknowledgement input. The acknowledgement input is an input that the caregiver must actively touch, or otherwise activate, and includes a message indicating that the patient support apparatus 20 is not in a compliant state. After the caregiver acknowledges that the patient support apparatus 20 is not in a compliant state at step 264, caregiver assistance application 124 proceeds to step 256 and takes the actions associated with step 256 that were previously described. In addition to those actions, caregiver assistance application 124 also sends to EMR server 98 data indicating that the non-compliant state of the patient support apparatus 20 was actively acknowledged (and a time and date of the acknowledgment, in some embodiments). Caregiver assistance application 124 may also send the identity of the caregiver who performed this acknowledgement to EMR server 98.

It can be seen from a comparison of first and second control paths 280 and 282 (FIG. 6) that caregiver assistance application 124 may be configured to either not allow a caregiver to upload rounding data to EMR server 98 if the patient support apparatus 20 is not in a compliant state (first path 280) or to allow the caregiver to upload the rounding data to EMR server 98 for a non-compliant patient support apparatus 20, provided the caregiver actively acknowledges (at step 264) that the patient support apparatus 20 is not in a compliant state (second path 282). Either control path 280 and 282 therefore encourages the caregiver to ensure that the patient support apparatus 20 is in a compliant state, thereby helping the healthcare facility to achieve higher rates of patient support apparatus compliancy.

It will be understood that caregiver assistance application 124 may be modified in still other embodiments to include alternative paths to control paths 280 and 282, and/or to include modifications to these control paths. For example, in at least one embodiment, caregiver assistance application 124 follows a third alternative path (not shown) in which the caregiver has access to an "update status" control on mobile electronic device 104a. The "update status" control, when activated by the caregiver, causes the mobile electronic device 104a to send a message to caregiver assistance application 124 instructing caregiver assistance application 124 to request an updated status of the patient support apparatus 20 from patient support apparatus server 86. The inclusion of the "update status" control allows a caregiver who is positioned next to the patient support apparatus 20 to directly utilize the controls 72 on patient support apparatus 20 to change the patient support apparatus 20 to a compliant state. Once in the compliant state, pressing the "update status" control causes the now-compliant state of the patient support apparatus 20 to be communicated to caregiver assistance application 124, which then moves to step 256 of rounding algorithm 140, thereby allowing the rounding data to be uploaded to EMR server 98.

One modification to this alternative third control path that may be implemented is to configure caregiver assistance application 124 to repetitively and/or automatically request updated statuses from the patient support apparatuses 20. In this modified embodiment, it is not necessary for a caregiver to press, or otherwise activate, an "update status" control. Instead, caregiver assistance application 124 automatically receives patient support apparatus status updates. Thus, in this embodiment, once the caregiver assistance application 124 receives a status update for the patient support apparatus 20 that indicates that the patient support apparatus 20 is in a compliant state, it automatically moves to step 256 without requiring the caregiver to manually manipulate any controls on the mobile electronic device 104a.

In still other embodiments, any of the features of control paths 280, 282, or the third alternative control path described above may be combined together. For example, in some embodiments, caregiver assistance application 124 may be configured to display three options to the caregiver after determining at step 254 that the patient support apparatus 20 is out of compliance: (a) a patient support apparatus command input, (b) an acknowledgement input; and (c) an "update status" input. The caregiver can then decide whether to use the mobile electronic device 104a to change the patient support apparatus state (option a); acknowledge the non-compliant state of the patient support apparatus 20 without correcting it (option b); or change the patient support apparatus 20 state using the controls 72 on the patient support apparatus 20 itself and request that the updated status be communicated to caregiver assistance application 124 (option c). Still other variations may be implemented.

Returning now to step 252 of caregiver rounding algorithm 140 (FIG. 6), caregiver assistance system 106 may be modified to capture verification data at step 252 in a variety of manners different from what was previously described above with respect to step 252 and FIG. 15. Two of these different manners are illustrated in FIGS. 16 and 17. After a caregiver has completed the caregiver assistance questions of FIGS. 10-13 and steps 208, 246, 248, and 250, caregiver assistance application may be configured in some embodiments to execute step 252 by having the caregiver take a photograph of the patient support apparatus 20 itself, rather than the QR code, or other code, on the display 70 of the patient support apparatus 20. An example of this type of verification is shown in FIG. 16, which shows a first alternative verification screen 290.

First alternative verification screen 290, like verification screen 270 of FIG. 15, includes a camera image window 272 that shows the image currently being detected by the camera built into mobile electronic device 104a. In order for a caregiver to properly verify that he or she has completed a rounding task associated with a particular patient, he or she aims the camera of the mobile electronic device 104a such that the camera is pointed at a designated portion of the patient support apparatus 20. In the example shown in FIG. 16, the designated portion includes the foot end of patient support apparatus 20. The designated portion may vary, depending upon the particular patient support apparatus 20, but should include whatever portion of the patient support apparatus 20 includes sufficient information to uniquely identify the patient support apparatus 20 and distinguish it from other patient support apparatuses 20 within the healthcare facility. This identification information may include a sticker with a serial number on it, an engraved serial number, a sticker or other structure coupled to the patient support apparatus 20, and/or any other kind of image information that identifies the particular patient support apparatus 20. Once that portion of the patient support apparatus 20 is within the field of view of the camera of mobile electronic device 104a, the caregiver presses the image capture icon 274 and the mobile electronic device 104a takes a picture of that portion of the patient support apparatus 20. The mobile electronic device 104a also sends the captured image to caregiver assistance application 124 where it is analyzed to verify that the patient support apparatus 20 in the image matches the patient support apparatus assigned to the patient for whom the caregiver just completed his or her rounding tasks, as discussed previously. If there is a match, caregiver assistance application 124 proceeds to step 256 where it uploads the rounding data and other data (including the capture image) to EMR server 98.

In alternative embodiment, caregiver assistance application 124 is configured to have the caregiver capture an image of the patient support apparatus 20 using the camera of mobile electronic device 104a, but the particular portion of patient support apparatus 20 that is captured is immaterial. In this modified embodiment, the caregiver turns on the location feature (GPS, WiFi triangulation, etc.) of the mobile electronic device 104a and has the mobile electronic device automatically append a geographic location to the photograph captured using image window 272. The mobile electronic device 104a forwards the image data (i.e. photograph) to caregiver assistance application 124, along with the location data and, in some cases, the time and date at which the photo was taken. Caregiver assistance application 124 uses knowledge of the geographic location of each room within the healthcare facility (stored in data repository 128, or elsewhere) to determine if the location at which the photograph was taken matches the room in which the corresponding patient is located. If so, it proceeds to step 256 of algorithm 140. If not, it displays an error message.

After a caregiver has completed the caregiver assistance questions of FIGS. 10-13 and steps 208, 246, 248, and 250, caregiver assistance application 124 is configured in some embodiments to display second alternative verification screen 300 of FIG. 17, rather than first alternative verification screen 290 of FIG. 16 (or verification screen 270 of FIG. 15). In such embodiments, the caregiver is instructed to not only capture an image (take a picture) using the camera function of the mobile electronic device 104a, but to also use the selfie feature built into the camera of mobile electronic device 104a that enables the mobile electronic device to simultaneously capture both a forward looking photograph and a rearward looking photograph of the caregiver himself or herself. In other words, caregiver assistance application 124 instructs the caregiver to take a picture using both the forward facing camera of the mobile electronic device 104a and the rearward facing camera of the mobile electronic device 104a. The rearward facing camera is intended to capture an image of the caregiver while the forward facing camera is intended to capture an image of all or a portion of the patient support apparatus 20. An example of this is shown in FIG. 17, which includes a forward-facing image 304 and a rearward facing image 306. The forward facing image 304 captures a portion of the patient support apparatus and the rearward facing image 306 captures an image of the caregiver.

The purpose of the rearward facing camera image of the caregiver is to document the actual presence of the caregiver at the bedside of the patient when he or she has completed the rounding tasks associated with that patient. As with the other verification processes, caregiver assistance application 124 processes the image data from both the forward and rearward facing cameras to identify the patient support apparatus 20 within the forward facing image 304. This image may be of an identifier of the patient support apparatus 20, of a QR or other code, or of any portion of the patient support apparatus 20. Caregiver assistance application 124, in at least one embodiment, also processes the rearward image 306 using conventional facial recognition technology to determine the identity of the caregiver captured therein. In other embodiments, caregiver assistance application 124 does not process the caregiver image data, but instead forwards it to EMR server 98 at step 256 unanalyzed.

In another embodiment, mobile electronic device 104a includes native software onboard that perform facial recognition. In this embodiment, the controller of mobile electronic device 104a is configured to compare an image (taken, for example, by using the digital camera function of the mobile electronic device) of the caregiver with a baseline image taken previously of the caregiver and to determine if there is a match. In other words, in this embodiment, mobile electronic device 104a is programmed to perform facial recognition of the selfie photograph captured by mobile electronic device 104a and, if the selfie is determined to match the authorized caregiver, to forward the captured data to the caregiver assistance application 124. The data forwarded to caregiver assistance application 124 in this embodiment, however, may omit the actual image data of the caregiver, thereby reducing consumed bandwidth, as well as repeated storage of a caregiver's face. Instead of the image data, the mobile electronic device 124 is programmed to send a message confirming that the selfie image captured by the mobile electronic device 104a is of an authorized caregiver (and in some embodiments, the identity of that authorized caregiver). Caregiver assistance application 124 can be configured in this embodiment (as well as other embodiments) to omit any facial recognition software.

It will be appreciated by those skilled in the art that other manners of verifying the caregiver's presence at the patient's bedside during the rounding task may be utilized by caregiver assistance application 124, including verification techniques that do not utilize a camera. For example, in some embodiments, patient support apparatuses 20 include a near field transceiver and/or a short range RF transceiver (e.g. Bluetooth, or infrared) that is detectable by mobile electronic device 104a. By bring the mobile electronic device 104a into sufficiently close proximity to the transceiver, the mobile electronic device 104a is able to wirelessly receive a signal from the patient support apparatus 20 that identifies that particular patient support apparatus 20 and, in some embodiments, also indicates a time. Caregiver assistance application 124 uses the reception of that signal as verification of the caregiver's physical presence at the patient's bedside during the rounding task. The detected signal and/or the fact that the detected signal was received may be forwarded to the EMR server 98 at step 256 (FIG. 6).

It will also be appreciated by those skilled in the art that various other modifications may be made to rounding algorithm 140. These include, but are not limited to, skipping the compliance step 254 completely (along with control paths 280 and/or 282); skipping the capture verification data step 252 and instead proceeding directly from step 250 to step 254; changing the order of one or more steps (e.g. step 192 is moved ahead of step 188 or 154); and/or combinations of one or more of these modifications.

Figure 18:
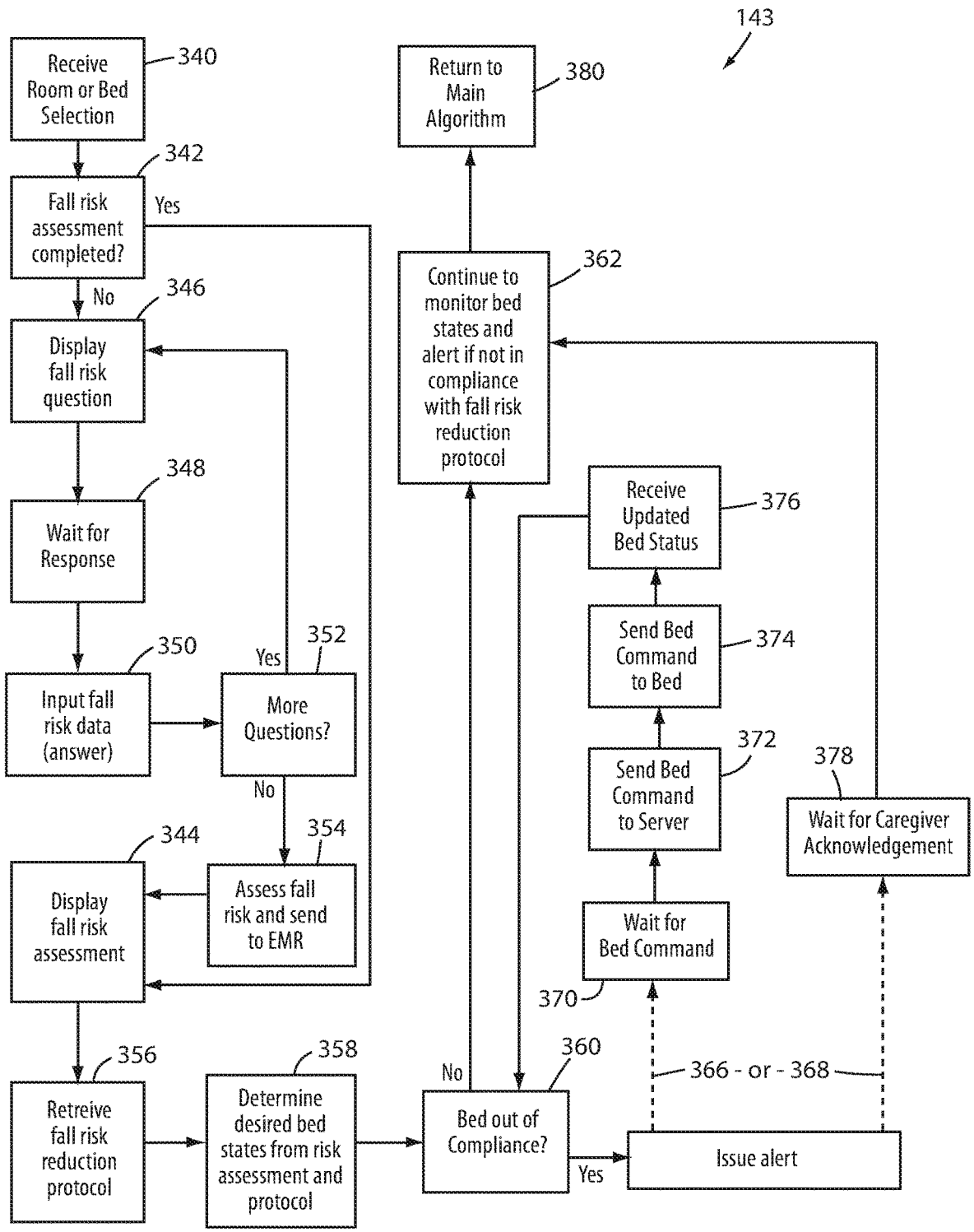
FIG. 18 is a flow diagram of a fall risk reduction algorithm executed by the caregiver assistance application of FIG. 3.

Turning now to the patient fall risk reduction algorithm 143 of caregiver assistance system 106, if a caregiver selects fall task icon 178 (FIGS. 9-17) at step 159 of general algorithm 226 (FIG. 5), caregiver assistance application 124 begins executing fall risk reduction algorithm 143. One example of fall risk reduction algorithm 143 is shown in FIG. 18. Fall risk reduction algorithm 143 begins at a step 340 where caregiver assistance application 124 receives or verifies a room selection or a bed selection. In response to such a room selection or bed selection, caregiver assistance application 124 proceeds to step 342 where it determines if the particular patient assigned to the selected room and/or selected bed has had a fall risk assessment performed or not. Step 342 may be accomplished in several manners. In one particular embodiment, caregiver assistance application sends a request to EMR server 98 requesting the fall risk assessment for the patient assigned to the room or bed identified at step 340. If the EMR server 98 responds that there is no such fall risk assessment currently on file for the patient, fall risk reduction algorithm 143 checks to see if the fall risk assessment is stored elsewhere, such as, but not limited to, data storage 128. If there is no such fall risk assessment stored there, caregiver assistance application 124 may be configured by administrators of the healthcare facility to search in other locations. If no locations contain the fall risk assessment for the particular patient, caregiver assistance application 124 proceeds to step 346. If a fall risk assessment is located for the particular patient, caregiver assistance application 124 proceeds to step 344.

Figure 19:
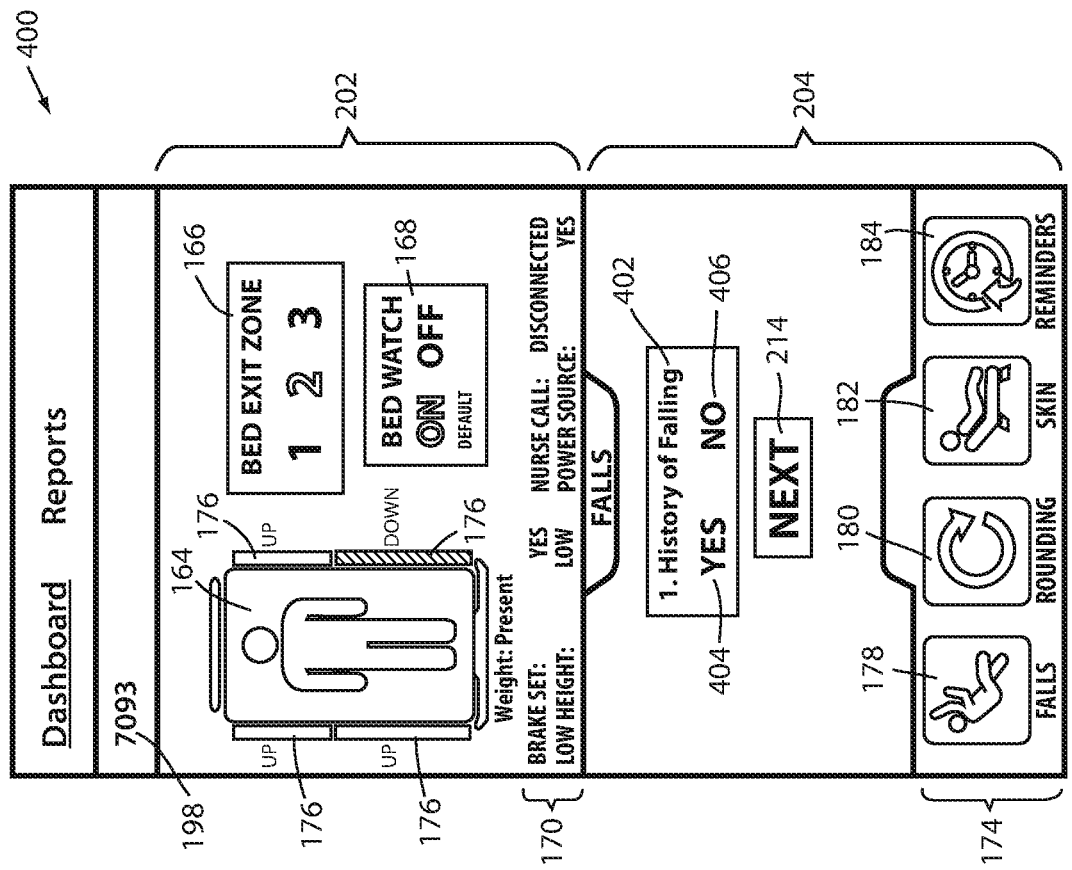
FIG. 19 is an illustrative screenshot of a first fall risk assessment question screen that is displayable on an electronic device of the caregiver assistance system.

When no fall risk assessment has been performed for the patient, caregiver assistance application 124 proceeds from step 342 to step 346. At step 346, caregiver assistance application 124 displays a first fall risk assessment screen 400 that is used to perform a fall risk assessment for the patient assigned to the room or bed identified in step 340. One example of such an initial fall risk assessment screen 400 is shown in FIG. 19. FIG. 19 is the first of six fall risk assessment question screens (FIGS. 19-24) used in one embodiment of caregiver assistance application 124. These six screens are designed to implement the Morse fall risk assessment, which is also sometimes referred to as the Morse fall scale. The Morse fall risk assessment is a numerically scored fall risk assessment that ranks patients into various qualitative categories (e.g. no fall risk, low fall risk, and high fall risk). It will be understood that caregiver assistance application 124 can be configured to implement other fall risk assessments besides the Morse fall risk assessment (e.g. the Hendrich fall risk assessment, the Johns Hopkins fall risk assessment, etc.), and/or it may be supplemented and/or partially modified with other questions. Still other variations may be made to the fall risk assessment by authorized personnel 136 of the healthcare facility, such as by using computer 134 to access and re-configure the settings of caregiver assistance application 124.

Screen 400 includes many of the same elements found in other screens discussed herein, such as, but not limited to, room identifier location 198, top portion 202, bottom portion 204, task menu 174, bed status bar 170, exit detection system status 166, bed watch system status 168, and bed icon 164. Bottom portion 204 differs from the previously described bottom portions in that it includes a first fall risk assessment question 402. The first fall risk question identifies a question intended to be asked by the caregiver of the patient while the caregiver is determining what level of fall risk the patient possesses. Caregiver assistance application 124 displays this first question 402 at step 346 of algorithm 143 (FIG. 18).

The specific first fall risk question 402 displayed at step 346 of algorithm 143 is a question regarding the patient's fall history. Specifically, it is a question of whether or not the patient has ever fallen recently (such as within the last three months, although other time periods can be used). If the patient answers yes, the user touches the "yes" icon 404. If the patient answers no, the user touches the "no" icon. Further, caregiver assistance application 124 assigns a point total to each answer. If the patient answers "yes," application 124 assigns the patient a point value of 25. If the patient answers no, application 124 assigns the patient a point value of zero. Caregiver assistance application 124 sums these point values as the caregiver proceeds through all of the fall risk assessment screens associated with the Morse fall assessment (e.g. FIGS. 19-24). The total score after completing all of the questions is used by caregiver assistance application 124 to determine the patient's qualitative fall risk, as discussed further below.

It will be understood that, although first question 402 is described herein as being the "first" question shown after fall task icon 176 is selected, the particular order of questions displayed by caregiver assistance application 124 may be varied, and the term "first" in the phrase "first fall risk assessment question" is merely used to distinguish the question from other fall risk assessment questions, not to indicate any particular significance to its sequential order.

Returning to fall risk reduction algorithm 143 of FIG. 18, after displaying the first fall risk assessment screen 400 at step 346, caregiver assistance application 124 proceeds to step 348 where it waits for the caregiver to provide an answer to the first fall risk question (e.g. question 402). When the user answers with either a "yes" or a "no" answer, the touching of either the "yes" icon 404 or the "no" icon 406 corresponds to step 350 of algorithm 143. That is, touching either of these icons 404 or 406 inputs the fall risk answer into the electronic device 104, which forwards the data to caregiver assistance application 124. After completing step 350 of algorithm 143, caregiver assistance application 124 proceeds to step 352 where it determines if there are any more fall risk assessment questions that need to be completed as part of the fall risk assessment. Because the example described herein uses the Morse fall risk assessment, which comprises six questions, caregiver assistance application 124 returns at step 352 back to step 346 and displays the next fall risk question (and repeats this another four times).

FIG. 20 illustrates a second fall risk assessment question screen 410. Second fall risk assessment question screen 410 includes a second fall risk assessment question 412 that is answered by the caregiver. Second fall risk assessment question 412 asks if the patient has received more than one medical diagnosis. This may be determined by the caregiver by reviewing the patient's chart or other medical record. If the patient has been assigned two or more medical diagnoses, the caregiver presses the "yes" icon 404. If the patient has only been assigned a single medical diagnosis, the caregiver presses the "no" icon 406. Caregiver assistance application assigns a point value of fifteen to the yes answer and zero to the no answer. After answering the second fall risk assessment question 412, the caregiver presses the "next" icon 214, which brings up third fall risk assessment screen 416 (FIG. 21). The inputting of an answer to second fall risk assessment question 412 corresponds to step 350 of algorithm 143; the pressing of the next icon 214 corresponds to choosing the "yes" option at step 352 of algorithm 143, and the display of third fall risk assessment screen 416 after pressing the next icon 214 corresponds to step 346 of algorithm 143.

Third fall risk assessment question 418 (FIG. 21) comprises three separate sub-questions that are part of the Morse fall risk assessment. In the first sub-question, the caregiver determines if the patient has been assigned to bed rest, or if the patient is able to walk (even with nurse assistance). If either of these conditions is true, the caregiver presses a top icon 420 shown in FIG. 21 that is labeled "bedrest/nurse assist." In response to pressing top icon 420, caregiver assistance application 124 adds a zero value to the patient's fall risk score (which is the sum of the scores previously assigned to the answers to first and second fall risk questions 402 and 412). If neither of these conditions are true, the caregiver determines if the patient needs crutches, a cane, or a walker in order to walk. If the patient needs any of these devices, the caregiver presses a middle icon 422 on screen 416. Middle icon 422 is labeled "crutches/cane/walker" in FIG. 21. In response to pressing middle icon 422, caregiver assistance application 124 add a value of fifteen to the patient's fall risk score. If the patient does not need a crutch, cane, or walker to walk, the caregiver determines if the patient holds onto furniture, or other stable items, when he or she walks. If the patient does this, the caregiver presses a bottom icon 424 on screen 416, which is labeled "furniture" in FIG. 21. In response to pressing bottom icon 424, caregiver assistance application 124 adds a value of thirty to the patient's fall risk score. After choosing one of top, middle, or bottom icons 420, 422, or 424, the caregiver presses the next icon 214, which causes caregiver assistance application 124 to display a fourth fall risk assessment question screen 430, an example of which is shown in FIG. 22.

Fourth fall risk assessment question screen 430 includes a fourth fall risk question 432 displayed in bottom portion 204. Fourth fall risk question 432 asks if the patient has an intravenous (IV) apparatus or heparin lock inserted. If the patient does, the caregiver presses the "yes" icon 404. If the patient does not, the caregiver presses the "no" icon 406. Caregiver assistance application 124 adds a value of twenty to the patient's fall risk score if the caregiver answers "yes" (and adds a value of zero if the caregiver answers no). When the caregiver presses the next icon 214 on screen 430, caregiver assistance application 124 displays a fifth fall risk assessment question screen 440, one example of which is shown in FIG. 23.

Fifth fall risk assessment question screen 440 includes a fifth fall risk question 442 displayed in bottom portion 204. Fifth fall risk question 442 asks the caregiver to assess the patient's gait while he or she walks. More specifically, fifth fall risk question 442 asks the caregiver to qualify the patient's walking gait as one of "normal," "weak", or "impaired." The caregiver characterizes the patient's gait as normal if the patient walks with his or her head erect, his or her arms swinging freely, and takes strides without hesitation. The caregiver characterizes the patient's gait as "weak" if the patient is stooped while walking but is able to lift his or her head while walking without losing his or her balance. The caregiver characterizes the patient's gait as "impaired" if the patient has difficulty rising from a chair, the patient's head is down, and/or he or she watches the ground while walking. An "impaired" assessment may also be assigned if the patient's balance is poor, the patient grasps onto furniture, another person, or some sort of walking aid. Once the caregiver has determined the proper characterization, the caregiver presses the corresponding top icon 444, middle icon 446, or bottom icon 448. Caregiver assistance application 124 adds a value of zero to the patient's fall risk score if the caregiver selects "normal" (top icon 444), adds a value of ten if the caregiver selects "weak" (middle icon 446), and adds a value of twenty if the caregiver selects "impaired" (bottom icon 448). When the caregiver thereafter presses next icon 214, caregiver assistance application displays a sixth fall risk assessment question screen 450, one example of which is shown in FIG. 24.

Sixth fall risk assessment question screen 450 includes a sixth fall risk question 452. Sixth fall risk question 452 asks the patient to assess his or her own abilities at walking (e.g. "do you need assistance walking to the restroom?"). If the patient's answer does not match what the caregiver has observed and determined from the previous questions, the caregiver selects the bottom icon 456 (labeled "forgets limitations" in FIG. 24). If the patient's answer is consistent with what the caregiver has observed and determined from the previous questions, the caregiver selects the top icon 454 (labeled "oriented to own ability"). Caregiver assistance application 124 adds a value of zero to the patient's fall risk score if he or she selects the top icon 454, and adds a value of fifteen if he or she selects bottom icon 456.

After the answer to sixth fall risk assessment question 452 has been provided to caregiver assistance application 124 by the caregiver, caregiver assistance application 124 proceeds to step 354 of algorithm 143 where it analyzes the results of the six questions to determine what level of fall risk the patient possesses. Application 124 does this by summing up all of the values from the six questions of screens 400, 410, 416, 430, 440, and 450, the result of which is the patient's numeric fall risk score. Although different methods of scoring may be used (and/or customized by a particular healthcare facility), in some embodiments caregiver assistance application 124 converts this numeric fall risk score into a qualitative rating, such as zero risk, low risk, moderate risk, and high risk. In one such embodiment, caregiver assistance application assigns a zero risk rating when the numeric fall risk score is zero, assigns a low risk rating if the numeric fall risk score is greater than zero but less than 25; assigns a moderate risk rating if numeric fall risk score is greater than 25 but less than 45; and assigns a high risk rating if the numeric fall risk score is greater than 45. In an alternative embodiment, caregiver assistance application 124 assigns a no risk rating for numeric scores between zero and 25, a low risk rating for numeric scores between 25 and 50, and a high risk for numeric scores greater than 50. Still other qualitative ratings may be used and/or other score ranges may be selected for matching quantitative scores with qualitative scores. Further, the point values assigned to each individual question may also be varied from that described above.

After determining the patient's qualitative fall risk rating, caregiver assistance application sends either or both of the qualitative and quantitative fall risk ratings to the EMR server 98. The fall risk rating is sent by caregiver assistance application 124 along with one or more identifiers that identify which particular patient the just-completed fall risk rating corresponds to. The particular patient to whom the fall risk rating is assigned may be determined in any of the manners previously described, such as by correlating the room number of the patient with the patient's ID, correlating the patient support apparatus's identifier 186 with the room and/or the patient's ID, and/or by performing still other correlations. In this regard, it is to be noted that caregiver assistance application 124 displays the room number (and specific bed bay identifier if the room is a shared room) of the patient to whom the fall risk rating applies during the display of the screens shown in FIGS. 19-24. In the particular example shown, the room number is "7090," and all of the answers to the fall risk questions shown in these screens are assigned to the patient who has been assigned to room 7090. The caregiver therefore is provided with a reminder during the fall risk assessment process of the room number (and thus ultimately the specific patient) to which (or whom) the fall risk assessment is applicable. In some embodiments, caregiver assistance application 124 may be configured to retrieve the actual patient's name from ADT server 98 and display it during the fall risk assessment process so that the caregiver is informed of the specific patient whose fall risk they are assessing. Whether displaying the specific patient name or the specific room number, the caregiver ensures that the fall risk assessment is attributed to the correct individual by assuring that the room number, or patient's name, displayed on the screens 400, 410, 416, 430, 440, and 450 corresponds to the patient (or the patient's room) the caregiver is evaluating for fall risk.

After sending the fall risk assessment and the corresponding patient's name to EMR server 98 at step 354, caregiver assistance application 124 displays the qualitative risk rating at step 344 (FIG. 18). One example of the manner in which the qualitative fall risk rating may be displayed is shown in fall risk screen 460 of FIG. 25. Fall risk screen 460 includes a fall risk warning added to the status location 200. Fall risk screen 460 also includes a summary window 466 displaying multiple pieces of information as a result of the fall risk assessment that was just completed. More specifically, summary window 466 includes both a qualitative fall risk rating identifier 468 and a patient fall risk reduction protocol summary 470. The qualitative fall risk rating identifier 468 corresponds to the qualitative fall risk rating determined after receiving the answers to the six questions shown in FIGS. 19-24. In the particular example shown in FIG. 25, the qualitative fall risk rating identifier 468 is a "high" rating, which indicates that the patient has a high risk of falling.

The fall risk reduction protocol summary 470 summarizes the steps to be taken in order to mitigate the risk of the patient falling. That is, fall risk reduction protocol summary 470 briefly summarizes the fall risk reduction steps contained within fall risk reduction protocol 93 (FIG. 2). In some embodiments, the fall risk reduction protocol 93 is initially set by the manufacturer of caregiver assistance system 106 but is able to be modified by an authorized person 136 of the healthcare facility in order to meet the desires of the healthcare administrators of the particular healthcare facility in which the system 106 installed. In other embodiments, the fall risk reduction protocol 93 may be set by the manufacturer without being customizable, while in still other embodiments, the fall risk reduction protocol 93 may be undefined until the healthcare facility administrators determine its contents.

In general, the fall risk reduction protocol 93 identifies what steps are to be taken by caregivers with respect to the patient support apparatus 20 in order to reduce the risk of the patient falling. Generally speaking, these steps typically include one or more of the following: ensuring the brake on patient support apparatus 20 is activated; placing at least three of the siderails 36 of patient support apparatus 20 in their raised position; arming the exit detection system 46 of the patient support apparatus 20 (including arming a particular zone of the exit detection system 46); lowering the height of litter frame 28 to either its lowest height, or a height that is no taller than a specified threshold; and, in some cases, arming a monitoring system (e.g. the bed watch system identified in the bed watch status indicator 168) that issues an alert if any of the conditions of the fall risk reduction protocol 93 are changed out of their desired states. All of these steps are steps that are taken with respect to fall-risk components of patient support apparatus 20. Fall-risk components are those components of patient support apparatus 20 that have two different states, at least one of which is more likely to reduce the risk of falling. Thus, the fall-risk components include at least the following components of patient support apparatus 20: the siderails 36, the brake, the litter frame 28, exit detection system 46, and the bed watch monitoring system. Fall risk reduction protocol 93 specifies what the desired state is for these fall risk components when the patient has a non-zero fall risk. In most situations, the desired states are those indicated above (e.g. brake on, at least three siderails up, litter frame lowered, exit detection system armed, and bed watch monitoring system (if included) also armed).

In those embodiments where the qualitative fall risk rating has more than two categories (e.g. more than high risk and low risk), fall risk reduction protocol 93 may include different definitions, one for each of the different fall risk rating categories. For example, fall risk reduction protocol 93 may specify that for high fall risk patients, a first set of the fall-risk components must be in their desired states, and that for medium fall risk patients, a second set of the fall-risk components must be in their desired states, wherein the second set is either a subset of the first set, or has some other variation with respect to the first set. In other embodiments, fall risk reduction protocol 93 may be the same for all patients that do not have a zero fall risk rating (e.g. protocol 93 may be the same for high and medium fall risk patients).

Fall risk reduction protocol summary 470 summarizes the desired states for the fall-risk components of the fall risk reduction protocol 93. As shown in FIG. 25, fall risk reduction protocol summary 470 indicates "low bed height," "3 side rails up," "bed exit: zone 2," and "brake set." This means that the particular fall risk reduction protocol 93 shown in this example has identified the litter frame 28, siderails 36, exit detection system 46, and brake as fall-risk components, and that their desired states are a lowered height, or lowest height, for the litter frame 28, a raised position for at least three of the siderails 36, an armed state for exit detection system 46 that is set to zone 2, and an activated brake. Fall risk reduction protocol summary 470 therefore acts as a reminder to the caregiver to ensure that all of these fall-risk components are set to their desired states before the caregiver leaves the room in which patient support apparatus 20 and its associated patient are located.

In order for caregiver assistance application 124 to display the fall risk reduction protocol summary 470 in summary window 466 of FIG. 25, application 124 first retrieves the fall risk reduction protocol 93. This is performed at step 356 of algorithm 143. As indicated in FIG. 2, fall risk reduction protocol 93 may be stored in memory 91. In other embodiments, fall risk reduction protocol 93 may be stored elsewhere. Still further, patient support apparatuses 20 are configured in at least one embodiment to allow a user to make changes to the fall risk reduction protocol 93 using one of the control panels 42. And, as noted, one or more authorized individuals 136 may modify or store fall risk reduction protocol 93 using a computer (e.g. 134) that is in communication with network 74 and caregiver assistance server 90.

Returning to FIG. 18, once caregiver assistance application 124 retrieves the fall risk reduction protocol 93, it determines what the desired states are for each of the fall-risk components. This is accomplished at step 358 of algorithm 143. As noted, the desired states are defined in fall risk reduction protocol 93. After determining these desired states at step 358, caregiver assistance application 124 moves to step 360 where it determines if any of the current states are not in their respective desired states. Caregiver assistance application 124 continuously monitors the states of the fall-risk components of the patient support apparatus 20 within the healthcare facility and uses this repetitively updated state data to determine at step 360 if any of the fall-risk components are not in, or have moved out of, their respective desired states. The updated state data is received from patient support apparatuses 20, which send their state data to caregiver assistance application 124, either directly or, as noted previously, indirectly via patient support apparatus server 86. This state data is alternatively referred to herein as status data, and includes, for example, the current states of the siderails, brake, litter frame, exit detection system, bed watch monitoring system, etc.

If caregiver assistance application 124 determines at step 360 that any of the fall-risk components of the patient support apparatus 20 are not in their desired state according to the patient fall risk protocol 93, it moves to step 364 where it issues an alert, as will be discussed in greater detail below. If it determines at step 360 that none of the fall-risk components of patient support apparatus 20 are out of their desired state, it moves to step 362 where it continues to monitor the fall-risk components and checks to see if they remain in their desired states. From step 362, caregiver assistance application 124 moves to step 380 where it returns to main algorithm 226 (FIG. 5) and allows the caregiver to utilize other functions of caregiver assistance application 124 and/or to display other screens that are not directly related to the patient's fall risk. It is to be noted that the return to main algorithm 226 does not terminate the continuous monitoring of the fall-risk components of the patient support apparatuses, but instead allows this monitoring process to continue in the background. Thus, for example, if the caregiver switches to using the patient rounding function of caregiver assistance application 124 (e.g. by pressing rounding task icon 180) and the patient support apparatus 20 of a patient with a high fall risk has one of its fall-risk components change to an undesired state, caregiver assistance application 124 will still provide the alert of step 364 to the caregiver, even though application 124 may be executing a different algorithm at that particular time.

The alert that is issued at step 364 follows the alerting algorithm 149. Alerting algorithm 149 sends an alert to those electronic device(s) 104 that have been configured to be notified (as defined in local rules 126) for the particular patient support apparatus 20 that has had a fall-risk component moved to an undesired state. The alert is sent to the caregiver's mobile device 104a (and/or to stationary device(s) 104b) regardless of whether or not the caregiver is in the same room, or same ward, as the patient support apparatus 20 that generated the alert. That is, alerting algorithm 149 provides each caregiver with alerts when any of the patient support apparatuses 20 of the patients to whom he or she is assigned have one or more of their fall-risk components change out of their respective desired states. Thus, for example, if a caregiver is currently in, say, room 7030 and that caregiver is assigned to patients in rooms 7031, 7032, and 7033 and those patients are all high fall risks, the caregiver will get an alert on his or her mobile electronic device 104a while they are in room 7030 if any of the patient support apparatuses 20 in rooms 7031, 7032, or 7033 have one or more of their fall-risk components change out of their respective desired states. Further, caregiver assistance application 124 does this for each caregiver who has a mobile electronic device 104a (as well as for all of the stationary electronic devices 104b). As a result, each caregiver is apprised of changes in fall-risk components of the patient support apparatuses 20 used by the particular patients to whom that caregiver is assigned to care for.

Returning to step 364 of algorithm 143, alerting algorithm 149 issues an alert at this step in one or more different manners, depending upon how caregiver assistance application 124 is custom-tailored by an authorized administrator of the healthcare facility, as well as depending upon the particular embodiment of caregiver assistance application 124. In some embodiments of application 124, caregivers access application 124 on their mobile electronic devices 104a by accessing a particular URL using a conventional web browser. In these embodiments of application 124, alerting algorithm 149 may not be able to always provide an alert to the caregiver via the web browser because the caregiver may have the web browser closed, may be visiting a different web page, and/or may not be currently logged into the application 124 via the web browser. Still further, even if the caregiver is currently logged into the caregiver assistance application 124 via the web browser, it may be difficult to guarantee that the caregiver receives the alert because he or she may have the volume turned down on the mobile electronic device 104a and/or he or she may not be looking at the screen at the time the alert is issued.

In order to account for these and other possibilities, alerting algorithm 149 may be configured to issue an alert in some embodiments by sending a text, email, or phone message to the mobile electronic device 104 of the caregiver to whom the alert is directed. Because the mobile electronic device 104a is typically a smart phone or a tablet computer, the text, email, or phone message is delivered to another application that is being executed by the device 104a (e.g. the text app, the email app, or the phone app). Further, the mobile electronic device 104a can be easily set to issue a specific noise, sound, and/or vibration in response to an incoming text, phone call, and/or email. Still further, this specific noise, sound, and/or vibration happens even in those situations where the web browser on the mobile electronic device 104a is closed, or the caregiver is not logged into application 124, or the volume that sounds from websites are played at by the device 104a (e.g. the media volume on a smart phone) have been turned off or set to low. Therefore, alerting algorithm 149 can utilize a separate mobile app on the device 104 for alerting that is independent of the web browsing app on device 104 in order to ensure that alerts are communicated to the caregivers, even when the web browsing app used to gain access to application 124 is turned off on device 104, or is not logged into application 124.

As was also noted previously, in some alternative embodiments, caregiver application 124 is divided into two specific applications: a server application and a mobile device application. In such embodiments, the caregiver does not access caregiver application 124 via a web browser installed on his or her smart device 104a, but instead does so by opening the mobile device application of caregiver application 124. The mobile device application is a specialized app that is downloaded to the mobile electronic device 104a and that is specifically designed to work in conjunction with the server application. In this embodiment, the mobile device application is customized to operate with the specific operating system of the mobile electronic device 104a and, as a result, there may be different versions of the mobile device application that are written for the different operating systems (e.g. an Android version, an iOS version, etc.). Such native applications, offer the advantage of being able to operate in the background and cause the mobile electronic device 104a to issue a sound, vibrate, illuminate one or more lights, etc. in response to an incoming alert, even if the user has not manually opened that native application.

Regardless of the specific manner in which caregiver assistance application 124 issues an alert at step 364 (FIG. 18), algorithm 143 branches to different paths after step 365: a first path 366 and a second path 368. First path 366 allows the user to remotely or locally change the state of the fall-risk component on the patient support apparatus 20 that caused the alert to issue. Second path 368 allows the user to acknowledge the alert without changing the state of the fall-risk component. If the caregiver selects second path 368, caregiver assistance application 124 proceeds to step 378 where it waits for the caregiver to acknowledge the alert without making any changes to the fall-risk component(s) that is out of its desired state. Caregiver assistance application 124 may be configured to accept this acknowledgement in several different manners such as, but not limited to, displaying an "acknowledge" or "ignore" icon that must be touched by the caregiver to acknowledge the alert, or otherwise requiring the caregiver to take some positive action with the mobile electronic device 104a that indicates that the caregiver received and is aware of the alert. Once the alert is received by caregiver assistance application 124, algorithm 143 proceeds to step 362 and operates in the manner previously discussed.

If the caregiver wishes to change the state of the fall-risk component that is no longer in its desired state, the caregiver can elect to follow first path 366 (FIG. 18). First path 366 allows the caregiver to change the state of the fall-risk component to its desired state either locally or, in some cases, remotely. To change the state locally, the caregiver must be present in the room in which the alerting patient support apparatus 20 is located. The caregiver makes the local change by utilizing one or more of the control panels 42 of the patient support apparatus 20. To make the change remotely, the caregiver uses mobile electronic device 104a to send a command to the patient support apparatus 20 to change the fall-risk component back to its desired state. In many embodiments, only commands that involve no physical movement on the patient support apparatus 20 are allowed to be carried out remotely, such as arming the exit detection system, arming the bed watch monitoring system, etc.

In order to remotely change the state of the fall-risk component using mobile electronic device 104a (or stationary electronic device 104b), caregiver assistance application 124 waits to receive a command for the patient support apparatus at step 370 (FIG. 18). Once the command is received, the command is sent by the electronic device 104 to the caregiver assistance server 90 at step 372. When it is received by the caregiver assistance application 124 operating on server 90, application 124 forwards the command to the appropriate patient support apparatus 20 at step 374. Thereafter, the patient support apparatus 20 implements the command and sends an updated set of data regarding its fall-risk components, which are received by caregiver assistance application 124 at step 376. Using this updated set of data, caregiver assistance application 124 returns back to step 360 where it checks to see if the patient support apparatus 20 has all of its fall-risk components in their desired states. From step 360, caregiver assistance application 124 proceeds in the manners previously described.

When mobile electronic device 104a is used to send a command to change the state of a fall-risk component of a patient support apparatus 20, it knows which specific patient support apparatus 20 to send the command to based upon the room number (and/or patient name) displayed in status location 200. That is, whatever room number, bed bay identifier, and/or patient identifier is displayed in status location 200 at the time the command is sent identifies where the command will be sent. When caregiver assistance application 124 receives the command at server 90, it knows which patient support apparatus 20 to send it to based on its knowledge of which patient support apparatuses 20 are assigned to which rooms, bed bays, and/or patients.

It will be noted that the monitoring of the states of the fall-risk components of the patient support apparatuses 20 that occurs at steps 360 and 362 of algorithm 143 may involve more monitoring than is performed by the bed watch monitoring system. That is, in at least one embodiment, the patient fall risk protocol 93 may specify that the bed watch monitoring system is turned on for high fall risk patients. In this case, algorithm 143 automatically monitors whether the bed watch monitoring system is turned on or off for those patient support apparatuses 20 to whom high fall risk patients have been assigned, and if it is off, algorithm 143 issues an alert. Thus, the fall risk reduction protocol 93 can provide an additional layer of monitoring beyond what the bed watch monitoring feature offers: it can monitor the bed watch monitoring feature itself (which does not monitor itself).

It will also be noted that caregiver assistance application 124 also passively monitors all of the states of various components of the patient support apparatuses 20, regardless of whether a patient is a high fall risk or not, and regardless of whether the patient has even been assessed for fall risks or not (and also regardless of whether the bed watch monitoring system is armed or disarmed). The results of this passive monitoring are displayed in top portion 202 of the screen shots shown herein (e.g. FIGS. 19-26). This monitoring provides information to the caregiver of the current state of the patient support apparatus 20 so that the caregiver can remotely know the states of all of the patient support apparatuses 20 which are being used with his or her assigned patients. Further, this passive monitoring may involve the monitoring of a different set of components than the fall-risk components discussed above, such as, but not limited to, whether the patient support apparatus 20 is currently plugged into an electrical outlet, whether the nurse call system cable between the patient support apparatus 20 and the nurse call system is connected or disconnected, etc.

In some embodiments, when caregiver assistance application 124 issues an alert due to a fall-risk component of a patient support apparatus 20 moving out of its desired state, the alert may include a graphical indication of the fall-risk component that has moved out of its desired state. For example, in all of the screens shown in FIGS. 19-27, caregiver assistance application 124 includes a bed icon 164. If any of the siderails are moved out of their desired position, caregiver assistance application 124 may graphically indicate this by changing the color of, or otherwise changing the visual appearance of, the siderail icon 176 corresponding to the siderail 36 that has moved out of its desired state. Additionally, if the height of the litter frame 28 moves above its desired height, caregiver assistance application 124 may change the color or appearance of the top of the litter frame shown in bed icon 164 (e.g. the top portion of the bed icon 164 that surrounds the patient icon). If either the exit detection system 46 or the bed watch monitoring system are changed to an undesired state, caregiver assistance application 124 may graphically indicate this by highlighting, or otherwise changing the appearance of, exit detection system status indicator 166 or bed watch status indicator 168. If the brake moves out of its desired state, the portion of bed status bar 170 indicating the brake status may be highlighted and/or otherwise changed visually. Still other graphical changes may be made for alerts involving a fall-risk components that are moved out of its desired state.

In at least one embodiment, caregiver assistance application 124 allows a user to make changes to the exit detection system aspects of the patient fall risk reduction protocol 93 for a particular patient. More specifically, in at least one embodiment, caregiver assistance application 124 allows a caregiver to override the exit detection system zone that is specified by the fall risk reduction protocol 93. For example, in many embodiments, the fall risk reduction protocol 93 specifies that the exit detection system 46 is armed for a high fall risk patient, and that zone 2 (the middle sensitive zone) is chosen. If the caregiver wishes to arm a different zone, however, caregiver assistance application 124 allows the caregiver to do with without causing an alert when application 124 detects that the incorrect zone is armed at step 360 of algorithm 143.

Two examples of this customized zone selection are shown in FIGS. 26 and 27. In the screenshot 480 of FIG. 26, the caregiver has selected zone 1 of the exit detection system 46 and caregiver assistance application 124 has displayed a warning window 482 thereon. Warning window 482 notifies the caregiver that zone 2, not zone 1, is the zone specified by patient fall reduction protocol 93. If the user wishes to select zone 1 instead of zone 2, however, the user is free to do so by pressing the confirm icon 484. If the user presses the confirm icon 484, caregiver assistance application 124, in at least one embodiment, updates the fall risk reduction protocol 93 for that particular patient only such that no alerts are issued at step 364 because of zone 1 being armed instead of zone 2. In this embodiment, caregiver assistance application 124 automatically changes the fall risk reduction protocol 93 back to zone 2 if a new patient is assigned to that particular patient support apparatus 20, or if the user subsequently switches exit detection system 46 from zone 1 back to zone 2 for that particular patient support apparatus 20.

FIG. 27 illustrates a similar situation where the caregiver wishes to arm zone 3 of exit detection system 46 instead of zone 2. As with the situation shown in FIG. 27, caregiver assistance application 124 displays a warning window 492 on screen 490 that informs the caregiver that zone 2 is the zone specified by fall risk reduction protocol 93. If the user wishes to override this zone choice, however, the user is free to press the confirm icon 494, in which case caregiver assistance application 124 updates the fall risk reduction protocol 93 for that particular patient and no longer issues alerts due to zone 3 being selected instead of zone 2. Caregiver assistance application 124 automatically switches the protocol 93 back to zone 2 for that particular patient support apparatus 20 if a new patient is assigned to it or the caregiver switches exit detection system 46 back to zone 2 from zone 3 on that particular patient support apparatus 20.

In addition to the alerts discussed above with respect to rounding algorithm 140 and fall risk reduction algorithm 143, alerting algorithm 149 is configured to alert caregivers whenever a status of any of the patient support apparatuses 20 assigned to the caregiver changes while the bed watch feature is armed. Caregiver assistance application 124 may further be configured to alert the corresponding caregiver whenever any patient support apparatus 20 alert is issued by any of the patient support apparatuses 20 to which the caregiver is assigned (e.g. a patient exit alert, a cord-out alert, etc.). Such alerts may arise when the caregiver is using caregiver assistance application 124 for other purposes, such as one of the other tasks identified in task menu 174, or such alerts may arise while the caregiver is engaged in other tasks that don't involve the use of an electronic device 104. As noted, such alerts are communicated to the caregiver, in at least one embodiment, by sending a text, email, and/or automated phone call to the particular caregiver associated with the patient support apparatus 20 that is issuing the alert. Further, alerting algorithm 149 is configured to allow users to choose how such alerts are issued, in at least some embodiments. Caregivers may therefore receive a text sent to their mobile electronic device 104a (or another phone capable of receiving texts), for example, if the exit detection system 46 of a patient support apparatus 20 detects a patient exit, or if the nurse call cable is unplugged, or any other status changes that warrant an alert. The mobile electronic device 104a responds to the received text (or email or phone call) with a beep, the illumination of one or more lights, or in any other manner dictated by that particular caregiver's preferences.

Structural modifications may also be made to caregiver assistance system 106. For example, although caregiver assistance system 106 has been described herein as utilizing a caregiver assistance application 124 executed on caregiver assistance server 90 and accessed by electronic devices 104 having conventional web-browser applications stored thereon, caregiver assistance system 106 may be modified to include one or more native applications that execute on the electronic devices 104a or b themselves. In some of these modified embodiments, the caregiver does not need to open up the web-browser to access caregiver assistance application 124, but instead opens up a local caregiver assistance software application on the electronic device 104 that interacts with the caregiver assistance application 124 being executed on caregiver assistance server 90. In such embodiments, it may be easier to provide alerts to the caregiver by having the electronic device vibrate, emit an audible sound, and/or illuminate one or more lights on the device. Such alerts may be more difficult to communicate to a caregiver when caregiver assistance system 106 is implemented using browser-connected electronic devices 104, particularly if the caregiver has the browser application closed and/or running in the background and/or is not looking at the information currently being displayed on the screen of the electronic device 104. Such native applications may be programmed for execution with the Android or iOS operating systems, or still other operating systems utilized by the electronic device 104.

It will be understood by those skilled in the art that, although caregiver assistance application 124 has been primarily described herein with reference to a single caregiver using a single electronic device 104, caregiver assistance application 124 is not limited to use by only a single caregiver and/or a single electronic device 104. Further, caregiver assistance application 124 is not limited to use with only a single patient support apparatus 20 or a single patient. Instead, caregiver assistance application 124 is configured to be used, if desired, with all of the patient support apparatuses 20 within the healthcare facility, as well any or all of the caregivers within the healthcare facility. Such use of caregiver assistance application 124 by multiple caregivers can occur simultaneously. That is, multiple caregivers may be logged into caregiver assistance application 124 at the same time. In such cases, caregiver assistance application 124 is configured to display the room, patient, and/or patient support apparatus information discussed above for the set of rooms, patients, and/or patient support apparatuses 20 assigned to that particular caregiver. In other words, each caregiver (other than those with administrative access) is only able to view the room, patient, and patient support apparatus information for the rooms and/or patients assigned to that particular caregiver. Unless otherwise configured by an authorized individual, alerts associated with those patients, rooms, and/or patient support apparatuses 20 are only communicated by caregiver assistance application 124 to the mobile electronic device 104a associated with that caregiver (and, in some cases, to the stationary electronic device 104b that is associated with that particular room or patient).

Stationary electronic devices 104b are typically not used to perform rounding tasks and/or patient fall risk assessments because they cannot be carried with the caregiver to a patient's room, and thus are difficult to use for capturing images or assessment information and/or performing other tasks in the patient's presence. Nevertheless, stationary electronic devices 104b are capable of displaying all of the screens previously described and associated with caregiver assistance application 124, and receiving all of the data that is input on these screens, including not only answers to rounding and/or assessment questions, but also commands to change components on the patient support apparatuses 20. Further, authorized individuals 136 can configure caregiver assistance application 124 as they see fit with respect to what, if any, alerts are displayed on the stationary electronic devices 104b. For example, if a particular stationary electronic device 104b is associated with a particular wing of the healthcare facility, then the authorized individual 136 may configure caregiver assistance application 124 to notify the stationary electronic device 104b whenever any alert from any room or patient support apparatus 20 within that wing is issued. This can be configured even if the different rooms and/or patient support apparatuses 20 are assigned to different caregivers. As a result, caregiver A may receive alerts on his or her mobile electronic device 104a for a first set of rooms in that particular wing; caregiver B may receive alerts on his or her mobile electronic device 104a for a second set of rooms in that particular wing; and the stationary electronic device 104b associated with that wing may receive alerts for both the first and the second sets of rooms (and any other rooms in that particular wing). Still other variations are possible.

The data flows of caregiver assistance system 106 between caregiver assistance server 90, patient support apparatuses 20, and electronic devices 104 are illustrated in greater detail in FIG. 2. As shown therein, patient support apparatuses 20 transmit patient support apparatus messages 310 to patient support apparatus server 86 (or directly to caregiver assistance server 90) via network transceivers 60 and wireless access points 76. The patient support apparatus data contained within messages 310 includes such things as the status of the exit detection system 46 (armed or disarmed), the status of the siderails 36 (up or down), the status of the electrical power cord 102 (plugged in or not), the status of the nurse call cable 78 (plugged in or not), the status of the brake (on or off), the height of the litter frame 28, the status of the bed watch monitoring system, any existing alerts, and/or other data about patient support apparatus 20.

Caregiver assistance server 90, after receiving the data in these messages, transmits outbound messages 312 to selected ones of the electronic device 104 (FIG. 2). The content of the outbound messages 312 includes all or selected portions of the patient support apparatus data received via messages 310. Most of this patient support apparatus data is displayed on the screens in top portion 202. The outbound messages 312 also include the data content for the display screens shown as part of general algorithm 226, rounding algorithm 140, and fall risk reduction algorithm 143. This data content includes, among other things, the rounding questions that are identified in the rounding display screens of FIGS. 10-13, the fall risk assessment questions that are displayed in the fall risk screens of FIGS. 19-24, any reminders, room numbers, alerts, and other data discussed herein.

Caregiver assistance server 90 receives inbound message 314 from the electronic devices 104 in which it is in communication (FIG. 2). Inbound messages 314 include rounding data, patient support apparatus commands, fall-risk assessment data, and/or verification data. The rounding data includes the answers and/or acknowledgements corresponding to the rounding questions displayed on first through fourth rounding screens 190, 220, 230, and 240, and the fall-risk assessment data includes the answers to the fall risk questions that are asked as part of algorithm 143. The patient support apparatus commands include any commands input by the caregiver into the electronic device 104 to change a state of the corresponding patient support apparatus 20. As discussed previously, such commands include commands to arm exit detection system 46 and/or commands to arm a bed watch system, as well as other commands. Inbound messages 314 may also include verification data, which is data gathered by mobile electronic device 104a that verifies the actual physical presence of the caregiver adjacent the patient support apparatus whose patient the caregiver is performing rounding duties for. More specifically, the verification data includes the images of the QR code, bar code, patient support apparatus, and/or caregivers that are captured by the mobile electronic device 104a and sent to caregiver assistance application 124, as was previously described above with respect to FIGS. 15-17.

Figure 28:
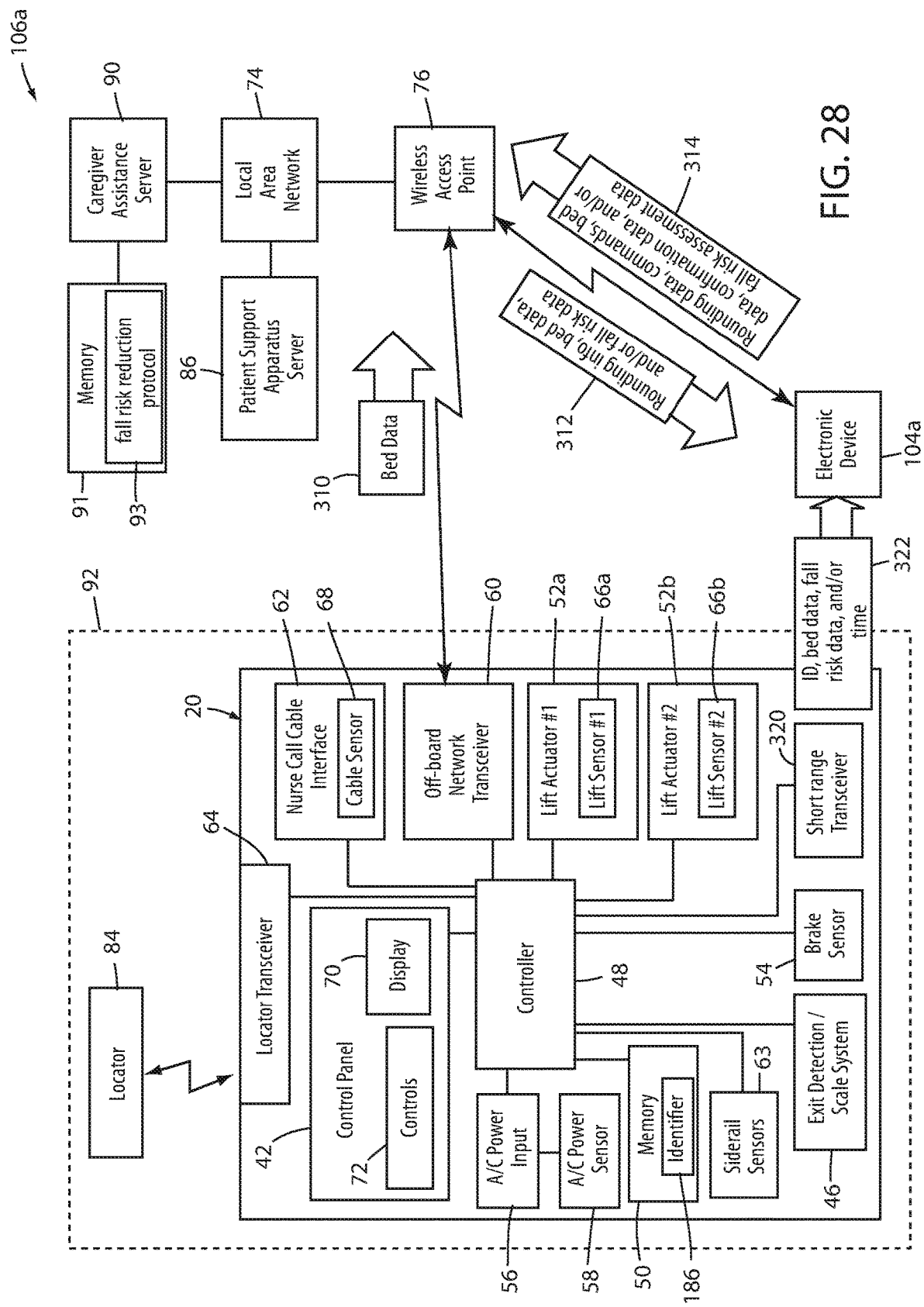
FIG. 28 is a block diagram of a second embodiment of the caregiver assistance system of the present disclosure showing a detailed set of components of a patient support apparatus usable therein, as well as a portion of a local area network in which the patient support apparatus is in communication.

It will be understood that the data flows illustrated in FIG. 2 may be modified significantly. For example, FIG. 28 illustrates a caregiver assistance system 106a according to another embodiment of the present disclosure. Caregiver assistance system 106a differs from caregiver assistance system 106 of FIG. 2 in that caregiver assistance system 106a includes different flows of messages sent between the caregiver assistance server 90, the mobile electronic devices 104a, and the patient support apparatuses 20. Caregiver assistance system 106a also differs from caregiver assistance system 106 of FIG. 2 in that it includes modified patient support apparatuses 20a that, unlike patient support apparatuses 20, include a short range transceiver 320. Further aspects of caregiver assistance system 106a are described below.

Patient support apparatuses 20a of caregiver assistance system 106a include all of the same components of patient support apparatuses 20 of caregiver assistance system 106. Those common components have been labeled with common numbers in FIG. 2 and, unless explicitly stated to the contrary below, the description of those components previously made above is equally applicable to these components. Caregiver assistance system 106a differs from caregiver assistance system 106 primarily in the source of the verification data that is sent by electronic device 104 to caregiver assistance server 90 for use with rounding algorithm 140. As noted, such verification data verifies that the caregiver was actually physically present adjacent a patient support apparatus 20a when he or she performed his or her rounding tasks. In system 106a, the verification data comes not from the images captured and illustrated in FIGS. 15-17, but from the short range transceiver 320 that is built into patient support apparatus 20a.

Short range transceiver 320 (FIG. 28) is adapted to wirelessly communicate with electronic devices 104 over a relatively short range. The short range is, in some embodiments, no larger than the typical size of a healthcare facility room such that, when a caregiver leaves a particular room, the caregiver's mobile electronic device 104a is no longer within range of the short range transceiver 320, and therefore no longer able to communicate with the short range transceiver 320. In some embodiments, short range transceiver 320 is an infrared transceiver adapted to communicate in line-of-sight situations with a corresponding infrared transceiver built into the mobile electronic device 104a. In other embodiments, short range transceiver 320 is a near field transceiver adapted to communicate with a near field transceiver built into mobile electronic device 104a. In still other embodiments, short range transceiver 320 is an RF transceiver having a relatively small power output such that communications are limited to within a short range of patient support apparatus 20a. Such RF transceivers may include, but are not limited to, Bluetooth transceivers.

Regardless of the specific short range transceiver 320 utilized by patient support apparatus 20a, controller 48 of patient support apparatus 20a is configured to transmit one or more patient support apparatus messages 322 using transceiver 320 to a nearby mobile electronic device 104a (FIG. 28). The messages 322 contain one or more of the following pieces of information: the unique identifier 186 of the corresponding patient support apparatus 20a; the current time; and/or sufficient patient support apparatus data to indicate whether the current status of the patient support apparatus 20 is in compliance with its desired settings or not. This information is transmitted periodically and repetitively in some embodiments of patient support apparatus 20a. In other embodiments, this information is transmitted only in response to an interrogation signal received from a mobile electronic device 104a. In still other embodiments, this information may be transmitted both repetitively and in response to interrogation signals.

Mobile electronic device 104a receives message(s) 322 when it is positioned within the vicinity of patient support apparatus 20a (FIG. 28). Mobile electronic device 104a uses the message 322 for carrying out the verification and/or compliance steps of rounding algorithm 140, and/or for carrying out one or more aspects of fall risk reduction algorithm 143. With respect to patient rounding, in some embodiments, messages 322 are sent and captured by mobile electronic device 104a as part of step 252 of algorithm 140. The sending of messages 322 to mobile electronic device 104a takes the place of, or in some embodiments supplements, the capturing of image data that otherwise occurs at step 252 of algorithm 140. Mobile electronic device 104a uses the messages 322, particularly the patient support apparatus ID and/or time, to verify that it was physically present adjacent patient support apparatus 20a when the rounding occurred. This verification is handled, in some embodiments, internally via the programming of caregiver assistance application 124 such that the caregiver does not need to enter any information, or take any manual steps (other than positioning mobile electronic device 104a within range of transceiver 320) for this verification data to be received by mobile electronic device 104a and forwarded to caregiver assistance application 124. In other embodiments, in order to prevent a user (or electronic device 104a) from modifying the data contained within messages 322, the data is encrypted with an encryption algorithm that caregiver assistance application 124 is able to decrypt, but not mobile electronic device 104a. In still other embodiments, patient support apparatus 20a may be further modified to send a second message to caregiver assistance application 124 via network transceiver 60 whenever it transmits message 322 via short range transceiver 320. This second message confirms to caregiver assistance application 124 that message 322 was sent and, in some embodiments, contains the same information. If caregiver assistance application 124 does not receive this second message, it does not accept the verification data sent from mobile electronic device 104a.

With respect to patient fall risk reduction algorithm 143, patient support apparatus messages 322 may identify the particular patient support apparatus 20 to mobile device 104a (and thus caregiver assistance application 124) that the caregiver is currently positioned next to. This allows caregiver assistance application 124 to automatically, in at least some embodiments, bring up a screen that corresponds to that particular patient support apparatus 20 and the patient assigned thereto. Thus, if the caregiver wishes to perform a fall risk assessment for a particular patient, he or she merely needs to walk within range of messages 322 and press the fall task icon 178. In response to pressing fall task icon 178, caregiver assistance application 124 automatically displays screen 400 (or a screen like it) with full knowledge of which patient (and/or which patient support apparatus 20) the answers to the fall risk questions are applicable to. The caregiver therefore is relieved of the task of manually identifying a specific room or a specific patient before proceeding to the fall risk assessment process of fall risk reduction algorithm 143. Instead, caregiver assistance application 124 uses the specific patient support apparatus identifier 186 received within message 322 to determine which patient the subsequent fall risk assessment applies to. Fall risk reduction algorithm 143 may also use data from messages 322 for other portions of the fall risk reduction algorithm 143.

Regardless of whether they are used by rounding algorithm 140 and/or fall risk reduction algorithm 143, messages 322 (FIG. 28) also include patient support apparatus data. In some embodiments, the patient support apparatus data only includes an indicator indicating whether the patient support apparatus 20 is in a compliant or non-compliant state. In other embodiments, the patient support apparatus data includes actual data about the state of each of the components of the patient support apparatus 20 and the determination of whether the patient support apparatus is in a compliant or non-compliant state is made by caregiver assistance application 124 based on the data communicated in message 322, as well as data stored in local rules repository 126 defining the criteria for compliance. In either embodiment, the patient support apparatus data sent in message 322 is used by algorithm 140 to perform step 254 (FIG. 6) and/or by fall risk reduction algorithm 143 to perform step 360 (FIG. 18).

In some embodiments, message 322 may also include the current time. If included, this time information is also forwarded to caregiver assistance application 124. Caregiver assistance application 124 uses this time information to confirm the time that the caregiver was actually present at the patient's bedside when a rounding task was completed (or, in some embodiments, to record when another task was completed, such as a fall risk assessment). This time information is sent to EMR server 98 in some embodiments so that the time at which the rounding task, or other task, is recorded in the patient's electronic medical record. In other embodiments, patient support apparatus 20 may skip transmitting a time in message 322 and mobile electronic device 104a may append a time of receipt of message 322 in the data it sends to caregiver assistance application 124. As yet another alternative, both patient support apparatus 20 and mobile electronic device 104a may omit sending any time information and caregiver assistance application 124 can instead record the time at which it receives the inbound messages 314 from mobile electronic device 104a. In any of these embodiments (which may be wholly or partially combined), the time is used by caregiver assistance application 124 to determine and/or record when the caregiver completed his or her rounding task (or other task) for the particular patient assigned to the patient support apparatus 20 that sent message 322.

Figure 29:
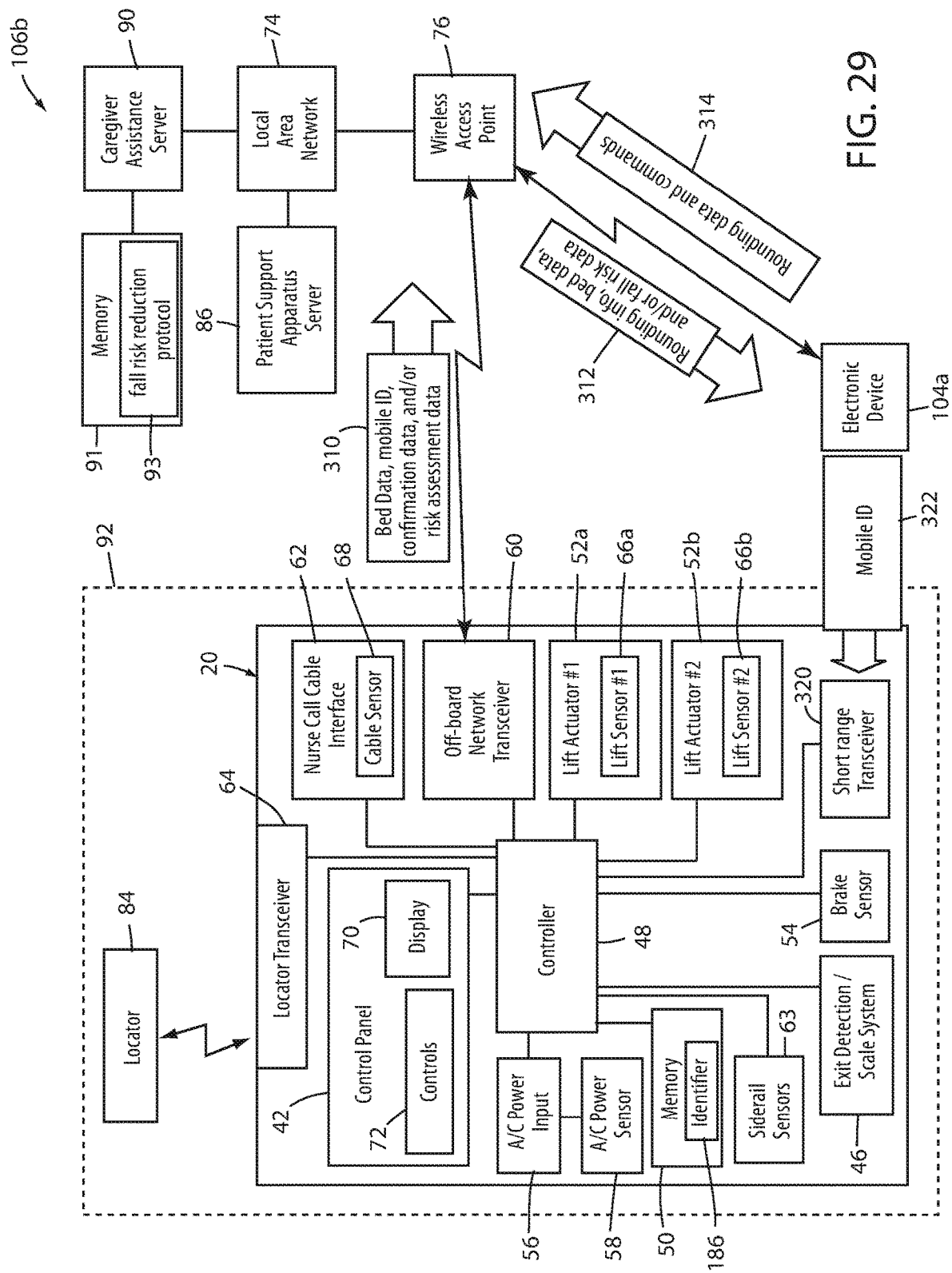
FIG. 29 is a block diagram of a third embodiment of the caregiver assistance system of the present disclosure showing a detailed set of components of a patient support apparatus usable therein, as well as a portion of a local area network in which the patient support apparatus is in communication.

FIG. 29 illustrates a caregiver assistance system 106b according to another embodiment of the present disclosure. Caregiver assistance system 106b differs from caregiver assistance systems 106 and 106a of FIGS. 2 and 28, respectively, in that mobile electronic device 104a sends an electronic device message 324 to patient support apparatus 20a that is used by caregiver assistance system 106b for one or more purposes. With respect to rounding algorithm 140, message 324 is used by patient support apparatus 20 to verify that the caregiver was present at the patient's bedside during the caregiver's performance of his or her rounding duties. With respect to fall risk reduction algorithm 140, messages 324 may be used to correlate the fall risk assessment to a specific patient or patient support apparatus 20, or it may be used to send a command to the patient support apparatus 20 directly in order to change a state of any of the fall-risk components of patient support apparatus 20.

As shown more clearly in FIG. 29, mobile electronic device 104a is adapted in caregiver assistance system 106b to send out a short range message 324 to a nearby short-range transceiver 320 of patient support apparatus 20a. The short range message 324 is sent as a result of any one or more of the following: in response to a user manipulating an input on mobile electronic device 104a, an expiration of a periodic time interval, an interrogation signal sent from short range transceiver 320 of patient support apparatus 20a, a signal from RTLS server 100 to mobile electronic device 104a indicating that it is currently in a room with one or more patient support apparatuses 20a, a combination of one or more of these triggering conditions, and/or in response to still other triggering conditions.

The content of electronic device message 324 includes a unique identifier that uniquely identifies the mobile electronic device 104a. This may be a serial number of the device 104a, a MAC address, or some other identifier that distinguishes that particular mobile electronic device 104a from other mobile or stationary electronic devices 104a, 104b that are part of system 106b, and/or other electronic devices that are not part of system 106b but which may utilize the same protocol and/or communication channel as transceiver 320.

As with patient support apparatus message 322 (FIG. 28), electronic device message 324 may be sent via infrared, near field communication, low power RF (e.g. Bluetooth), or some other protocol that limits the range of message 324 such that it is not detected by patient support apparatuses 20a that are positioned outside of the room in which the caregiver is currently located.

In response to receiving the electronic device message 324, controller 48 of patient support apparatus 20a forwards a message to caregiver assistance application 124 informing application 124 of the receipt of the message 324, including the mobile ID contained within the message 324. Caregiver assistance application 124 uses the receipt of this information at step 252 of rounding algorithm 140. That is, caregiver assistance application 124 waits for receipt of this message from patient support apparatus 20a and, if it does not receive it, it concludes that there has been no verification of the caregiver's presence beside the patient when performing his or her rounding task. If the caregiver assistance application 124 receives the message, then it concludes that there has been verification and proceeds to step 254 of algorithm 140. In some embodiments, caregiver assistance application 124 proceeds from step 250 directly to step 254 and doesn't wait for the receipt of the mobile ID from patient support apparatus 20. In such embodiments, caregiver assistance application 124 checks to see if the mobile ID has been received from the patient support apparatus 20a after performing step 254 and/or the steps of path 280 and/or 282 have been completed (but prior to step 256).

In the caregiver assistance system 106b of FIG. 29, mobile electronic device 104a does not need to include any verification data in the inbound messages 314 it sends to caregiver assistance server 90 because such verification data is contained within the patient support apparatus messages 310 sent by network transceiver 60. In some embodiments, the verification data contained within message 310 includes only the mobile electronic device ID, while in other embodiments, the verification data includes additional information, such as, but not limited to, the time at which the electronic device message 324 was received. Of course, all of the messages 310 sent from patient support apparatus 20a (and patient support apparatuses 20) via network transceiver 60 to caregiver assistance server 90 include the patient support apparatus ID.

In the caregiver assistance system 106b of FIG. 29, the messages 314 sent by mobile electronic device 104a to caregiver assistance server 90 may omit patient support apparatus data that is used to determine whether the patient support apparatus 20a is in a compliant state or not. This information may be omitted because patient support apparatus 20a sends its status data directly via messages 310, and this status data is used by caregiver assistance application 124 to determine at step 254 whether the patient support apparatus 20a is in a compliant state or not.

Caregiver assistance system 106b of FIG. 29 may be modified to replace the short range communication between mobile electronic device 104a and transceiver 320 of patient support apparatus 20a. In such modified embodiments, rather than having a wireless signal transmitted to patient support apparatus 20a to verify the caregiver's presence adjacent the patient support apparatus 20a, the patient support apparatus 20a is modified to accept a physical input from the caregiver, such as a button, switch, or the like, that the caregiver presses during the rounding task. The physical input may be included as an icon on a touchscreen of patient support apparatus 20a, or it may be a dedicated control, or it may some combination of the two. As an alternative to a physical input, a wireless signal may be utilized for verification purposes that does not involve mobile electronic device 104a. For example, the input may involve a caregiver swiping a card with a magnetic strip along a card reader built into patient support apparatus 20a, or it may involve positioning a near field communication card adjacent a near field communication transceiver built into patient support apparatus 20a. Still other variations are possible.

Regardless of how the input to patient support apparatus 20 is implemented, when the caregiver physically or wirelessly activates the verification control on patient support apparatus 20a, controller 48 sends a message 310 to caregiver assistance application 124 that includes verification data indicating that the caregiver was present adjacent patient support apparatus 20a. The message 310 may include a time at which the verification input was activated by the caregiver. In this modified embodiment of system 106b, short range transceiver 320 of patient support apparatus 20a may be omitted and/or modified, and mobile electronic device 104a need not include a transceiver that is compatible with transceiver 320.

It will be noted that, as shown in FIG. 29, caregiver assistance system 106b does not show electronic device 104 forwarding any fall risk assessment data to caregiver assistance server 90 via wireless access point 76. Although caregiver assistance system 106b can be configured to forward such data in the manner previously described, caregiver assistance system 106b can alternatively be configured such that the fall risk assessment data gathered at steps 346 through 352 of algorithm 143 is gathered via a user interface or control panel on patient support apparatus 20. Thus, instead of displaying screens such as those shown in FIGS. 19-24 on the display of electronic device 104, caregiver assistance application 124 can be configured to work with a patient support apparatus 20 that displays screens like those shown in FIGS. 19-24 on one of its own displays (e.g. display 70). The answers to those questions are then sent by patient support apparatus 20 to caregiver assistance application 124 and used in the manner specified by algorithm 143. In this particular embodiment, the patient support apparatus 20 is used to perform the fall risk assessment portion of algorithm 143, and the electronic device 104 is used to receive and display alerts if the fall risk reduction protocol is not being followed. In still another alternative embodiment, the fall risk assessment questions may be displayed and answered on either or both of display 70 of patient support apparatus 20 or the display of the electronic device 104.

Figure 30:
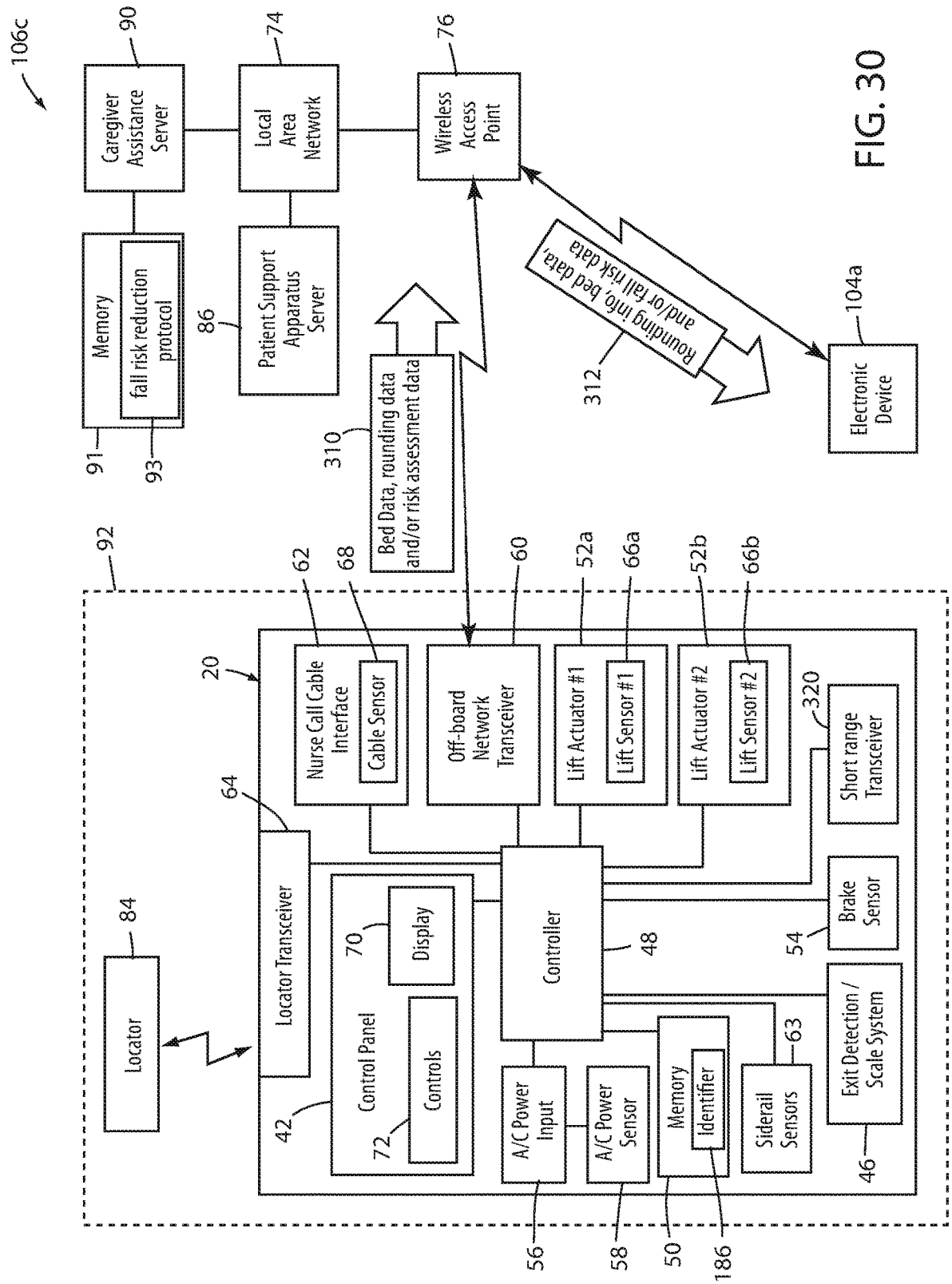
FIG. 30 is a block diagram of a fourth embodiment of the caregiver assistance system of the present disclosure showing a detailed set of components of a patient support apparatus usable therein, as well as a portion of a local area network in which the patient support apparatus is in communication.

FIG. 30 illustrates another caregiver assistance system 106c according to yet another embodiment of the present disclosure. Caregiver assistance system 106c differs from caregiver assistance systems 106, 106a, and 106b of FIGS. 2, 28, and 29, respectively, in that mobile electronic device 104a does not send any rounding data, fall risk assessment data, commands, and/or patient support apparatus data back to caregiver assistance application 124. Instead, such data is communicated to caregiver assistance server 90 via patient support apparatus 20a. Caregiver assistance system 106c also differs from the other caregiver assistance systems 106, 106a, and 106b in that it can utilize either patient support apparatus 20 or patient support apparatus 20a. That is, the patient support apparatuses usable with caregiver assistance system 106c can include short range transceiver 320, or they may omit short range transceiver 320. Indeed, in some embodiments, caregiver assistance system 106c may be implemented in a healthcare facility wherein some of the patient support apparatuses includes short range transceiver 320 and others do not.

In the embodiment of FIG. 30, system 106c uses mobile electronic devices 104a (and/or stationary electronic devices 104b (not shown)) primarily to display information regarding the patient support apparatuses 20 and/or 20a, as well as, in some embodiments, to display rounding information and/or fall risk protocol compliance information. The caregiver, however, does not utilize mobile electronic device 104a (or device 104b) to input rounding information, verification data, fall risk assessment data (e.g. answer to fall risk questions), and/or compliance data. Instead, all of this data is entered via a user interface of patient support apparatus 20 or 20a. Stated alternatively, in the embodiment of caregiver assistance system 106c of FIG. 30, all of the screens shown in at least FIGS. 10-14 are adapted to be displayed on the display 70 of patient support apparatus 20, or 20a, rather than (or in addition to) the display of the electronic devices 104. Controller 48 of system 106c is therefore configured to execute a software application that displays the information shown in FIGS. 10-14 on display 70 and provides the same functionality as those screens. The caregiver, for example, enters the patient's pain level using plus and minus icons 210 and 212 and a next icon 214 that are displayed on display screen 70 of the corresponding patient support apparatus 20 or 20a (see FIG. 10).

In the embodiment of FIG. 30, mobile electronic device 104a does not need to receive any compliance data from the patient support apparatus 20 or 20a because this information is sent from the patient support apparatus 20 to caregiver assistance application 124 (via messages 310). Indeed, in some embodiments of system 106c, mobile electronic devices 104a may be dispensed with entirely, or used only to receive alerts and/or status updates. Alternatively, mobile electronic devices 104a may be used to display information about the rounding status and/or patient support apparatus status, but not accept any inputs regarding patient rounding and/or fall risk assessments (and, in some embodiments, not accept any commands for commanding the patient support apparatus).

In the embodiment of FIG. 30, patient support apparatus 20 or 20a may be configured to require a user to enter a username and/or a password before allowing the caregiver to input the rounding information and/or fall risk assessment data into patient support apparatus 20 or 20a. Such access may be carried out in the same or similar manner to what is illustrated in FIGS. 7 and 8. Alternatively, in some embodiments, patient support apparatus 20 or 20a may be configured to allow the caregiver to enter rounding data and/or fall risk data without first establishing his or her credentials.

In the caregiver assistance system 106c of FIG. 30, neither mobile electronic device 104a nor patient support apparatus 20 (or 20a) sends any verification data to caregiver assistance server 90. This is because the rounding data comes to caregiver assistance server 90 via messages 310 from patient support apparatus 20 or 20a. Because such messages 310 are specifically received from patient support apparatus 20 or 20a, and are only sent in response to the caregiver manipulating one or more controls on the patient support apparatus 20 or 20a, the very sending of such messages 310 is verification that the caregiver is present adjacent the patient support apparatus 20 or 20a. In other words, because messages 310 originate from patient support apparatuses 20 or 20a in response to caregiver actions, such messages inherently provide their own verification of the caregiver's presence.

It will be understood that caregiver assistance system 106c of FIG. 30 may be modified in a number of different manners. For example, in at least one modified embodiment, rounding algorithm 140 is modified so that no rounding questions and/or fall risk assessment questions are displayed, and/or caregiver assistance application 124 does not wait for receipt of any answers for the rounding questions in algorithm 140. In this modified embodiment, it is assumed that the caregivers will ask the proper questions for either or both of the rounding task and the fall risk assessment task while they are present in the patient's room. Therefore, system 106c assumes that rounding questions and rounding tasks are properly asked and implemented whenever the caregiver is present in a patient's room, and also assumes that whenever it receives a fall risk assessment score, the proper fall risk assessment questions were asked. As a result of the former assumption, this modified embodiment of system 106c concludes that a caregiver has properly performed a rounding task whenever his or her presence within a patient's room is detected (while the patient is present in that room). As a result of the latter assumption, caregiver assistance application 124 concludes that the caregiver has properly determined the fall risk of a patient without having seen the specific questions used in the fall risk assessment. Accordingly, in this modified embodiment, patient support apparatus 20 or 20a is configured to send a rounding confirmation message 310 to caregiver assistance server 90 whenever it detects the presence of a caregiver. The message includes data indicating the detection of the caregiver's presence, and caregiver assistance application 124 interprets this data as an indication that the caregiver has completed a round with that particular patient. If the message includes a fall risk assessment, or a separate message 310 is sent that includes a fall risk assessment, caregiver assistance application 124 interprets this assessment as properly reflecting the patient's fall risk according to the questions utilized by that particular healthcare facility.

In this modified embodiment of system 106c, the presence of a caregiver within a room can be detected in a variety of different manners. In one implementation, patient support apparatus 20 or 20a is modified to send a message 310 whenever a button or control is activated on one of the caregiver control panels 42a or 42c. For example, if the scale controls are used to weigh the patient, or a therapy control is used to implement a mattress therapy, or the exit detection system is armed, controller 48 of patient support apparatus 20 or 20*a* sends a message 310 to caregiver assistance server indicating that a caregiver has activated a control on patient support apparatus 20 or 20*a*. The message 310 is sent because system 106*c* assumes that such button or control activations are the result of a caregiver's actions, not the patient's actions. As a result, the message 310 includes data indicating that a caregiver is present in the room. The message 310 may include data identifying the specific control that has been activated and/or a time at which the control was activated. Alternatively, message 310 may simply indicate that a caregiver control was activated without specifying which one and/or without specifying a time.

In another implementation of this modified embodiment of system 106*c*, the caregiver carries a card (an RF ID card, a card with a magnetic strip, a near field communication card, or another type of card) that is detected by a corresponding sensor on the patient support apparatus 20 or 20*a* when the caregiver is within relatively close proximity to the patient support apparatus 20 or 20*a* (e.g. within the same room, or closer). In response to detecting the card, patient support apparatus 20 or 20*a* sends a message 310 to caregiver assistance application 124 indicating the presence of the caregiver, and caregiver assistance application 124 treats that message 310 as proof that the caregiver has completed a round with the patient. The message 310 may also include patient support apparatus data that caregiver assistance application 124 uses to determine if the patient support apparatus 20 or 20*a* is in a compliant or non-compliant state. This data (the compliancy data and rounding completion data) is then sent to EMR server 98, as discussed above with respect to step 256 of algorithm 140.

In this modified embodiment of caregiver assistance system 106*c*, patient support apparatus 20 (or 20*a*) and/or mobile electronic device 104*a* can be designed to omit the display of any rounding questions and/or rounding related screens shown in FIGS. 10-17. In other words, in this modified embodiment, because the caregiver is assumed to perform his/her rounding duties correctly whenever present in the patient's room, there is no need to display the questions shown in FIGS. 10-13 and/or receive answers to those questions. The display of these screens can therefore be omitted. The same is true for the fall risk assessment questions and associated screens. That is, they may be omitted in some embodiments, but retained in other embodiments. Further, there is no need to include the verification screens of FIGS. 15-17 because the caregiver's presence is inherently verified in this embodiment (i.e. the caregiver's presence is the trigger in this embodiment for concluding that a rounding task has been completed). Indeed, in this embodiment, the web API 132 of caregiver assistance server 90 can be omitted entirely, if desired, along with need for any devices (electronic devices 104*a*, 104*b*, or patient support apparatuses 20 or 20*a*) to log into this modified version of system 106*c*.

It will be understood by those skilled in the art that any of the components, functions, and/or features of the different embodiments of caregiver assistance systems 106, 106*a*, 106*b*, and 106*c* may be combined together, substituted, and/or mixed in any manner. As but one non-limited example, system 106 may be modified to omit the display of any rounding questions, similar to modified system 106*c*, and the patient support apparatuses 20 of system 106 may be modified to display a code that identifies the bed and the current time. In this modified system, the caregiver is assumed to ask the desired rounding questions and take care of the desired rounding tasks, and the modified system merely verifies the caregiver's presence in the patient's rooms. This presence is verified by the modified patient support apparatus displaying the code and the caregiver capturing an image of this code using his or her mobile electronic device 104*a* that sends the captured image to caregiver assistance server 90. In some embodiments, the code includes both the bed ID and time, while in other embodiments the code includes only the bed ID. In still other embodiments, the bed ID and/or time are not coded at all, but merely displayed so that an image of them can be captured by the caregiver's mobile electronic device 104*a*. In a variation on this embodiment, the patient support apparatus 20 may be configured to not display the ID and/or time (or the code) or the patient support apparatus ID if the patient support apparatus is not currently in a compliant state, or it may simultaneously display the fact that it is not in a compliant state along with the ID and/or time (or a code with such information).

It will also be understood that, in any of the embodiments discussed above that utilize one or more near field transceivers incorporated into any of the patient support apparatuses 20 or 20*a*, such patient support apparatuses 20 or 20*a* may constructed to include such near field transceivers and/or utilize the near field transceivers in any of the manners disclosed in commonly assigned U.S. Pat. No. 9,966,997 issued May 8, 2018, to inventors Michael Hayes et al. and entitled COMMUNICATION SYSTEMS FOR PATIENT SUPPORT APPARATUSES, the complete disclosure of which is incorporated herein by reference.

Still further, it will be understood that any of the embodiments of caregiver assistance system 106 may omit one or more of the algorithms shown in FIG. 3, and/or these algorithms may be supplemented with additional algorithms. Thus, for example, in some modified embodiments, caregiver assistance system 106 (or 106*a*, 106*b*, or 106*c*) is only configured to implement fall-risk reduction algorithm 143 without implementing rounding algorithm 140, or vice versa. In still other embodiments, still other combinations of two or more of the algorithms shown in FIG. 3 may be implemented by the system. Further, it will be understood that additional modifications may be made to individual algorithms beyond those already discussed above, such as, but not limited to, modifying fall risk reduction algorithm 143 to omit the fall risk assessment questions, or to include additional fall risk screens beyond those illustrated herein.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A caregiver assistance system for assisting a caregiver to reduce patient fall risks, the caregiver assistance system comprising:
   (a) a plurality of beds, each of the beds comprising:
      a litter frame;
      a support deck supported on the litter frame and configured to support a patient thereon;
      a memory containing an identifier uniquely identifying the respective bed;
      a transceiver;
      a sensor configured to detect a state of a fall-risk component of the respective bed;
      and
      a controller in communication with the memory, the sensor, and the transceiver, the controller configured to transmit a message via the transceiver, the message including the respective identifier; and
   (b) a server configured to execute a caregiver assistance application, the caregiver assistance application configured to receive a patient fall risk assessment from an external device, the patient fall risk assessment identifying a fall risk of a particular patient, wherein the caregiver assistance application is further configured to receive the messages from the plurality of beds and to match the patient fall risk assessment to a specific one of the beds to which the particular patient has been assigned; and wherein the external device is one of a smart phone, a tablet computer, or a laptop computer carried by a caregiver and configured to receive fall risk data from the caregiver, the external device configured to generate the patient fall risk assessment from the fall risk data, and wherein the fall risk data includes answers to a set of questions regarding the particular patient.

2. The caregiver assistance system of claim 1 wherein the server includes a memory in which state data is stored defining a desired state of the fall-risk component for patients having a high fall risk, and the caregiver assistance application is configured to determine if the fall risk of the particular patient qualifies as a high fall risk and, if it does, to determine if the fall-risk component of the specific one of the beds is in the desired state based upon data received from the sensor of the specific one of the beds.

3. A caregiver assistance system for assisting a caregiver to reduce patient fall risks, the caregiver assistance system comprising:
   (a) a plurality of beds, each of the beds comprising:
      a litter frame;
      a support deck supported on the litter frame and configured to support a patient thereon;
      a memory containing an identifier uniquely identifying the respective bed;
      a transceiver;
      a sensor configured to detect a state of a fall-risk component of the respective bed;
      and
      a controller in communication with the memory, the sensor, and the transceiver, the controller configured to transmit a message via the transceiver, the message including the respective identifier; and
   (b) a server configured to execute a caregiver assistance application, the caregiver assistance application configured to receive a patient fall risk assessment from an external device, the patient fall risk assessment identifying a fall risk of a particular patient, wherein the caregiver assistance application is further configured to receive the messages from the plurality of beds and to match the patient fall risk assessment to a specific one of the beds to which the particular patient has been assigned; and wherein the server includes a memory in which state data is stored defining a desired state of the fall-risk component for patients having a high fall risk, and the caregiver assistance application is configured to determine if the fall risk of the particular patient qualifies as a high fall risk and, if it does, to determine if the fall-risk component of the specific one of the beds is in the desired state based upon data received from the sensor of the specific one of the beds.

4. The caregiver assistance system of claim 3 wherein the specific one of the beds includes a plurality of sensors configured to detect states of a plurality of fall-risk components;
   the state data includes desired states for each of the plurality of fall-risk components; and the caregiver assistance application is further configured to determine if any of the plurality of fall-risk components of the specific one of the beds are not in their respective desired states, to communicate with a mobile electronic device carried by a caregiver, to provide data to the mobile electronic device indicating whether the plurality of fall-risk components of the specific one of the beds are in their respective desired states or not, to provide data to the mobile electronic device identifying the fall-risk component, and to provide a graphical depiction of the specific one of the beds and identifies the fall-risk component on the graphical depiction.

5. The caregiver assistance system of claim 4 wherein the plurality of fall-risk components of the specific one of the beds includes the following:
   a brake configured to selectively brake a wheel;
   a siderail configured to move between a raised and lowered position;
   a lift system configured to change a height of the litter frame; and
   an exit detection system configured to issue an alert when the exit detection system is armed and the particular patient exits from the specific one of the beds; and
   wherein the external device is one of an electronic medical records (EMR) server or an Admission, Discharge, and Tracking (ADT) server.

6. The caregiver assistance system of claim 4 wherein the mobile electronic device is a browser enabled device configured to receive the data from the caregiver assistance application by accessing at least one Uniform Resource Locator (URL) associated with the server; wherein the mobile electronic device is further configured to receive a room identifier from the caregiver and to forward the room identifier to the caregiver assistance application; and wherein the caregiver assistance application is configured to associate the room identifier with the particular patient.

7. The caregiver assistance system of claim 6 wherein the caregiver assistance application is further configured to cause the mobile electronic device to display an alert if any of the plurality of fall-risk components of the specific one of the beds are not in their respective desired states; and to cause the mobile electronic device to display rounding data thereon, the rounding data indicating at least one of: an amount of time since a caregiver last completed a rounding task associated with the particular patient, or an amount of time until the caregiver is supposed to complete a future rounding task associated with the particular patient.

8. A caregiver assistance system for assisting a caregiver to reduce patient fall risks, the caregiver assistance system comprising:
(a) a bed comprising:
  a litter frame;
  a support deck supported on the litter frame and configured to support a patient thereon;
  a memory containing an identifier uniquely identifying the bed;
  a transceiver;
  a plurality of sensors configured to detect states of a plurality of fall-risk components of the bed; and
  a controller in communication with the memory, the sensor, and the transceiver, the controller configured to transmit the identifier and the states of the plurality of fall-risk components; and
(b) a server configured to execute a caregiver assistance application, the caregiver assistance application configured to receive the identifier and the states of the plurality of fall-risk components of the bed and to monitor compliance of the plurality of fall-risk components with a fall risk reduction protocol, the caregiver assistance application configured to communicate with a mobile electronic device comprising a display, a user input, and a web browser configured to be able to access a particular Uniform Resources Locator (URL) associated with the caregiver assistance application, the caregiver assistance application further configured to cause the mobile electronic device to perform the following after accessing the particular URL:
  (i) display the states of the plurality of fall-risk components of the bed;
  (ii) receive fall risk data via the user input from a caregiver associated with the mobile electronic device and the bed;
  (iii) transmit the fall risk data to the server; and
  (iv) issue an alert if any of the states of the plurality of fall-risk components of the bed do not comply with the fall risk reduction protocol.

9. The caregiver assistance system of claim 8 wherein the caregiver assistance application is further configured to cause the mobile electronic device to perform the following after accessing the particular URL: display a set of questions relating to a fall risk of the patient; receive answers to the set of questions; and transmit the answers to the server; and wherein the caregiver assistance application is further configured to also cause the mobile electronic device to perform the following after accessing the particular URL: receive data from the user input defining a change to the fall risk reduction protocol.

10. The caregiver assistance system of claim 8 wherein the plurality of fall-risk component comprises:
(a) a brake configured to selectively brake a wheel;
(b) a siderail configured to move between a raised and lowered position;
(c) a lift system configured to change a height of the litter frame; and
(d) an exit detection system configured to issue an alert when the exit detection system is armed and the patient exits from the bed; and
wherein the plurality of sensors comprises:
(i) a brake sensor configured to detect whether the brake is activated or inactivated;
(ii) a siderail position sensor configured to detect whether the siderail is in the raised or lowered position;
(iii) a height sensor configured to detect a height of the litter frame; and
(iv) an exit detection armed sensor configured to detect when the exit detection system is armed or not; and
wherein the fall risk reduction protocol defines desired states for each of the brake, siderail, lift system, and exit detection system.

11. The caregiver assistance system of claim 9 wherein the caregiver assistance application is further configured to use the answers to the set of questions received from the mobile electronic device to generate a patient fall risk assessment, and to determine whether the fall risk reduction protocol is to be followed for the bed or not based upon the patient fall risk assessment.

12. The caregiver assistance system of claim 11 wherein the caregiver assistance application is further configured to forward the patient fall risk assessment to an electronic medical records server in communication with the server; wherein the mobile electronic device is one of a smart phone, a tablet computer, or a laptop computer; wherein the bed further comprises a user interface configured to allow a user to input data defining the fall risk reduction protocol; and wherein the caregiver assistance application is further configured to receive the data defining the fall risk reduction protocol from the bed.

13. The caregiver assistance system of claim 10 wherein the caregiver assistance application is further configured to cause the mobile electronic device to display rounding data thereon, the rounding data indicating at least one of: an amount of time since a caregiver last completed a rounding task associated with the patient, or an amount of time until the caregiver is supposed to complete a future rounding task associated with the patient; and wherein the caregiver assistance application is still further configured to allow the mobile electronic device to receive a command to arm the exit detection system from a user and to forward the command to the bed, wherein the controller arms the exit detection system in response to receiving the command.

14. A caregiver assistance system for assisting a caregiver to reduce patient fall risks, the caregiver assistance system comprising:
(a) a bed comprising:
  a litter frame;
  a support deck supported on the litter frame and configured to support a patient thereon;
  a memory containing an identifier uniquely identifying the bed;
  a transceiver;
  a plurality of sensors configured to detect states of a plurality of fall-risk components of the bed; and
  a controller in communication with the memory, the sensor, and the transceiver, the controller configured to transmit the identifier and the states of the plurality of fall-risk components; and
(b) a server configured to execute a caregiver assistance application, the caregiver assistance application configured to perform the following:
  (i) communicate with a mobile electronic device comprising a display and a user input;
  (ii) receive from the mobile electronic device answers to a plurality of fall risk questions;
  (iii) generate a patient fall risk assessment from the answers;
  (iv) determine a desired state for each of the plurality of fall-risk components of the bed if the patient fall risk assessment indicates the patient has a high risk of falling;

(v) compare the states of the plurality of fall-risk components to corresponding ones of the desired states of each of the plurality of fall-risk components; and (vi) issue an alert at the mobile electronic device if at least one of the states of the plurality of fall-risk components does not match the corresponding desired state.

15. The caregiver assistance system of claim 14 wherein the plurality of fall-risk component comprises:

(a) a brake configured to selectively brake a wheel;

(b) a siderail configured to move between a raised and lowered position;

(c) a lift system configured to change a height of the litter frame; and (d) an exit detection system configured to issue an alert when the exit detection system is armed and the patient exits from the bed; and wherein the plurality of sensors comprises:

(i) a brake sensor configured to detect whether the brake is activated or inactivated;

(ii) a siderail position sensor configured to detect whether the siderail is in the raised or lowered position;

(iii) a height sensor configured to detect a height of the litter frame; and (iv) an exit detection armed sensor configured to detect when the exit detection system is armed or not; and wherein the desired state for each of the plurality of fall-risk components of the bed includes a desired state for each of the brake, siderail, lift system, and exit detection system.

16. The caregiver assistance system of claim 15 wherein the caregiver assistance application is further configured to determine the desired state for each of the plurality of fall-risk components by consulting a fall risk reduction protocol stored in the memory, the fall risk reduction protocol specifying desired states for each of the plurality of fall-risk components when the patient has a high risk of falling, and wherein the bed further comprises a user interface configured to allow a user to input data defining the fall risk reduction protocol and the caregiver assistance application is further configured to receive and store in the memory the data defining the fall risk reduction protocol from the bed.

17. The caregiver assistance system of claim 15 wherein the caregiver assistance application is further configured to forward the patient fall risk assessment to an electronic medical records server in communication with the server, and to cause the mobile electronic device to display rounding data thereon, the rounding data indicating at least one of: an amount of time since a caregiver last completed a rounding task associated with the patient, or an amount of time until the caregiver is supposed to complete a future rounding task associated with the patient.

18. The caregiver assistance system of claim 15 wherein the caregiver assistance application is configured to allow an authorized administrator change the plurality of fall risk questions.

19. The caregiver assistance system of claim 15 wherein the mobile electronic device is configured to communicate with the caregiver assistance application via a Uniform Resources Locator (URL) associated with the caregiver assistance application; wherein the caregiver assistance application is configured to issue the alert by sending at least one of the following to the mobile electronic device: an email or a text message; and wherein the mobile electronic device is one of a smart phone, a tablet computer, or a laptop computer.

20. The caregiver assistance system of claim 17 wherein the caregiver assistance application is further configured to cause the mobile electronic device to receive rounding data from a caregiver indicating the rounding task was completed, and to cause the mobile electronic device to capture verification data verifying the caregiver was physically present adjacent the bed at a time the rounding task was completed; wherein the verification data is derived from at least one of the following: image data of at least a portion of the bed captured by a camera included within the mobile electronic device, or data communicated from the bed to the mobile electronic device using near field communication.

* * * * *